US012371522B2

(12) United States Patent
Green et al.

(10) Patent No.: US 12,371,522 B2
(45) Date of Patent: Jul. 29, 2025

(54) BIOREDUCIBLE POLY (BETA-AMINO ESTER)S FOR SIRNA DELIVERY

(71) Applicant: THE JOHNS HOPKINS UNIVERSITY, Baltimore, MD (US)

(72) Inventors: Jordan J Green, Nottingham, MD (US); Kristen Kozielski, Baltimore, MD (US); Stephany Yi Tzeng, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/438,353

(22) PCT Filed: Oct. 25, 2013

(86) PCT No.: PCT/US2013/066901
§ 371 (c)(1),
(2) Date: Apr. 24, 2015

(87) PCT Pub. No.: WO2014/066811
PCT Pub. Date: May 1, 2014

(65) Prior Publication Data
US 2015/0273071 A1    Oct. 1, 2015
US 2019/0209690 A9    Jul. 11, 2019

Related U.S. Application Data

(63) Continuation-in-part of application No. 13/272,042, filed on Oct. 12, 2011, now Pat. No. 9,717,694.

(60) Provisional application No. 61/883,376, filed on Sep. 27, 2013, provisional application No. 61/860,638, filed on Jul. 31, 2013, provisional application No. 61/718,536, filed on Oct. 25, 2012.

(51) Int. Cl.
| | | |
|---|---|---|
| A61K 9/00 | (2006.01) | |
| A61K 9/51 | (2006.01) | |
| A61K 31/713 | (2006.01) | |
| A61K 47/32 | (2006.01) | |
| A61K 47/59 | (2017.01) | |
| A61K 47/69 | (2017.01) | |
| A61L 27/18 | (2006.01) | |
| A61L 27/38 | (2006.01) | |
| A61L 27/56 | (2006.01) | |
| A61L 27/58 | (2006.01) | |
| A61L 31/10 | (2006.01) | |
| A61L 31/14 | (2006.01) | |
| C07C 323/12 | (2006.01) | |
| C07D 295/125 | (2006.01) | |
| C08F 222/14 | (2006.01) | |
| C08G 73/02 | (2006.01) | |
| C12N 15/88 | (2006.01) | |

(52) U.S. Cl.
CPC .......... *C08F 222/14* (2013.01); *A61K 9/5153* (2013.01); *A61K 31/713* (2013.01); *A61K 47/32* (2013.01); *A61K 47/595* (2017.08); *A61K 47/6921* (2017.08); *A61L 27/18* (2013.01); *A61L 27/38* (2013.01); *A61L 27/56* (2013.01); *A61L 27/58* (2013.01); *A61L 31/10* (2013.01); *A61L 31/148* (2013.01); *C07C 323/12* (2013.01); *C07D 295/125* (2013.01); *C08G 73/0253* (2013.01); *C12N 15/88* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 5,948,878 A | 9/1999 | Burgess | |
| 2002/0141965 A1 | 10/2002 | Ahn | |
| 2008/0299177 A1 | 12/2008 | Hardy | |
| 2010/0178305 A1 | 7/2010 | Rapoport | |
| 2010/0204297 A1* | 8/2010 | Chen ................. | C12N 15/1131 435/320.1 |
| 2011/0076307 A1 | 3/2011 | Jin | |
| 2012/0114759 A1 | 5/2012 | Green | |
| 2012/0128782 A1 | 5/2012 | Green | |

(Continued)

FOREIGN PATENT DOCUMENTS

| | | |
|---|---|---|
| CA | 2304134 | 4/1999 |
| WO | 2007020060 A1 | 2/2007 |

(Continued)

OTHER PUBLICATIONS

Yin et al., J. Control. Rel., online Jan. 16, 2011, 151: 35-44.*

(Continued)

*Primary Examiner* — Ileana Popa
(74) *Attorney, Agent, or Firm* — Casimir Jones, SC; Jeffrey W. Childers

(57) ABSTRACT

Degradable polymers were synthesized that self-assemble with nucleic acids, proteins, hydrophobic drugs, and other small molecules to form particles that are effective for delivery into a cell, tissue and/or organism either in vitro or in vivo. The presently disclosed polymers demonstrate differential cell-type specificity, an ability to promote endosomal escape to protect the cargos from degradation and enhance delivery to the cytoplasm, and/or bioreducibility, which enables triggered intracellular drug release to be tuned to promote optimal delivery to the target cell type. The presently disclosed materials may be used to treat a wide variety of conditions or diseases, such as cancer, cardiovascular diseases, infectious diseases, and ophthalmic diseases.

31 Claims, 20 Drawing Sheets

(56) References Cited

U.S. PATENT DOCUMENTS

| | | |
|---|---|---|
| 2013/0211249 A1 | 8/2013 | Barnett et al. |
| 2014/0341803 A1 | 11/2014 | Rapoport |

FOREIGN PATENT DOCUMENTS

| | | |
|---|---|---|
| WO | 2007086923 A2 | 8/2007 |
| WO | 2010132879 A2 | 11/2010 |
| WO | 2011078805 A1 | 6/2011 |

OTHER PUBLICATIONS

Kim et al., Bioconjugate Chem., 2005, 16: 1140-1148.*
Sunshine et al., Adv. Mater., 2009, 21: 4947-4951.*
Pfeifer et al., Int. J. Pharm., 2005, 304: 210-219.*
Vandenbroucke et al., J. Gene Med., 2008, 10: 783-794.*
Kuwabara, P. E. et al. RNAi-prospects for a general technique for determining gene function. Parasitol Today 2000, 16, 347-9.
Lynn, D. M., et al. Degradable poly (B-amino esters): synthesis, characterization, and self-assembly with plasmid DNA. Journal of the American Chemical Society 2000, 122, 44, 10761-10768.
Sunshine, J. C., et al. Uptake and Transfection with Polymeric Nanoparticles are Dependent on Polymer End-Group Structure, but Largely Independent of Nanoparticle Physical and Chemical Properties. Molecular Pharmaceutics 2012, 9(11), 3375-3383.
Griffith, O. W. Biologic and pharmacologic regulation of mammalian glutathione synthesis. Free Radical Biology and Medicine 1999, 27, 922-935.
Chen, J. et al. pH and Reduction Dual-Sensitive Copolymeric Micelles for Intracellular Doxorubicin Delivery. Biomacromolecules, 2011, 12, 3601-11.
T. G. Park, J. H. Jeong, and S. W. Kim, "Current status of polymeric gene delivery systems," Advanced Drug Delivery Reviews, vol. 58, pp. 467-486, 2006.
Pack, D. et al, "Design and development of polymers for gene delivery," Nature Reviews Drug Discovery, vol. 4, pp. 581-593, 2005.
Akinc, A. et al, "Exploring polyethylenimine-mediated DNA transfection and the proton sponge hypothesis," Journal of Gene Afedicine, vol. 7, pp. 657-663, May 2005.
Putnam, D. et al, "Polymer-based gene delivery with low cytotoxicity by a unique balance of side-chain tennini," Proc Natl Acad Sci USA, vol. 98, pp. 1200-1205, Jan. 30, 2001.
Moghimi, S. et al, "A two-stage poly(ethylenimine)-mediated cytotoxicity: implications for gene transfer/therapy," Afol Ther, vol. 11, pp. 990-995, Jun. 2005.
Akinc, A. et al, "Parallel synthesis and biophysical characterization of a degradable polymer library for gene delivery," Journal of the American Chemical Society, vol. 125, pp. 5316-5323, May 7, 2003.
Green, J. et al, "Biodegradable polymeric vectors for gene delivery to human endothelial cells," Bioconjugate Chemistry, vol. 17, pp. 1162-1169, 2006.
Akinc, A. et al, "Synthesis of poly(beta-amino ester)s optimized for highly effective gene delivery," Bioconjugate Chemistry, vol. 14, pp. 979-988, Sep.-Oct. 2003.
Green, J. et al, "Combinatorial modification of degradable polymers enables transfection of human cells comparable to adenovirus," Advanced A1aterials, vol. 19, pp. 2836-2842, 2007.
Gosselin, M. et al, "Efficient gene transfer using reversibly cross-linked low molecular weight polyethylenimine," Bioconjugate Chemistry, vol. 12, pp. 989-994, Nov.-Dec. 2001.
Forrest, M. et al, "A degradable polyethylenimine derivative with low toxicity for highly efficient gene delivery," Bioconjug Chem, vol. 14, pp. 934-940, Sep.-Oct. 2003.
Christensen, L. et al, "Reducible poly(amido ethylenimine)s designed for triggered intracellular gene delivery," Bioconjugate Chemistry, vol. 17, pp. 1233-1240, Sep.-Oct. 2006.

Lin, C. et al, "Bioreducible poly(amido amine)s with oligoamine side chains: synthesis, characterization, and structural effects on gene delivery," Journal of Controlled Release, vol. 126, pp. 166-174, Mar. 3, 2008.
Yu, J. et al, "Induced pluripotent stem cell lines derived from human somatic cells," Science, vol. 318, pp. 1917-1920, Dec. 21 2007.
Yadav, S., et al. "Evaluations of combination MDR-1 gene silencing and paclitaxel administration in biodegradable polymeric nanoparticle formulations to overcome multidrug resistance in cancer cells"Cancer Chemother. Pharmacol. 2009, 63, (4), 711-22.
Akinc, A., et al. A combinatorial library of lipid-like materials for delivery of RNAi therapeutics. Nat. Biotechnol. 2008, 26, (5), 561-569.
Semple, S. et al, "Rational design of cationic lipids for siRNA delivery" J. Nat. Biotechnol. 2010, 28, (2), 172-6.
Derfus, A. et al. "Targeted Quantum Dot Conjugates for siRNA Delivery" Bioconjugate Chem. 2007, 18, (5), 1391-1396.
Elbakry, A. et al. "Layer-by-layer assembled gold nanoparticles for siRNA delivery" Nano Lett. 2009, 9, (5), 2059-2064.
Kakizawa, Y., et al. "Organic-inorganic hybrid-nanocarrier of siRNA constructing through the self-assembly of calcium phosphate and PEG-based block aniomer" J. Control. Release 2006, 111, (3), 368-370.
Breunig, M., et al. "Mechanistic investigation of poly (ethylene imine)-based siRNA delivery: disulfide bonds boost intracellular release of the cargo" J. Control Release 2008, 130, (1), 57-63.
Jeong, J. H., "Reducible poly(amido ethylenimine) directed to enhance RNA interference" Biomaterials 2007, 28, (10), 1912-1917.
Matsumoto, S., et al. "Environment-Responsive Block Copolymer Micelles with a Disulfide Cross-Linked Core for Enhanced siRNA Delivery" Biomacromolecules 2009, 10, (1), 119-127.
Hagerman, P., "Flexibility of RNA" J. Annu. Rev. Biophys. Biomol. Struct. 1997, 26, 139-156.
Kebbekus, P., et al "Persistence Length of RNA" Biochemistry 1995, 34, (13), 4354-4357.
Miyata, K., et al. "Block Catiomer Polyplexes with Regulated Densities of Charge and Disulfide Cross-Linking Directed to Enhance Gene Expression" J. Am. Chem. Soc. 2004, 126, (8), 2355-2361.
Tzeng, S., et al "Cystamine-terminated poly(beta-amino ester)s for siRNA delivery to human mesenchymal stem cells and enhancement of osteogenic differentiation" Biomaterials 2012, 33, (32), 8142-8151.
Bhise, N., et al. "A novel assay for quantifying the numbers of plasmids encapsulated by polymer nanoparticles" Small 2012, 8, (3), 367-373.
Yin, Q. et al. Bioreducible poly (B-amino esters)/shRNA complex nanoparticles for efficient RNA delivery. Journal of Controlled Release 151 (2011) 35-44.
Kim, T. et al. Bioreducible polymers for gene delivery. Reactive & Functional Polymers 71 (2011) 344-349.
Son, S. et al. Bioreducible Polymers for Gene Silencing and Delivery. Accounts of Chemical Research vol. 45, No. 7 (2012) 1100-1112.
Kim, T., et al. Bioreducible polymers with cell penetrating and endosome buffering functionality for gene delivery systems. Journal of Controlled Release 152 (2011) 110-119.
H. Akita, et al. Delivery of Nucleic Acids and Gene Delivery. Comprehensive Biomaterials, 2011, pp. 411-444.
Jiang, X., et al. Disulfide-Containing Hyperbranched Polyethylenimine Derivatives via Click Chemistry for Nonviral Gene Delivery. Macromol. Chem. Phys. 2011, 212, 64-71.
Morille, M. et al. Progress in developing cationic vectors for non-viral systemic gene therapy against cancer. Biomaterials 29 (2008) 3477-3496.
Meng, F., et al. Reduction-sensitive polymers and bioconjugates for biomedical applications. Biomaterials 30 (2009) 2180-2198.
Kim, S., et al. Reductive Degradation Behavior of Bioreducible Poly(disulfide amine) for Enhancing SiRNA Efficiency. Macromol. Biosci. 2010, 10, 898-905.

(56) References Cited

OTHER PUBLICATIONS

Tzeng, S. et al. Subtle changes to polymer structure and degradation mechanism enable highly effective nanoparticles for siRNA and DNA delivery to human brain cancer. Advanced Healthcare Materials 2013, 2(3): 468-‒80.
Fire, A., et al. "Potent and specific genetic interference by double-stranded RNA in Caenorhabditis elegans" Nature, 1998, 391, 806-811.
Green, J. et al, "A Combinatorial Polymer Library Approach Yields Insight into Nonviral Gene Delivery" Acc. Chem. Res., 2008, 41, 749-759.
Peng, Q. et al "Disulfide cross-linked polyethylenimines (PEI) prepared via thiolation of low molecular weight PEI as highly efficient gene vectors" Bioconjugate Chem., 2008, 19, 499-506.
Van der Aa, L. et al, "Optimization of poly(amido amine)s as vectors for siRNA delivery" J. Controlled Release, 2011, 150, 177-186.
Yin, Q. et al. "Overcoming multidrug resistance by co-delivery of Mdr-1 and survivin-targeting RNA with reduction-responsible cationic poly(B-amino esters)" Biomaterials, 2012, 33, 6495-6506.
Lee, J. et al, "Gold, poly (β-amino ester) nanoparticles for small interfering RNA delivery" Nano Lett., 2009, 9, 2402-2406.
Ravin, R. et al. Shear Forces During Blast, Not Abrupt Changes in Pressure Alone, Generate Calcium Activity in Human Brain Cells. PLoS One 2012, 7, e39421.
International Search Report dated Feb. 14, 2014; International Application No. PCT/US2013/066901.
Pieter Vader et al., "Disulfide-Based Poly(amido amine)s for siRNA Delivery: Effects of Structure on siRNA Complexation, Cellular Uptake, Gene Silencing and Toxicity," Pharm. Res. 2011, vol. 28, pp. 1013-1022.
Dhananjay Jere et al., "Poly(b-amino ester) as a carrier for si/shRNA delivery in lung cancer cells," Biomaterials, 2008, vol. 29, pp. 2535-2547.
M. C. Pedroso de Lima, S. Simoes, P. Pires, H. Faneca, and N. Duzgunes, "Cationic lipid-DNA complexes in gene delivery: from biophysics to biological applications," Advanced Drug Delivery Reviews, vol. 47, pp. 277-294, Apr. 25, 2001.
N. D. Sonawane, F. C. Szoka, and AS. Verkman, "Chloride accumulation and swelling in endosomes enhances DNA transfer by polyamine-DNA polyplexes," Journal of Biological Chemistry, vol. 278, pp. 44826-44831, Nov. 7, 2003.
D. G. Anderson, A. Akinc, N. Hossain, and R. Langer, "Structure/property studies of polymeric gene delivery using a library of poly (beta-amino esters)," Molecular Therapy, vol. 11, pp. 426-434, Mar. 2005.
G. T. Zugates, W. Peng, A. Zumbuehl, S. Jhunjhunwala, Y.H. Huang, R. Langer, J. A Sawicki, and D. G. Anderson, "Rapid Optimization of Gene Delivery by Parallel End-modification of Poly(beta-amino ester)s," A1ol Ther, vol. 15, pp. 1306-1312, 2007.
M. M. O. Sullivan, J. J. Green, and T. M. Przybycien, "Development of a novel gene delivery scaffold utilizing colloidal gold-polyethylenimine conjugates for DNA condensation," Gene Therapy, vol. 10, pp. 1882-1890, Oct. 2003.
A. J. Ewald, A. Brenot, M. Duong, B. S. Chan, and Z. Werb, "Collective Epithelial Migration and Cell Rearrangements Drive Mammary Branching Morphogenesis" Dev Cell. vol. 14(4) pp. 570-581, Apr. 2008.
Rutz, S., and Scheffold, A., Arthritis Res Ther 2004, 6, 78-85 (2004).
David Oupick et al., "Redox-Responsive Polymer-Based Gene Delivery Systems", Gene and Cell Therapy, Therapeutic Mechanisms and Strategies, Third Edition, Chapter 13, Nancy Smyth Templeton, CRC Press 2008.
Bhise, N. et al "The relationship between terminal functionalization and molecular weight of a gene delivery polymer and transfection efficacy in mammary epithelial 2-D cultures and 3-D organotypic cultures", Biomaterials, 2010, 31, 8088-8096.
Tzeng, S. et al "Synthetic poly (ester amine) and poly (amido amine) nanoparticles for efficient DNA and siRNA delivery to human endothelial cells", Int. J. Nanomed., 2011, 6, 3309-3322.
Tzeng, S. et al, "Non-viral gene delivery nanoparticles based on Poly(β-amino esters) for treatment of glioblastoma" Biomaterials, 2011, 32, 5402-5410.
Wu, W. et al, MicroRNA and Cancer: Current Status and Prospective. Int. J. Cancer 2007, 120, 953-60.
Boussif, O. et al. A Versatile Vector for Gene and Oligonucleotide Transfer into Cells in Culture and in-Vivo-Polyethylenimine. Proc. Natl. Acad. Sci. 1995, 92, 7297-7301.
Kawasaki, H. et al, Short Hairpin Type of Dsrnas That are Controlled by Trnaval Promoter Significantly Induce RNAi-Mediated Gene Silencing in the Cytoplasm of Human Cells. Nucleic Acids Res. 2003, 31, 700-707.
Tzeng, S. et al, Subtle Changes to Polymer Structure and Degradation Mechanism Enable Highly Effective Nanoparticles for siRNA and DNA Delivery to Human Brain Cancer. Adv. Healthcare Mater. 2013, 2, 467.
Kozielski, K. et al, A Bioreducible Linear Poly(Beta-Amino Ester) for siRNA Delivery. Chem. Commun. 2013, 49, 5319-5321.
Vader, P. et al, Disulfide-Based Poly(Amido Amine)s for siRNA Delivery: Effects of Structure on siRNA Complexation, Cellular Uptake, Gene Silencing and Toxicity. Pharmaceut. Res. 2011, 28, 1013-1022.
Wyman, T. et al, Design, Synthesis, and Characterization of a Cationic Peptide That Binds to Nucleic Acids and Permeabilizes Bilayers. Biochemistry 1997, 36, 3008-3017.
Mok, H. et al, Self-Crosslinked and Reducible Fusogenic Peptides for Intracellular Delivery of siRNA. Biopolymers 2008, 89, 881-888.
Sunshine, J. et al, Effects of Base Polymer Hydrophobicity and End-Group Modification on Polymeric Gene Delivery. Biomacromolecules 2011, 12, 3592-3600.
Lopez-Bertoni et al, Bioreducible Polymeric Nanoparticles Containing Multiplexed Cancer Stem Cell Regulating miRNAs Inhibit Glioblastoma Growth and Prolong Survival. Nano Lett. 2018;18:4086-94.
Binder. Functional MRI is a valid noninvasive alternative to Wada testing. Epilepsy Behav. Feb. 2011;20(2):214-22.
Papanicolaou et al., Is it time to replace the Wada test and put awake craniotomy to sleep? Epilepsia. May 2014;55(5):629-632.
Rapoport et al., Focused ultrasound-mediated drug delivery to pancreatic cancer in a mouse model. J Ther Ultrasound. Jul. 1, 2013:1:11.
Rapoport. Drug-Loaded Perfluorocarbon Nanodroplets for Ultrasound-Mediated Drug Delivery. Adv Exp Med Biol. 2016:880:221-41.
Remington: The Science and Practice of Pharmacy. Lippincott Williams & Wilkins., (2005), ed. 21. 14 pages.
Timbie et al., Drug and gene delivery across the blood-brain barrier with focused ultrasound. J Control Release. Dec. 10, 2015:219:61-75.

* cited by examiner

Radical photoinitiator and UV light

BIOREDUCIBLE POLY (BETA-AMINO ESTER)S FOR SIRNA DELIVERY

CROSS-REFERENCE TO RELATED APPLICATIONS

This application is a 35 U.S.C. § 371 National Stage Entry of International Application No. PCT/US2013/066901 having an international filing date of Oct. 25, 2013, which claims the benefit of U.S. Provisional Application Nos. 61/718,536, filed Oct. 25, 2012, 61/860,638, filed Jul. 31, 2013, and 61/883,376, filed Sep. 27, 2013, each of which is incorporated herein by reference in its entirety.

FEDERALLY SPONSORED RESEARCH OR DEVELOPMENT

This invention was made with government support under 1R01EB016721 and R21CA152473 awarded by the National Institutes of Health (NIH). The government has certain rights in the invention.

BACKGROUND

RNA interference (RNAi) is a naturally occurring cellular mechanism that ultimately results in sequence-specific gene knockdown and can be externally induced by intracellular delivery of short interfering RNA (siRNA). Fire, A., et al., *Nature* 1998, 391, (6669), 806-811. Targeted gene knockdown via siRNA delivery has the potential for treating diseases caused by aberrant gene expression. Wu, W., et al., *Int. J. Cancer* 2007, 120, (5), 953-60; Yadav, S., et al., *Cancer Chemother. Pharmacol.* 2009, 63, (4), 711-22. Intracellular siRNA delivery, however, remains a challenging obstacle.

Promising siRNA delivery strategies have been suggested that employ lipid-based, Akinc, A., et al., *Nat. Biotechnol.* 2008, 26, (5), 561-569; Semple, S. C., et al., *Nat. Biotechnol.* 2010, 28, (2), 172-6, inorganic, Derfus, A. M., et al., *Bioconjugate Chem.* 2007, 18, (5), 1391-1396; Elbakry, A., et al., *Nano Lett.* 2009, 9, (5), 2059-2064; Kakizawa, Y., et al., *J. Control. Release* 2006, 111, (3), 368-370, or polymeric materials, Breunig, M., et al., *J. Control. Release* 2008, 130, (1), 57-63; Jeong, J. H., et al., *Biomaterials* 2007, 28, (10), 1912-1917; Matsumoto, S., et al., *Biomacromolecules* 2009, 10, (1), 119-127, similar to those materials designed for DNA delivery.

Accordingly, certain siRNA delivery material design parameters can be addressed using the same materials found to effectively deliver DNA. Cationic polymers with high buffering capacities, such as poly(ethyleneimine) (PEI) promote nucleic acid compaction and protection, cellular internalization, and endosomal escape. Boussif, O., et al., *Proc. Natd. Acad. Sci.* 1995, 92, (16), 7297-7301. Further, polymer degradability, such as that afforded by hydrolytically cleavable poly(β-amino ester)s (PBAE)s, results in cargo release superior to nondegrading PEI. Lynn, D. M.; Langer, R. *J. Am. Chem. Soc.* 2000, 122, (44), 10761-10768.

SUMMARY

In some aspects, the presently disclosed subject matter includes a compound of formula (I) or formula (II):

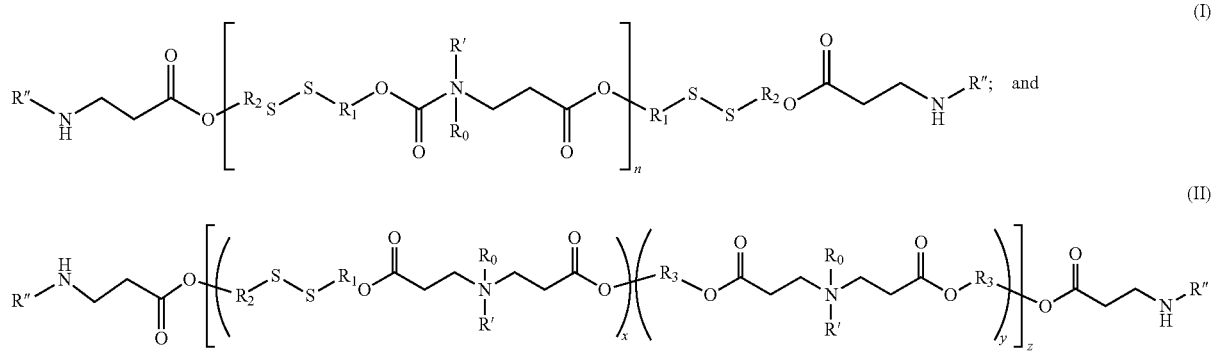

wherein: n is an integer from 1 to 10,000; X and Y are integers, which can be represented by a ratio X:Y:Z is an integer from 1 to 10,000; $R_0$ can be present or absent and when present the compound of formula (I) further comprises a counter ion selected from the group consisting of chloride, fluoride, bromide, iodide, sulfate, nitrate, fumarate, acetate, carbonate, stearate, laurate, and oleate; $R_1$ and $R_2$ can be the same or different and are each independently a $C_1$-$C_{30}$ alkyl chain; each $R_3$ is a $C_3$-$C_8$ linear or branched alkyl chain; R' is a substituted side chain comprising a functional group that facilitates solubility in water and/or hydrogen bonding; each R" can be the same or different and comprise a non-reducible end group or reducible end group; and pharmaceutically acceptable salts thereof.

In some aspects, the presently disclosed compounds of formula (I) and formula (II) are useful for delivering a therapeutic agent to a cell, a specific cell line, a tissue, or an organism. The therapeutic agent can include a gene, DNA, RNA, siRNA, miRNA, isRNA, agRNA, smRNA, a nucleic acid, a peptide, a protein, a chemotherapeutic agent, a hydrophobic drug, and a small molecule drug.

In other aspects, the presently disclosed subject matter provides a method of treating a disease or condition, the method comprising administering to a subject in need of treatment thereof, a compound of formula (I) or formula (II) further comprising a therapeutic agent effective for treating the disease or condition. Diseases that can be treated by the presently disclosed methods include, but are not limited to, a cancer, including brain cancer (including Glioblastoma Multiforme), lung cancer, breast cancer, prostate cancer, colorectal cancer, and other cancers; cardiovascular diseases; infectious diseases; and ophthalmic diseases, including age-related macular degeneration.

In further aspects, the presently disclosed subject matter includes an in vitro kit comprising a compound of formula (I) or formula (II). In yet further aspects, the presently disclosed subject matter includes a biomedical device, such as a stent or a stent-like device, comprising a compound of formula (I) or formula (II) or an article coated with one or more compounds of formula (I) or formula (II) alone or in combination with one or more commercially available and/or FDA-approved polyelectrolytes.

In yet further aspects, the presently disclosed subject matter provides a method for forming a tissue scaffolding structure, the method comprising implanting into a subject a polymeric matrix comprising a compound of formula (I) or formula (II). The implant can include one or more cells selected from the group consisting of hepatocytes, pancreatic islet cells, fibroblasts, chondrocytes, osteoblasts, exocrine cells, cells of intestinal origin, bile duct cells, parathyroid cells, thyroid cells, cells of the adrenal-hypothalamic-pituitary axis, heart muscle cells, epithelial cells, kidney tubular cells, kidney basement cells, kidney tubular cells, kidney basement membrane cells, nerve cells, blood vessel cells, cells forming bone and cartilage, smooth and skeletal muscle cells, cells from the retina and other parts of the eye, stem cells, induced pluripotent stem cells, and three-dimensional organoids.

In additional aspects, the presently disclosed subject matter provides a nanoparticle or microparticle comprising a compound of formula (I) or formula (II) and methods of using and storing such nanoparticles or microparticles.

In still other aspects, the presently disclosed subject matter provides a method for silencing a gene, the method comprising contacting a therapeutic agent with a compound of formula (I) or formula (II) to form one or more particles comprising the therapeutic agent and the compound, contacting the one or more particles with a cell, wherein the one or more particles enter the cell, wherein the therapeutic agent is released from the one or more particles and binds to a nucleic acid in the cell, thereby silencing a gene.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
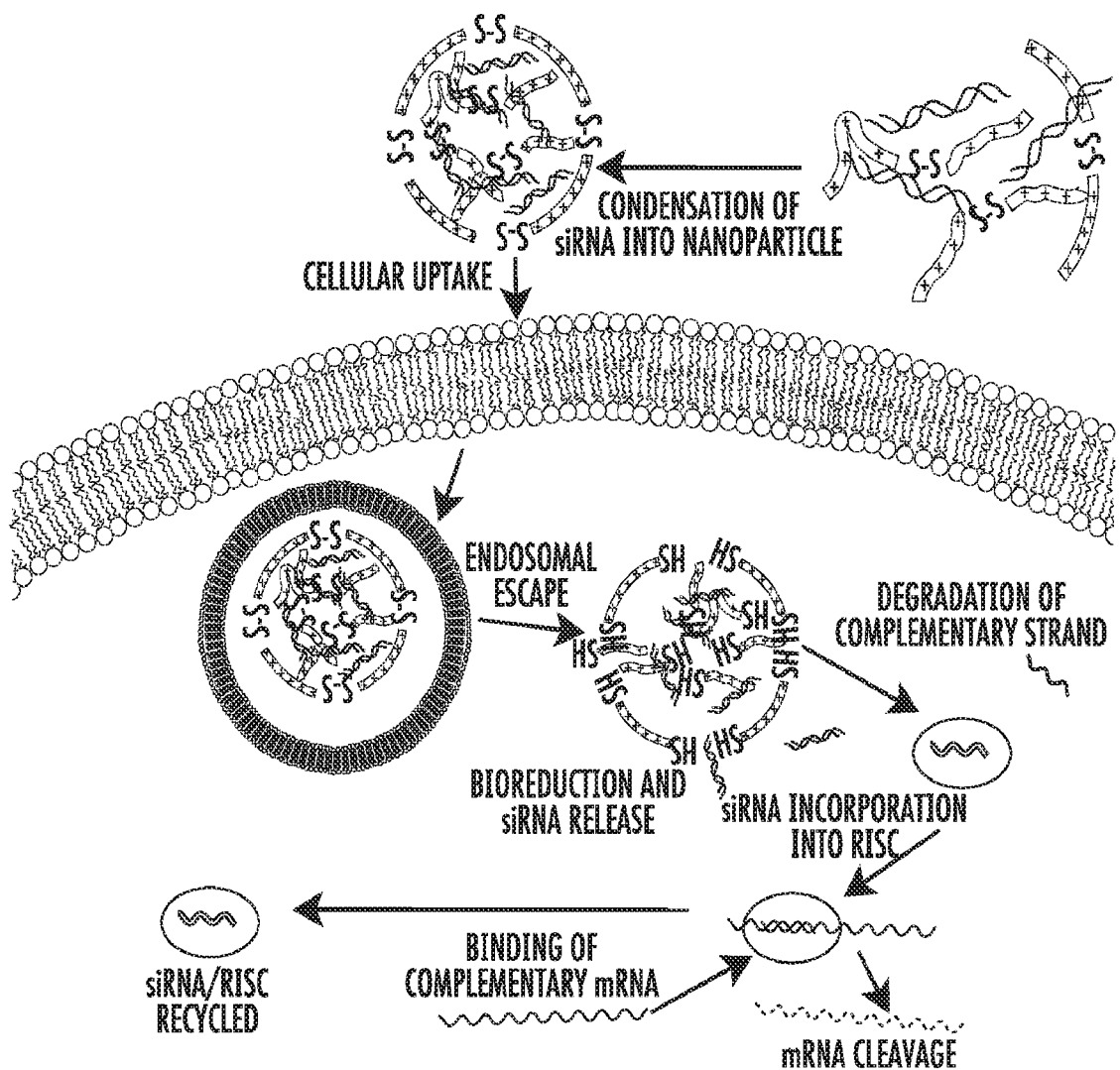
Figure 2:
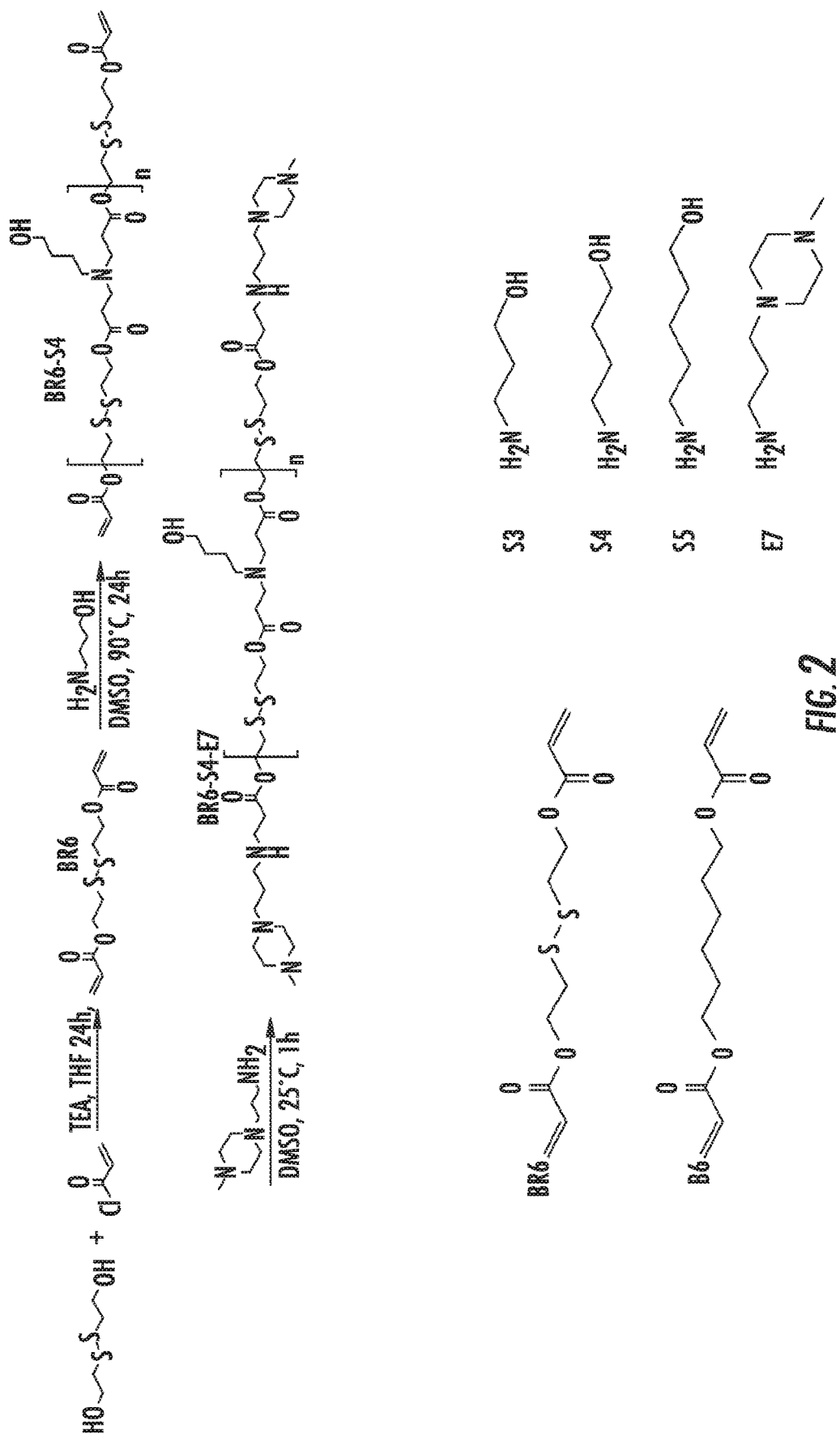
Figure 3:
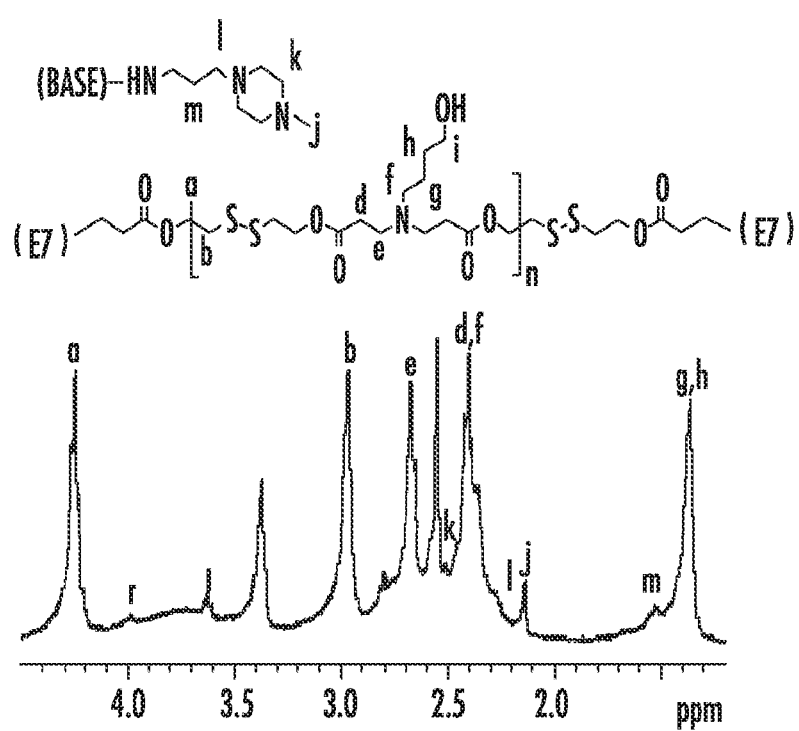
Figure 4:
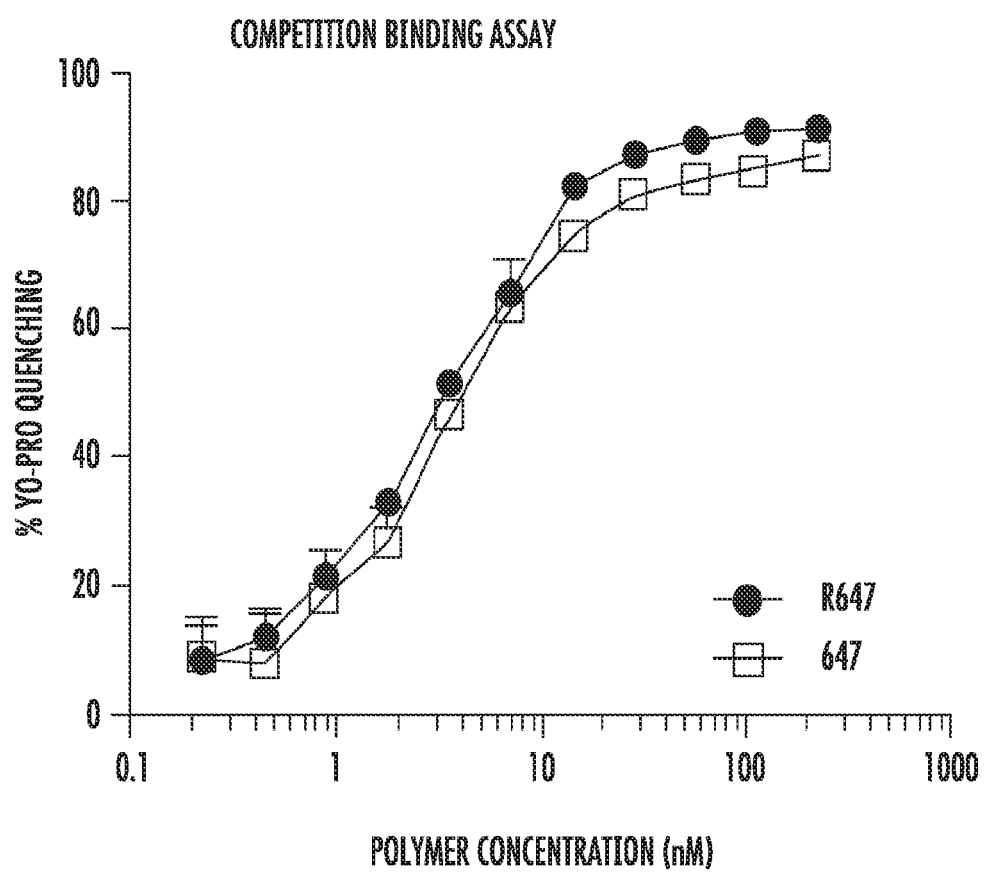
Figure 5:
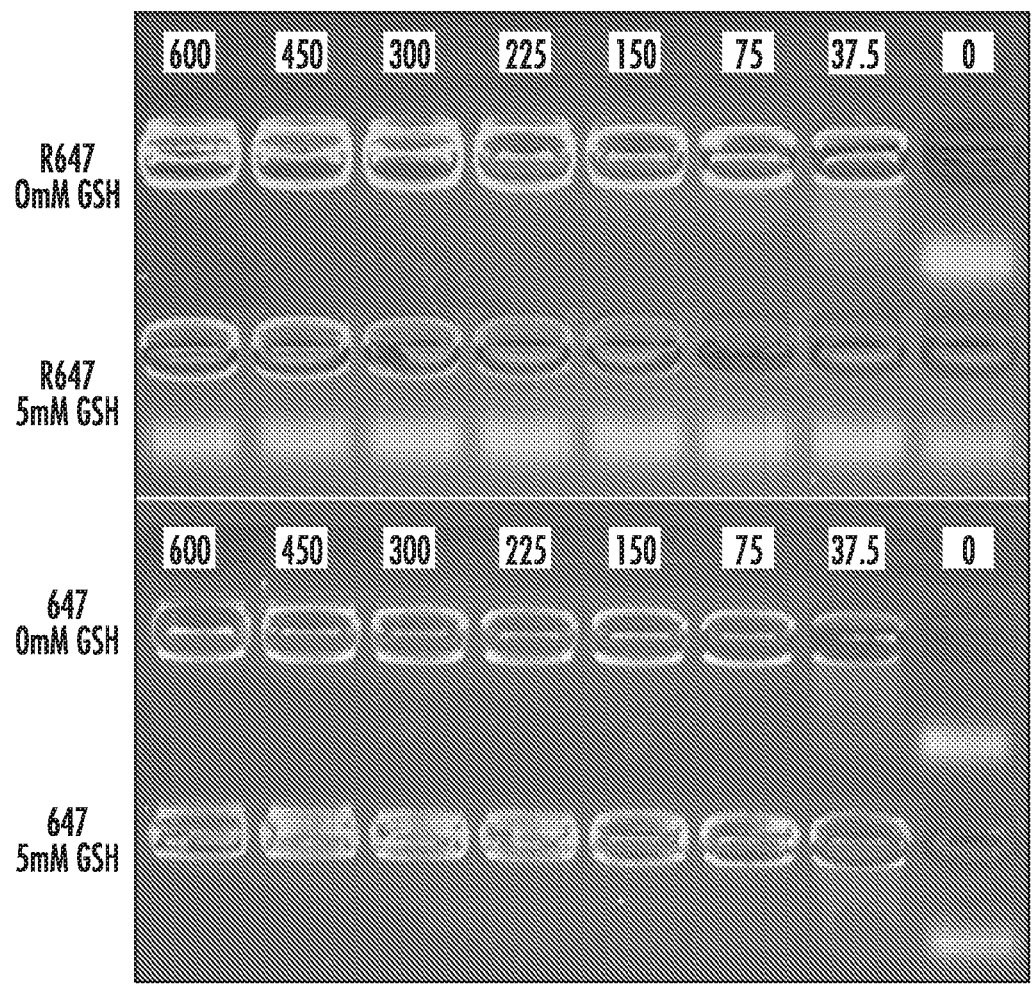
Figure 6:
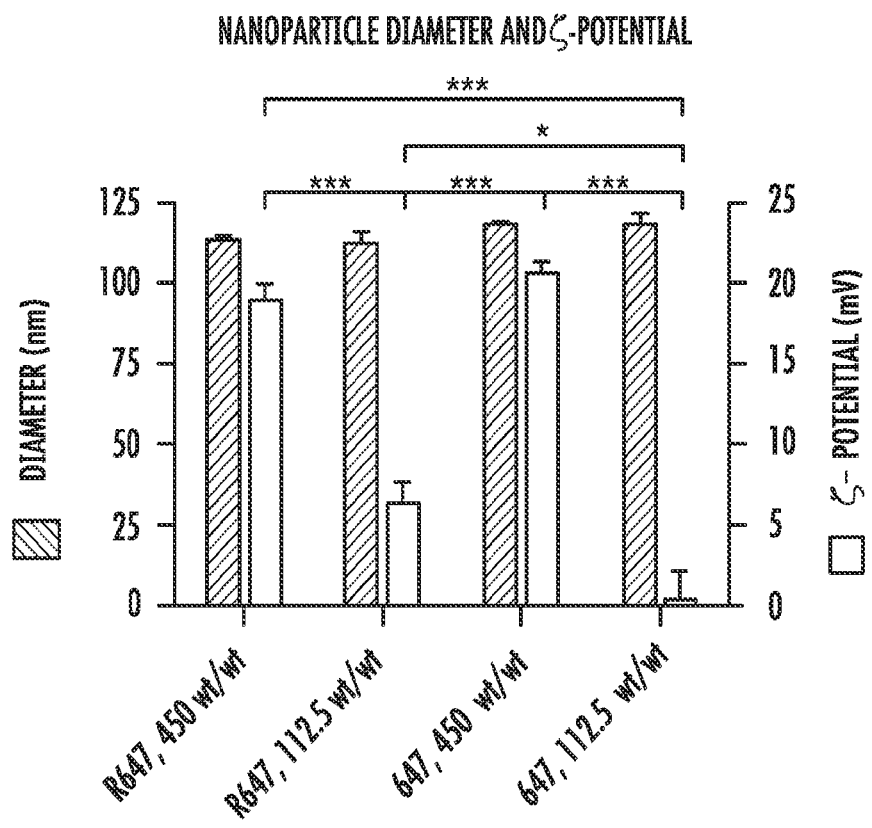
Figure 7:
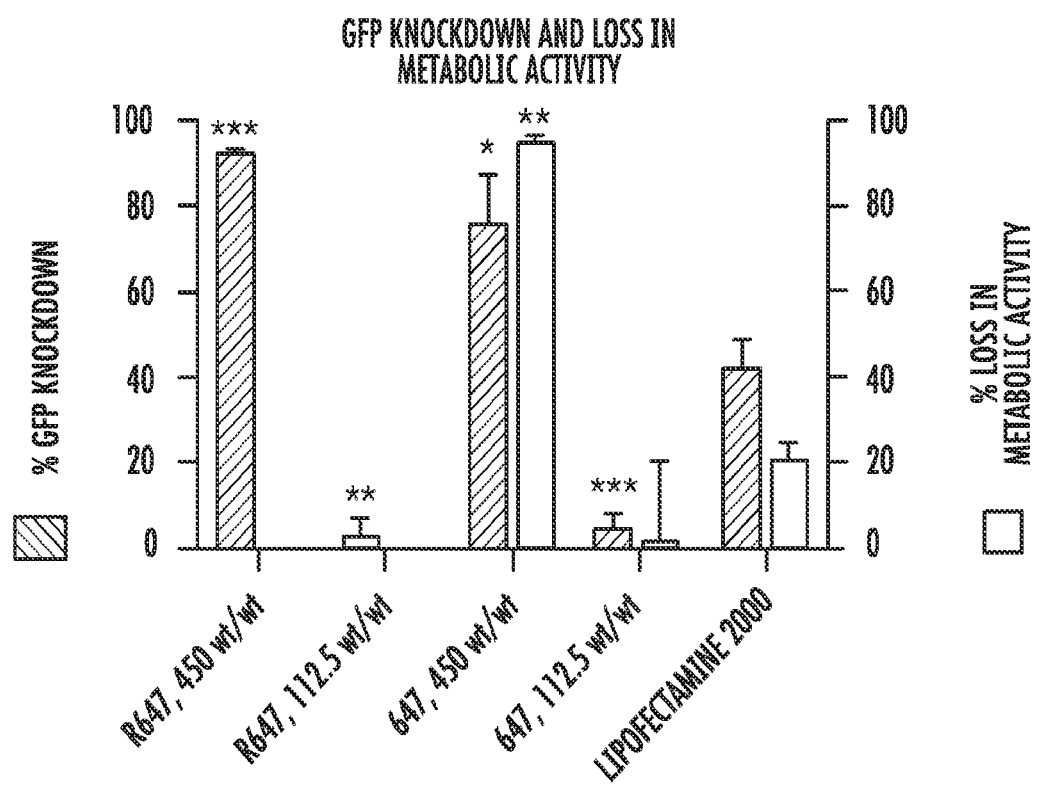
Figure 8:
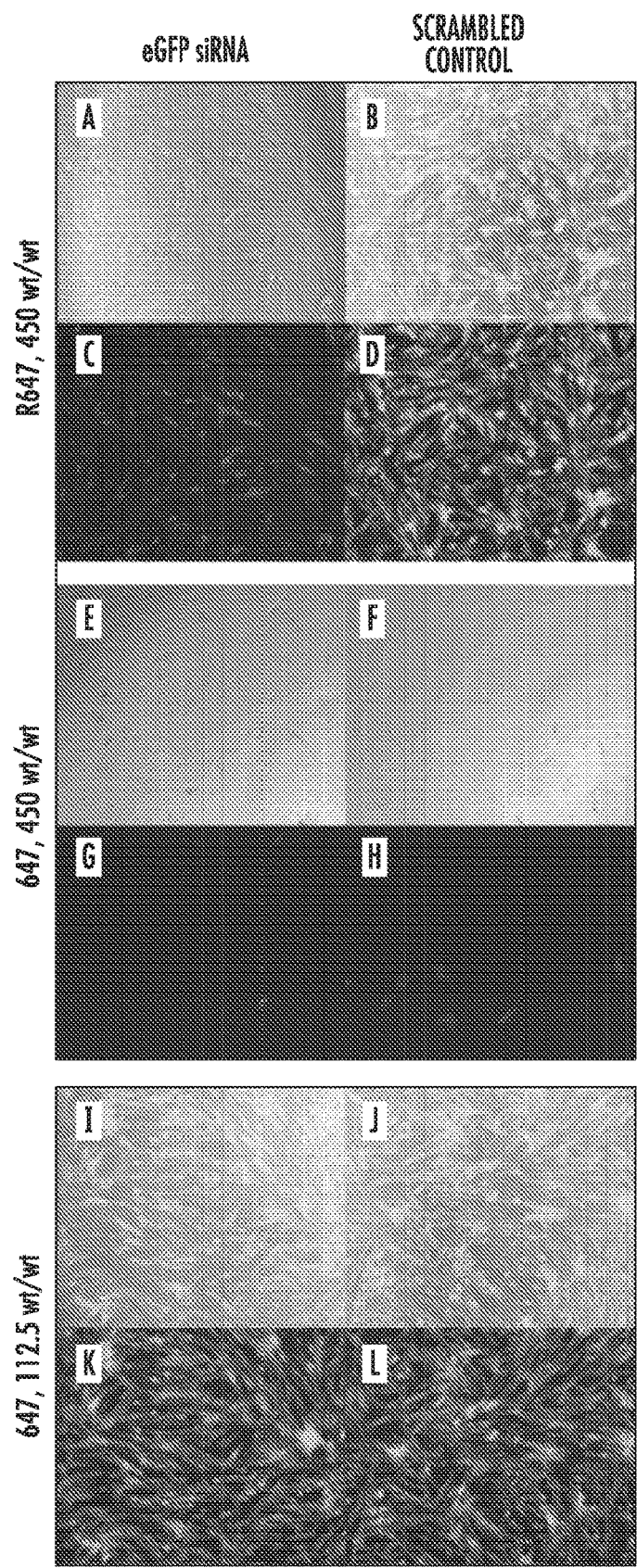
Figure 9:
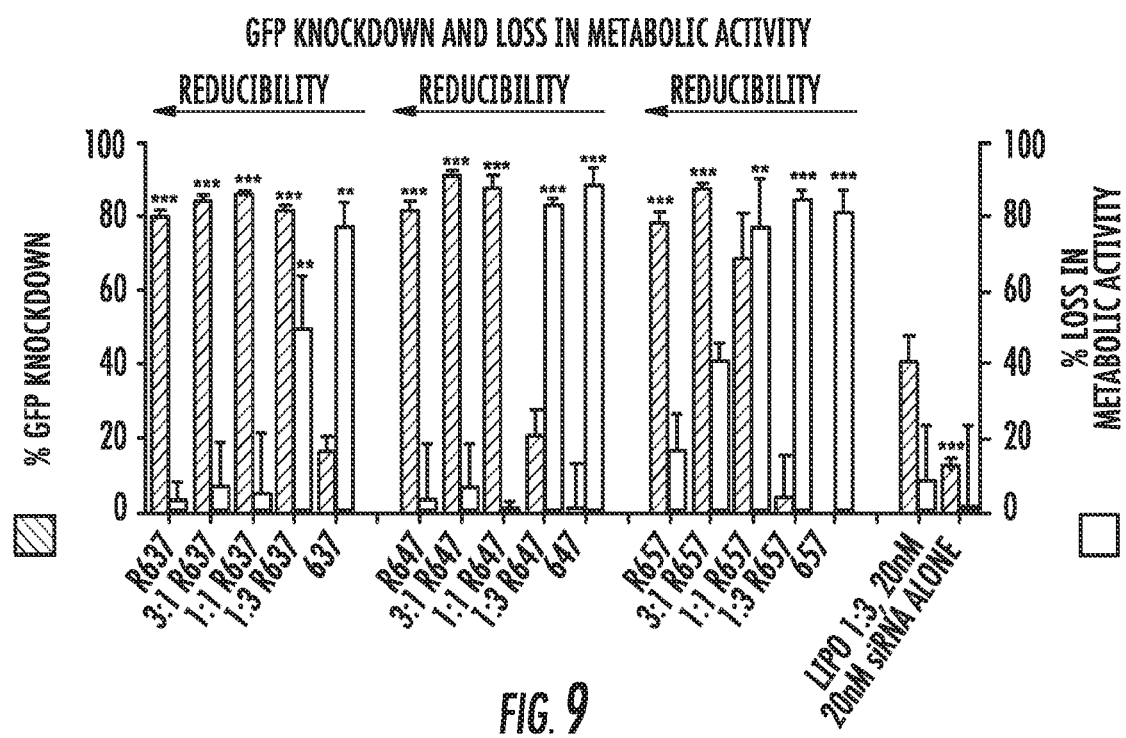
Figure 11:
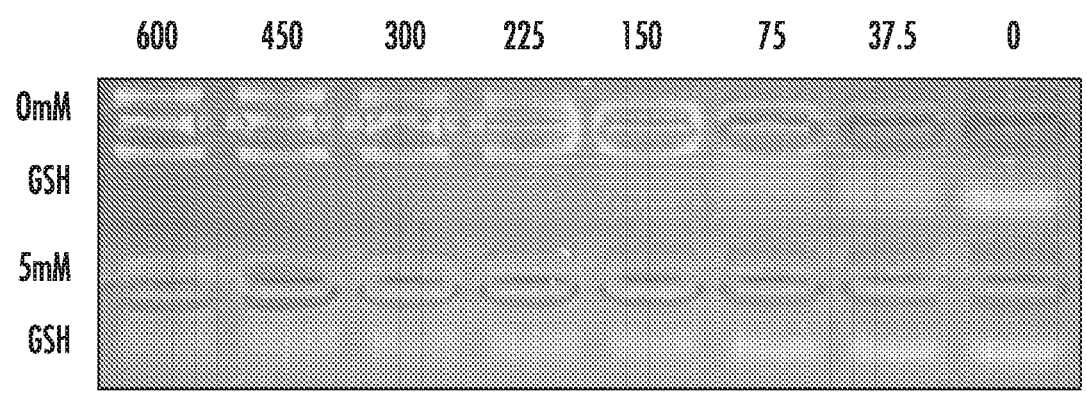
Figure 14:
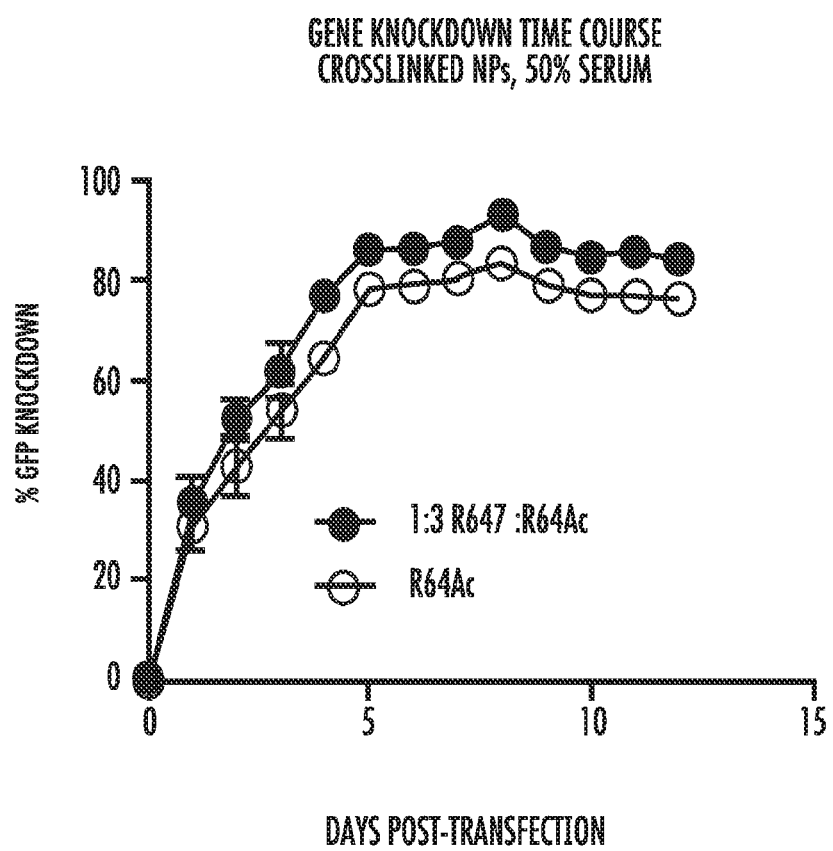
Figure 15:
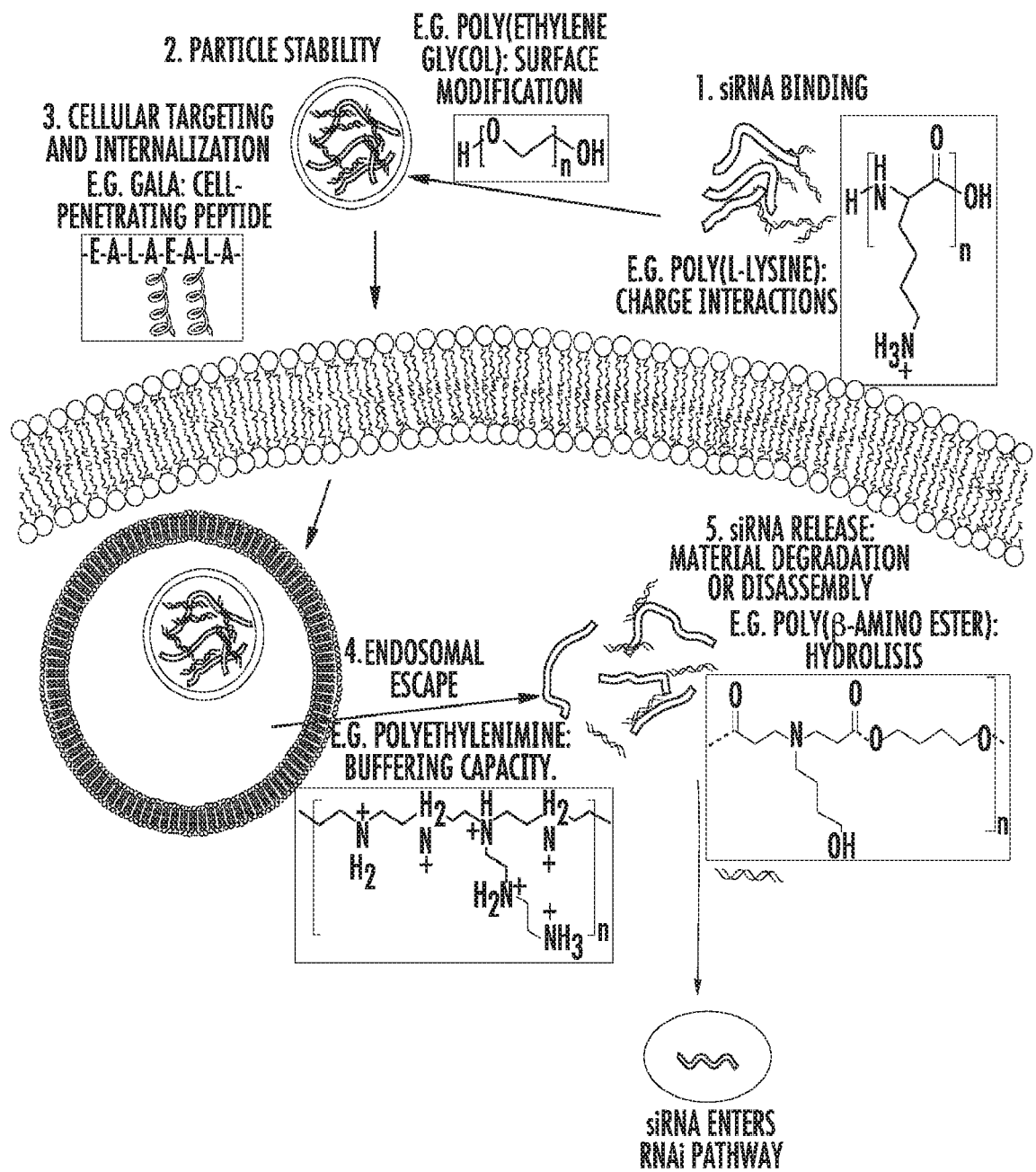
Figure 16:
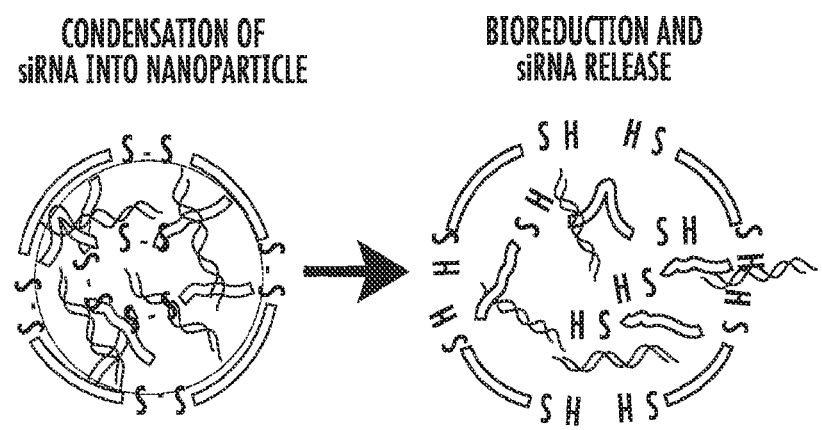
Figure 17:
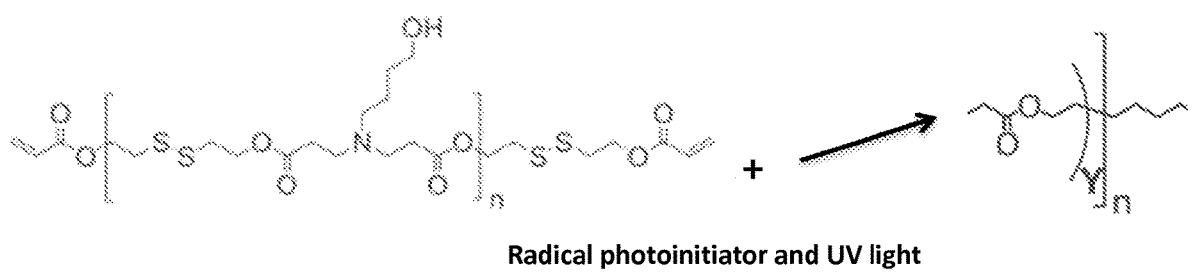
Figure 18:
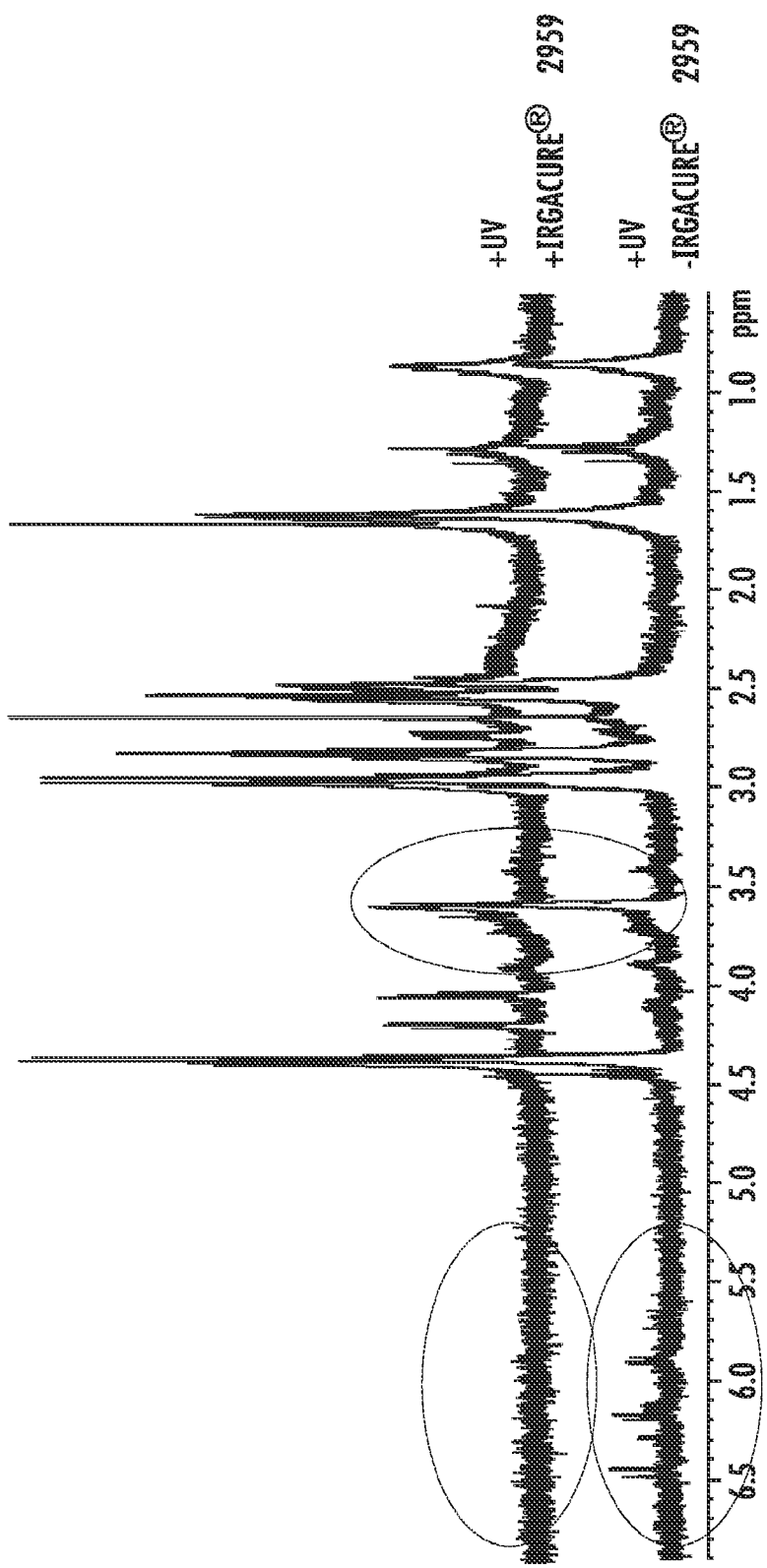
Figure 19:
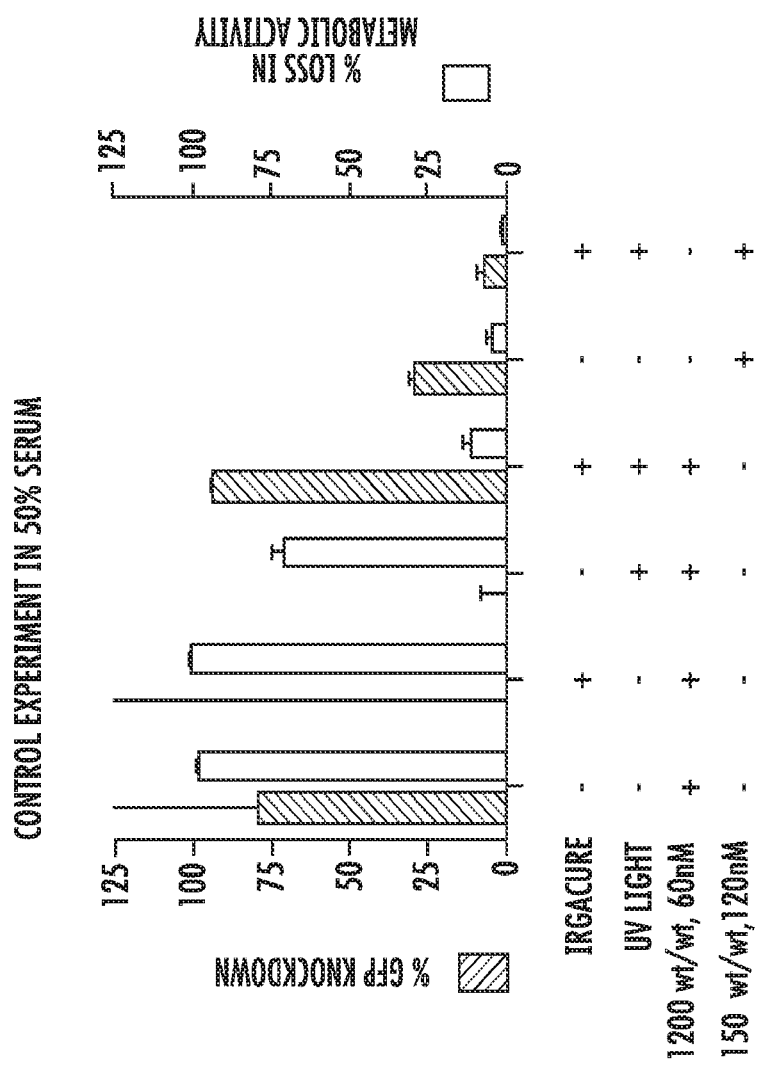
Figure 20:
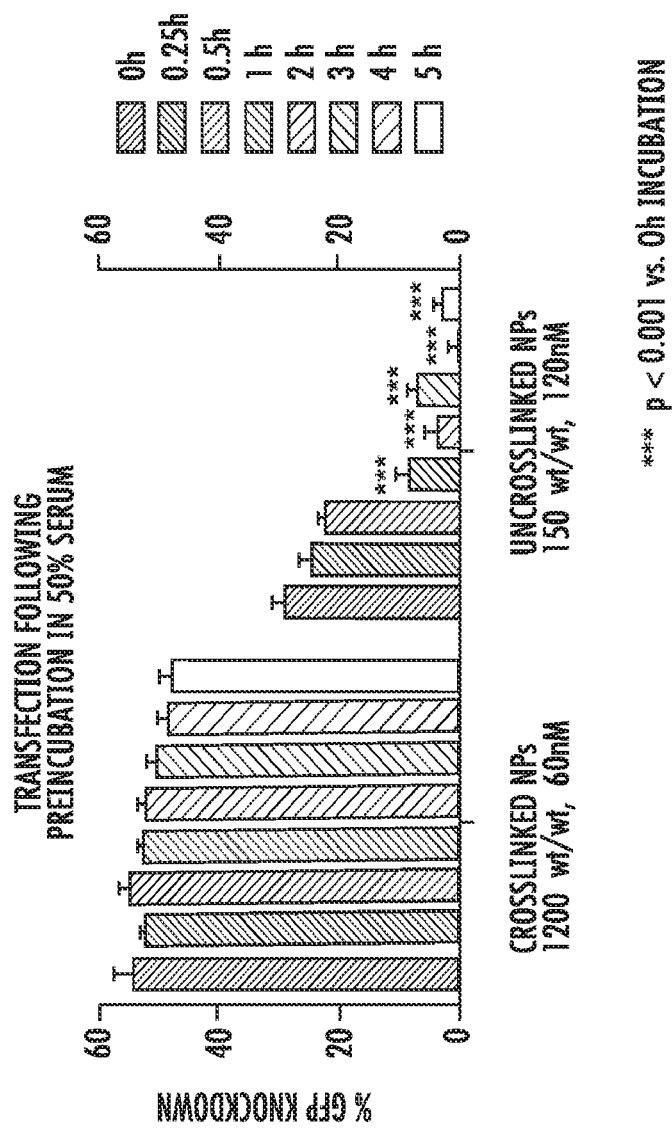

Having thus described the presently disclosed subject matter in general terms, reference will now be made to the accompanying Figures, which are not necessarily drawn to scale, and wherein:

FIG. 1 is a representative scheme of the mechanism by which polymeric siRNA is delivered into a cell and gene silencing of a specific mRNA occurs;

FIG. 2 is a representative synthesis scheme of R647;

FIG. 3 shows an $H^1$-NMR spectrum of R647 with labeled peaks correlating to protons along the R647 structure;

FIG. 4 shows a competition binding assay of R647 and 647. Polymer to siRNA binding strength was assessed by quenching of YO-PRO®-1 Iodide fluorescence over increasing polymer concentrations;

FIG. 5 shows a gel retention assay. Gel electrophoresis image of siRNA complexed with R647 (top) or 647 (bottom) in the absence (0 mM) or presence (5 mM) of GSH. Numbers above each well indicate the polymer to siRNA weight ratio;

FIG. 6 shows representative nanoparticle size and surface charge; Nanoparticle diameter and ζ-potential of particles formed using either R647 or 647 at either 450 wt/wt or 112.5 wt/wt. Nanoparticle diameter was measured using NTA. ζ-potential was measured using DLS. Nanoparticle diameters of all samples were not significantly different ($P > 0.05$);

FIG. 7 shows Day 9 gene knockdown and loss in metabolic activity of GFP+GBM 319 cells transfected with R647 and 647. Transfections were completed at either 450 or 112.5 wt/wt with 26.7 nM siRNA targeted against GFP. LIPOFECTAMINE™ 2000 positive control with 26.7 nM siRNA is used as the statistical control;

FIG. 8 shows fluorescence and brightfield microscopy images of transfected cells at day 9 post-transfection. Brightfield images of R647, 450 wt/wt treated cells (A-B) and 647, 112.5 wt/wt treated cells (I-J) show viable cells while 647, 450 wt/wt treated cells (E-F) show significant toxicity. Fluorescence images of R647, 450 wt/wt treated cells show significantly less GFP expression in GFP siRNA treated cells (C) versus cells treated with the same formulation using scrambled control siRNA (D). Fluorescence images of 647, 112.5 wt/wt treated cells show similar GFP expression in both GFP siRNA (K) and scrambled control treated cells (L);

FIG. 9 demonstrates gene knockdown and toxicity of polymers with varying bioreducibility and hydrophobicity. Results shown include day one loss in metabolic activity and day 9 gene knockdown of GFP+ GBM 319 cells transfected with all polymers using 180 μg/mL polymer and 20 nM siRNA targeting GFP, normalized to cells treated with the same NP formulation using scrambled control RNA. LIPOFECTAMINE™ 2000 is used as the control for statistical comparisons by one-way ANOVA with Dunnett's post-tests (*=$p<0.05$, =$p<0.01$, *=$p<0.001$);

FIGS. 10A-10E show GFP knockdown and loss in metabolic activity results of GFP+ GBM 319 cells transfected with various formulations of 1:1 R647 siRNA nanoparticles. All knockdown values are normalized to scrambled control RNA: (A) Transfection results using 180 μg/mL polymer with siRNA doses ranging from 1-160 nM. The LIPOFECTAMINE™ 2000 control shown used 20 nM siRNA; (B) Transfection results using 20 nM siRNA with polymer concentrations ranging from 11.25-360 μg/mL; (C) Correlation of knockdown efficiency and varying siRNA doses with polymer concentration fixed at 180 μg/mL fitted to a semi logarithmic line; (D) Correlation of knockdown efficiency and varying polymer concentrations with siRNA concentration fixed at 20 nM fitted to a linear regression; and (E) Brightfield (top) and fluorescence (bottom) images of GFP+ GBM cells treated with 1:1 R647 at 180 μg/mL and 20 nM of either siRNA targeting GFP (left) or scrambled control RNA (right). LIPOFECTAMINE™ 2000 is used as the control for statistical comparisons by one-way ANOVA with Dunnett's post-tests (*=$p<0.05$, =$p<0.01$, *=$p<0.001$);

FIG. 11 is a gel retention assay of 1:1 R647 particles formed at varying wt/wts and incubated for 15 min at room temperature in the absence (top) or presence (bottom) of 5 mM GSH. Columns above each well indicate polymer to siRNA wt/wt ratio;

FIGS. 12A-12D show characterization of nanoparticle size, zeta potential, concentration, and loading of nanoparticles synthesized with 180 μg/mL 1:1 R647 and varying siRNA doses (A,C) or with 20 nM siRNA and varying polymer concentrations (B,D). Size and concentration were measured by NTA, zeta potential was measured using DLS, and siRNA loading was calculated from concentration: (A) Nanoparticle size positively correlates with siRNA dose on a semi logarithmic scale, while zeta potential does not change; (B) Nanoparticle size and zeta potential do not tightly correlate with polymer concentration; (C) Nanoparticle concentration remains consistent despite changing siRNA dose, while siRNA loading increases linearly; and (D) Nanoparticle concentration linearly increases with polymer concentration resulting in exponential decay of siRNA loading with increasing polymer concentration. This plot excluded siRNA loading values for polymer concentrations of 11.25 μg/mL and 22.5 μg/mL since the gel retention assay showed that these formulations did not completely bind siRNA;

FIGS. 13A and 13B show characterization of nanoparticle size distribution. (A) TEM image of nanoparticles made with 1:1 R647 at 180 μg/mL with 20 nM siRNA; and (B) Nanoparticle size distribution of 1:1 R647 at 180 μg/mL and either 20 nM siRNA or 0 nM siRNA as measured by NTA;

FIG. 14 demonstrates the efficacy of cross-linked bioreducible polymeric nanoparticles for siRNA delivery;

FIG. 15 is a schematic representing barriers that siRNA faces during intracellular delivery. Representative biomaterials that are able to overcome these barriers are shown, along with a particular strategy employed by that material;

FIG. 16 is a schematic showing the condensation of siRNA into a presently disclosed nanoparticle and the bioreduction of the nanoparticle and subsequent siRNA release;

FIG. 17 shows the production of crosslinked nanoparticles by using radical photoinitiator and UV light are used to produce crosslinked nanoparticles;

FIG. 18 provides NMR spectra confirming the crosslinking of the presently disclosed nanoparticles;

FIG. 19 shows that the presently disclosed crosslinked nanoparticles exhibit effective in vitro siRNA delivery in 50% serum; and FIG. 20 shows the efficacy of the presently disclosed crosslinked nanoparticles after being preincubated in 50% serum prior to transfection.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Bioreducible Poly (β-Amino Ester)S for siRNA Delivery

RNA interference (RNAi)-induced gene knockdown is a naturally occurring cellular pathway that targets mRNA transcripts for cleavage in a sequence-specific manner (Fire et al., 1998). This pathway can be exploited to target specific genes and alter cellular behavior with the delivery of short interfering RNA (siRNA) complementary to the mRNA transcript of the gene of interest (Kuwabara and Coulson, 2000). The therapeutic potential of siRNA cannot be realized, however, without efficient delivery to its site of action in the cytoplasm. A promising approach lies in polymeric delivery vehicles, such as poly(β-amino)esters (PBAEs), which spontaneously form nanoparticles with nucleic acids when in an aqueous environment (Green et al., 2008). This electrostatically driven interaction allows infinite flexibility in terms of nucleic acid sequence and therefore has a wide range of potential disease targets.

PBAE-nucleic acid nanoparticles allow release by hydrolytic degradation of esters along the polymer backbone on the time scale of several hours to a few days (Lynn, 2000; Sunshine et al, 2012). This release mechanism, however, limits control over where the release will occur. To specifically target release to the cytoplasm, a novel linear PBAE polymer with disulfide bonds along the polymer backbone has been synthesized. Disulfide bonds can be degraded reductively in the human body via glutathione (GSH), which is present predominantly in the cytosol of human tissues at concentrations ranging from about 1 mM to about 8 mM, which is three orders of magnitude greater than the concentration in blood serum (about 5 μM to about 50 μM) (Griffith, 1999). Without wishing to be bound to any one particular theory, it was thought that a reducible, disulfide-containing analog of a previously established PBAE formulation would promote enhanced siRNA-mediated gene knockdown. The goal was to create reducible nanoparticles that would be as physically identical as possible to their non-reducible analogs when in an extracellular environment, but would then efficiently release siRNA when in a reducing cytoplasmic environment.

The presently disclosed subject matter provides efficient delivery vehicles to enable controlled gene knockdown by siRNA. Referring now to FIG. 1, a representative pathway of siRNA gene silencing using the presently disclosed compounds of formula (I) or formula (II) is shown. Again, without wishing to be bound to any one particular theory, in this pathway, condensation of siRNA into the presently disclosed nanoparticles occurs, a cell takes up the nanoparticles combined with the siRNA, and endosomes comprising the siRNA nanoparticles form. In the reducing cytoplasmic environment, the nanoparticles are released from the endosome and the siRNAs are released from the nanoparticles. Subsequently, the siRNA is incorporated into a RNA-induced silencing complex (RISC), which uses the siRNA as a template for recognizing complementary mRNA. When the RISC finds a complementary strand, it activates the RNase enzyme, which cleaves the complementary mRNA. By this pathway, gene silencing or gene knockdown of a specific mRNA can occur. The presently disclosed compounds of formula (I) or formula (II) provide near-complete or complete knockdown of specific genes with little or no toxicity to the cells.

Scheme 1, shown immediately herein below, and FIG. 1 provide a representative example of the synthesis of the presently disclosed compound R647, a compound used as a delivery vehicle to enable controlled gene knockdown by siRNA.

Scheme 1. Synthesis of R647.

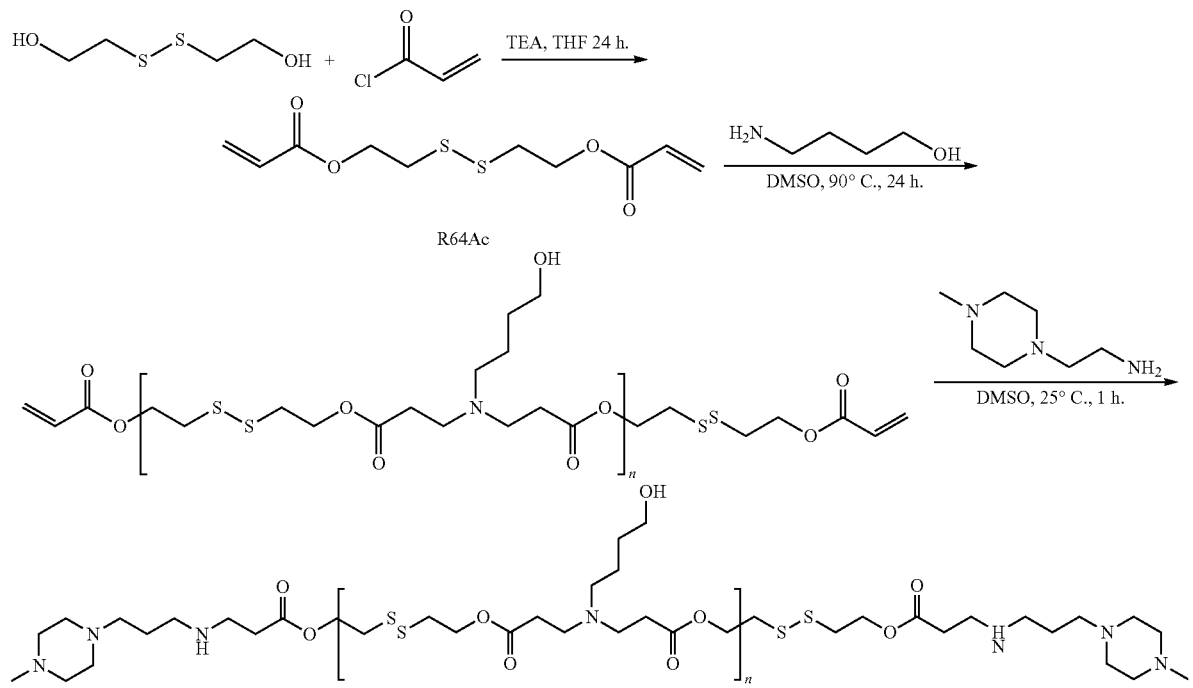

As shown in Scheme 1, one way to synthesize the presently disclosed materials is by the conjugate addition of amine-containing molecules to acrylates or acrylamides. This reaction can be done neat or in a solvent, such as DMSO or THF. Reactions can take place at a temperature ranging from about room temperature up to about 90° C. and can have a duration from about a few hours to about a few weeks. The presently disclosed methods can be used to create linear or branched polymers.

Accordingly, in some embodiments, the presently disclosed subject matter provides a compound of formula (I):

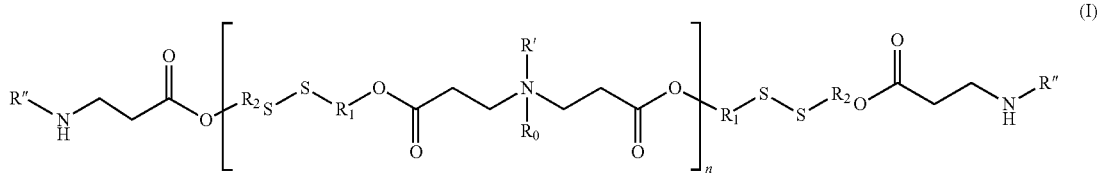

wherein: n is an integer from 1 to 10,000; $R_0$ can be present or absent and when present the compound of formula (I) further comprises a counter ion selected from the group consisting of chloride, fluoride, bromide, iodide, sulfate, nitrate, fumarate, acetate, carbonate, stearate, laurate, and oleate; $R_1$ and $R_2$ can be the same or different and are each independently a $C_1$-$C_{30}$ alkyl chain; R' is a substituted side chain comprising a functional group that facilitates solubility in water and/or hydrogen bonding; each R" can be the same or different and comprise a non-reducible end group or reducible end group; and pharmaceutically acceptable salts thereof.

In some embodiments of the compound of formula (I), n is an integer from 1 to 10,000; in other embodiments, n is an integer from 1 to 1,000; in other embodiments, n is an integer from 1 to 100; in other embodiments, n is an integer from 1 to 30; in other embodiments, n is an integer from 5 to 20; in other embodiments, n is an integer from 10 to 15; and in other embodiments, n is an integer from 1 to 10.

In some embodiments, the molecular weight (MW) of compounds of formula (I) has a range from about 1 kDa to about 5 kDa, in other embodiments, the MW has a range from about 5 kDa to about 10 kDa, in other embodiments the MW has a range from about 10 kDa to about 15 kDa, in other embodiments, the MW has a range from about 15 kDa to about 25 kDa, in other embodiments, the MW has a range from about 25 kDa to about 50 kDa, and in other embodiments, the MW has a range from about 50 kDa to about 100 kDa. In other embodiments, the polymer forms a network, gel, and/or scaffold of apparent molecular weight greater than 100 kDa.

In compounds of formula (I), the endcapping group structures, i.e., the R" groups are distinct and separate from the backbone structures ($R_1$ and $R_2$ groups), and the side chain structures (R' group).

The compounds of formula (I) have at least one or more reducible or degradable linkages. Representative reducible or degradable linkages include, but are not limited to:

Enzymatic Degradation

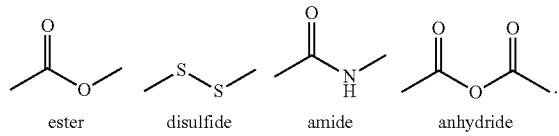

ester      disulfide      amide      anhydride

The compounds of formula (I) include at least a disulfide linkage. One or more of R' and R" also can include a reducible linkage. In some embodiments of compounds of formula (I), one or more of the following additional modes of degradation also are present: (a) the R' and R" substituent groups that make up the presently disclosed polymers degrade via different biodegradation mechanisms within the same polymer. These biodegradation mechanisms can include hydrolytic, bioreducible, enzymatic, and/or other modes of degradation; (b) the endcapping groups of the polymer include a minority structure that differs from the majority structure that comprises most of the polymer backbone; and (c) in several embodiments, the side chain molecules (R') contain hydroxyl (OH)/alcohol groups.

Accordingly, in some embodiments: (a) the backbone is bioreducible and the endcapping groups degrade hydrolytically; (b) the backbone degrades hydrolytically and the endcapping groups are bioreducible; (c) hydrolytically degradable oligomers are cross-linked with a bioreducible cross-linker; (d) bioreducible oligomers form block copolymers with hydrolytically degradable oligomers; and (e) the endcapping group/minority structure comprises an amino acid or chain of amino acids, whereas the backbone degrades hydrolytically and/or is bioreducible.

The synthesis and characteristics of certain bioreducible and/or degradable polymers are disclosed in WO/2010/132879 for MULTICOMPONENT DEGRADABLE CATIONIC POLYMERS, to Green et al., published Nov. 18, 2010, and U.S. Patent Application Publication No. 20120128782 for MULTICOMPONENT DEGRADABLE CATIONIC POLYMERS, to Green et al., published May 24, 2012, each of which is incorporated herein by reference in its entirety, with the proviso that any compounds included therein are excluded from the presently disclosed subject matter.

Representative monomers used to synthesize the presently disclosed cationic polymers include, but are not limited to, those provided immediately herein below. The presently disclosed subject matter is not limited to the representative monomers disclosed herein, but also includes other structures that one skilled in the art could use to create similar biphasic degrading cationic polymers.

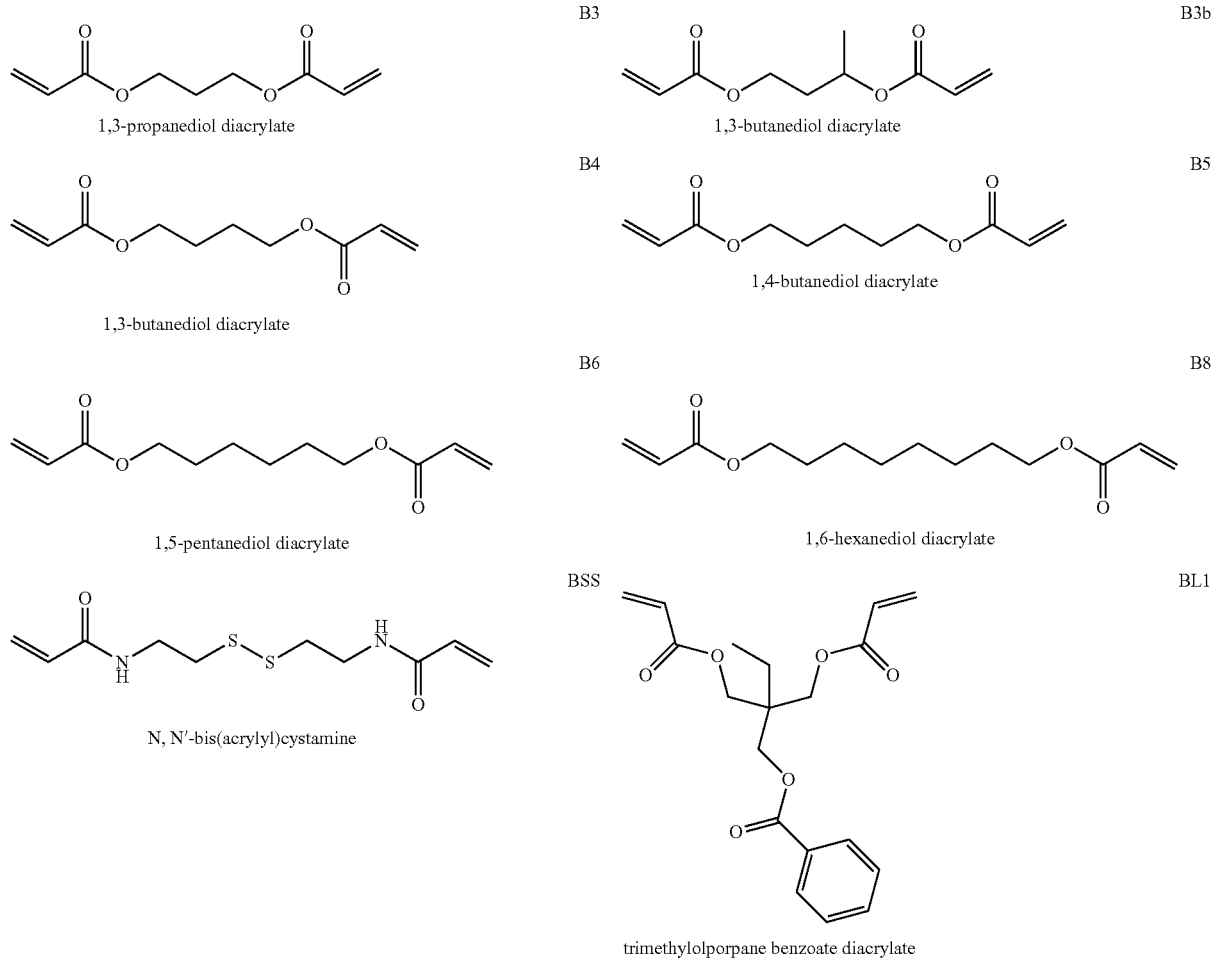

Scheme 2. Example structures of backbone ("B" or R), side chain ("S or R'), and end groups. ("E " or R").

-continued

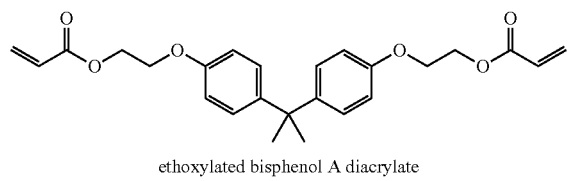
ethoxylated bisphenol A diacrylate BL2

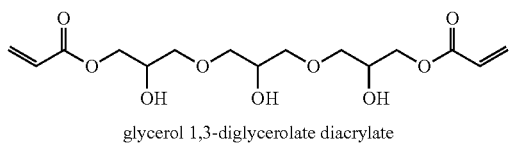
glycerol 1,3-diglycerolate diacrylate BH1

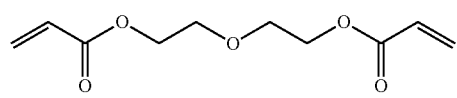
di(ethylene glycol) diacrylate BP1

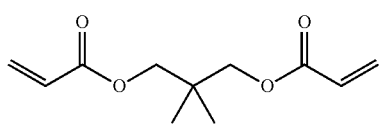
Neopentyl glycol diacrylate BP2

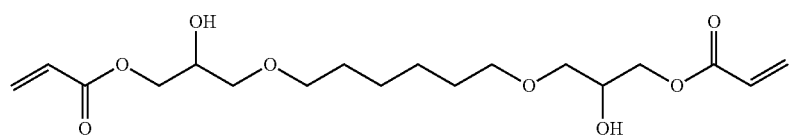
1,6-Hexanediylbis[oxy(2-hydroxy-3, 1-propanediyl)] bisacrylate BP3

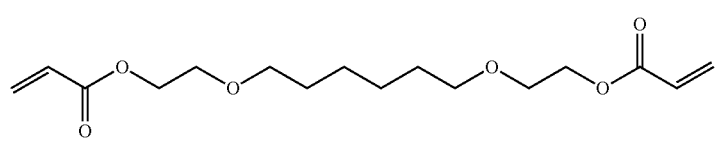
2,2'-(hexane-1,6-diylbis(oxy))bis(ethane-2,1-diyl) diacrylate BP4

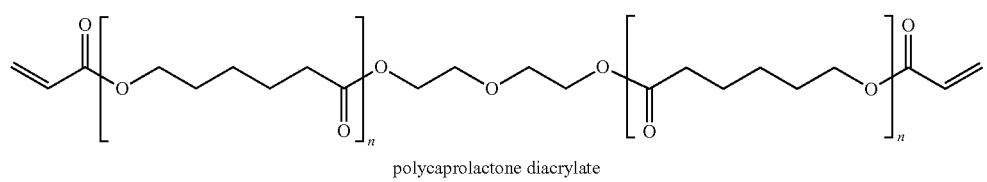
polycaprolactone diacrylate BP5

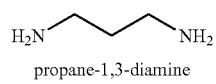
propane-1,3-diamine E1

2,2-dimethylpropane-1,3-diamine E2

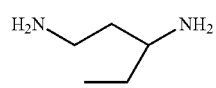
pentane-1,3-diamine E3

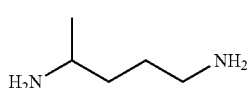
2-methylpentane-1,5-diamine E4

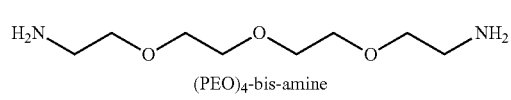
(PEO)$_4$-bis-amine E5

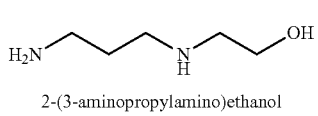
2-(3-aminopropylamino)ethanol E6

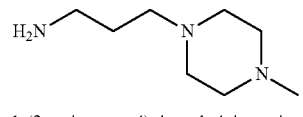
1-(3-aminopropyl)-4-methylpiperazine E7

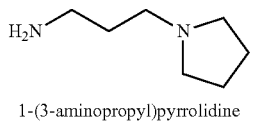
1-(3-aminopropyl)pyrrolidine E8

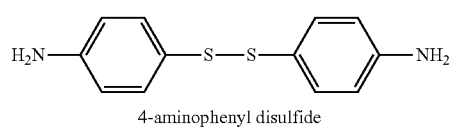
4-aminophenyl disulfide E9

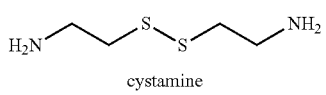
cystamine E10

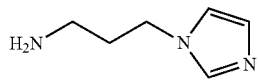

N-(3-aminopropyl)-imidazole

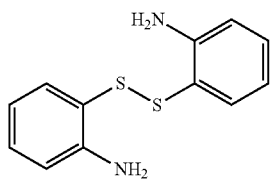

2,2'-dithiobis-benzenamine

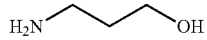

3-amino-1-propanol

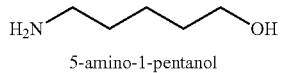

5-amino-1-pentanol

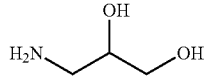

3-aminopropane-1,2-diol

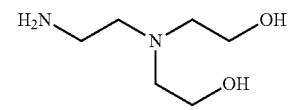

2,2'-(2-aminoethylazanediyl)diethanol

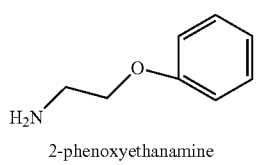

2-phenoxyethanamine

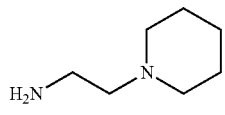

1-(2-Aminoethyl)piperidine

E12

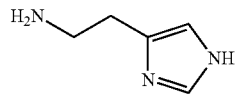

histamine

E14

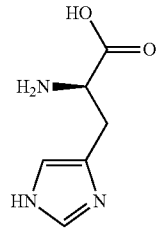

D-histidine

S4

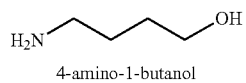

4-amino-1-butanol

S6

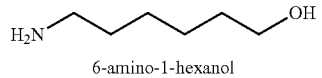

6-amino-1-hexanol

S8

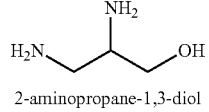

2-aminopropane-1,3-diol

S10

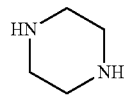

piperazine

S12

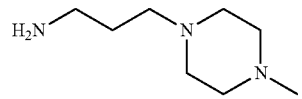

1-(3-aminopropyl)-4-methylpiperazine

E11

E13

S3

S5

S7

S9

S11

S13

More generally, R' can be any group that facilitates solubility in water and/or hydrogen bonding, for example, OH, $NH_2$, and SH. In some embodiments, R' comprises a functional group selected from the group consisting of —OH, —$NH_2$ and —SH. In particular embodiments, R' comprises at least one hydroxyl (OH) group. In more particular embodiments, R' comprises a side chain derived from a compound selected from the group consisting of S3, S4, S5, S6, S7, S8, S9, S10, S11, S12, and S13, as defined hereinabove.

In some embodiments of the compound of formula (I), at least one R" comprises a $C_1$-$C_{30}$ alkyl chain. In particular embodiments, the alkyl chain is terminated with a functional group selected from the group consisting of —OH and —$NH_2$. In more particular embodiments, R" comprises an end group derived from a compound selected from the group consisting of E1, E2, E3, E4, E5, E6, E7, E8, E9, E10, E11, E12, E13, and E14, as defined hereinabove.

In particular embodiments, the compound of formula (I) has the following structure:

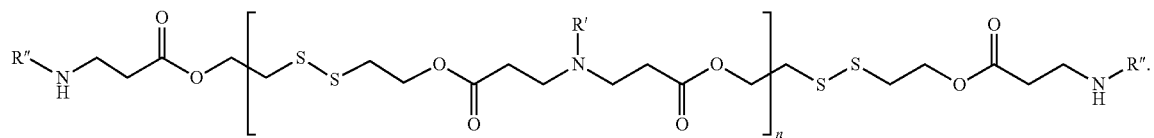

In more particular embodiments, the compound of formula (I) has the following structure:

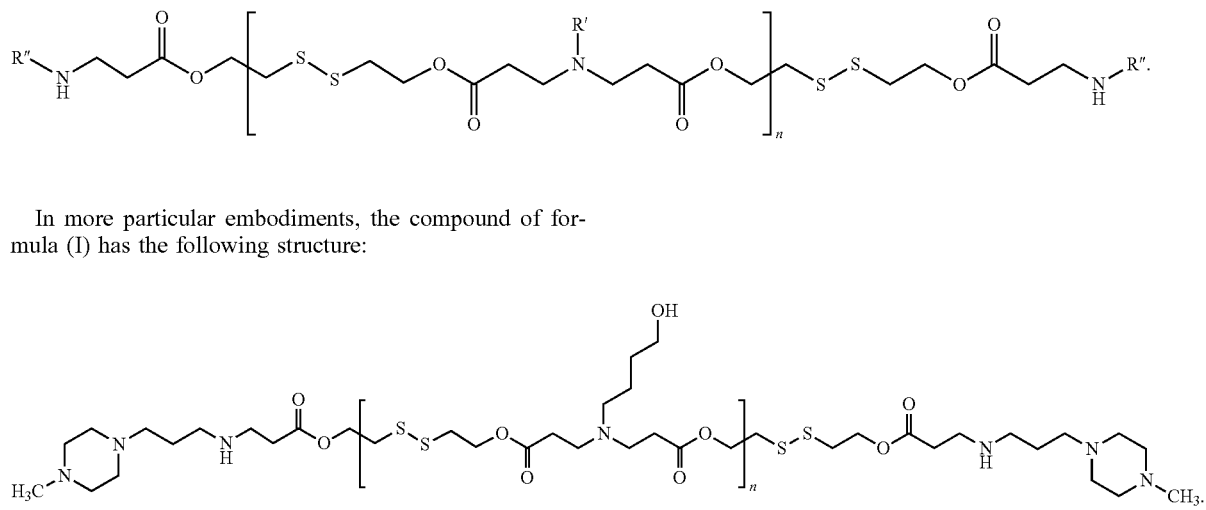

In some embodiments, the R" groups can impart one or more of the following characteristics to the compound of formula (I): independent control of cell-specific uptake and/or intracellular delivery of a particle; independent control of endosomal buffering and endosomal escape; independent control of DNA release; triggered release of an active agent; modification of a particle surface charge; increased diffusion through a cytoplasm of a cell; increased active transport through a cytoplasm of a cell; increased nuclear import within a cell; increased transcription of an associated DNA within a cell; increased translation of an associated DNA within a cell; increased persistence of an associated therapeutic agent within a cell, wherein the therapeutic agent is selected from the group consisting of DNA, RNA, a peptide or a protein.

In certain embodiments, R" comprises a non-reducible amino group independent from the structure of R' or —C—R'. In more certain embodiments, the non-reducible R" group is selected from the group consisting of:

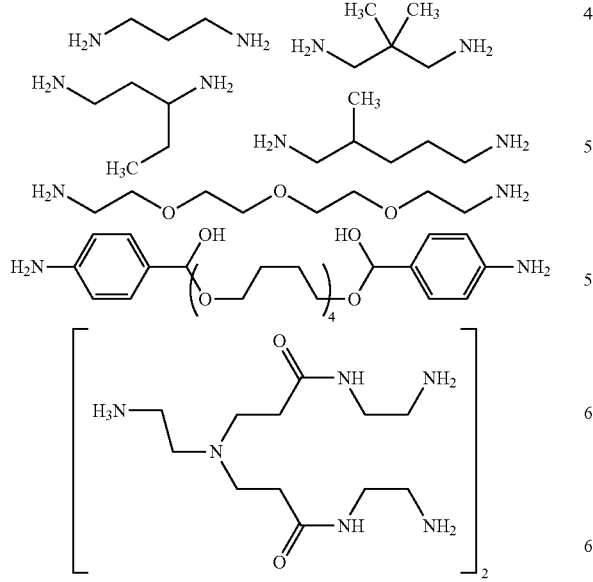

-continued

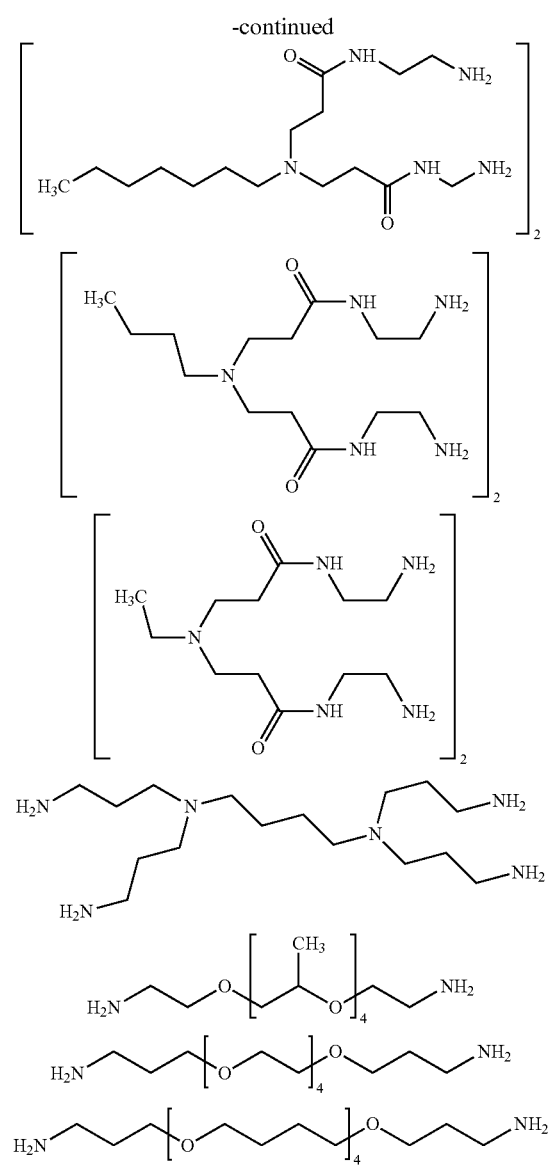

-continued
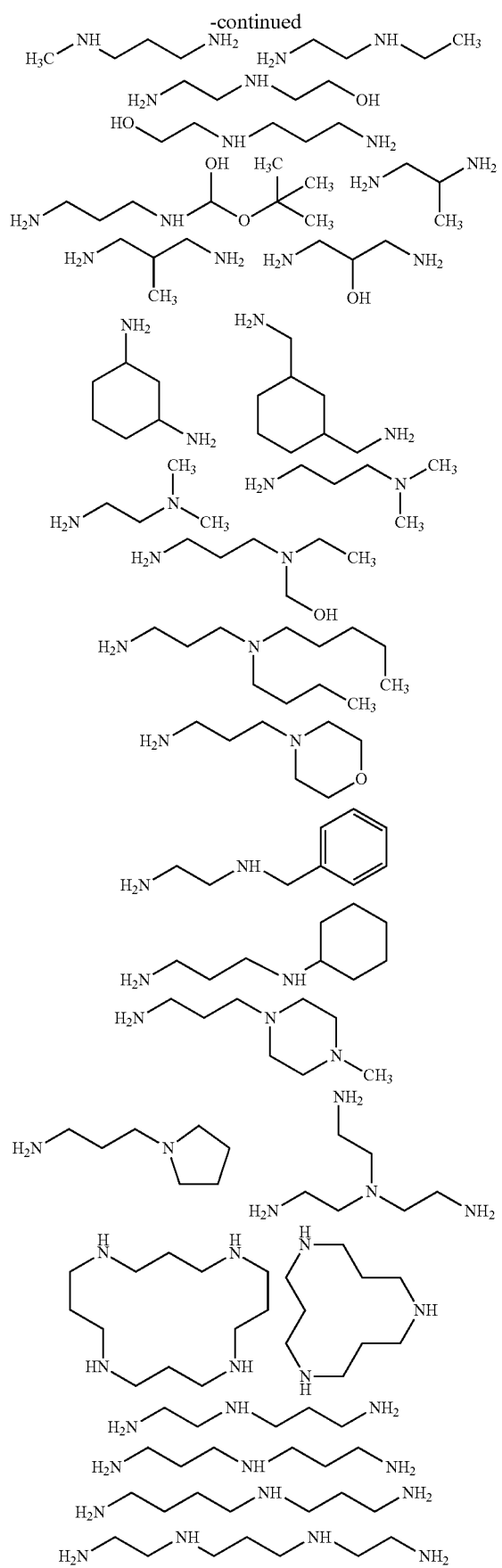
-continued
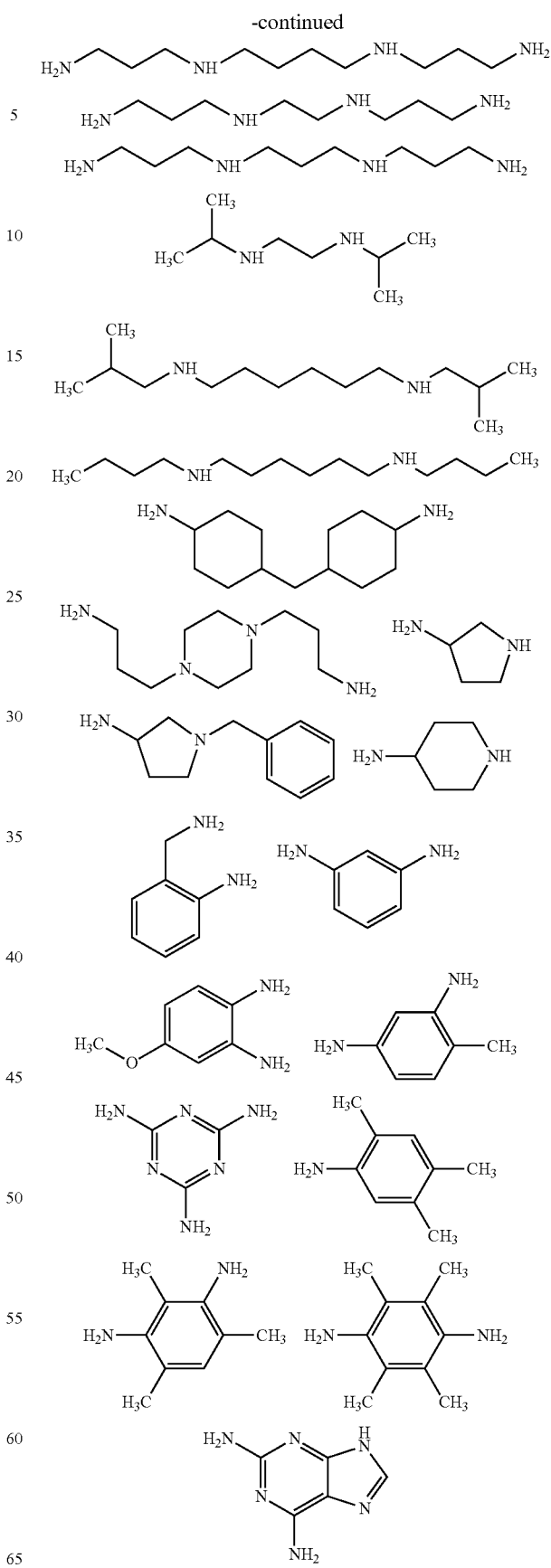

-continued

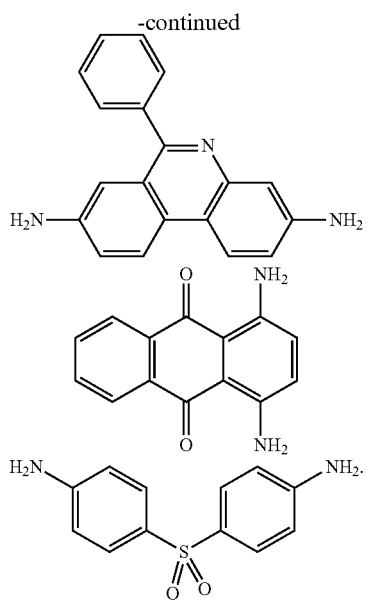

In other embodiments, R" can comprise a larger biomolecule including, but not limited to, poly(ethyleneglycol) (PEG), a targeting ligand, including, but not limited to, a sugar, a small molecule, an antibody, an antibody fragment, a peptide sequence, or other targeting moiety known to one skilled in the art; a labeling molecule including, but not limited to, a small molecule, a quantum dot, a nanoparticle, a fluorescent molecule, a luminescent molecule, a contrast agent, and the like; and a branched or unbranched, substituted or unsubstituted alkyl chain.

In some embodiments, the branched or unbranched, substituted or unsubstituted alkyl chain is about 2 to about 5 carbons long; in some embodiments, the alkyl chain is about 6 to about 8 carbons long; in some embodiments, the alkyl chain is about 9 to about 12 carbons long; in some embodiments, the alkyl chain is about 13 to about 18 carbons long; in some embodiments, the alkyl chain is about 19 to about 30 carbons long; in some embodiments, the alkyl chain is greater than about 30 carbons long.

In certain embodiments, both R" groups, i.e., the end groups of the polymer, comprise alkyl chains. In other embodiments, only one R" group comprises an alkyl chain. In some embodiments, at least one alkyl chain is terminated with an amino ($NH_2$) group. In other embodiments, the at least one alkyl chain is terminated with a hydroxyl (OH) group.

In some embodiments, the PEG has a molecular weight of about 5 kDa or less; in some embodiments, the PEG has a molecular weight of about 5 kDa to about 10 kDa; in some embodiments, the PEG has a molecular weight of about 10 kDa to about 20 kDa; in some embodiments, the PEG has a molecular weight of about 20 kDa to about 30 kDa; in some embodiments, the PEG is greater than 30 kDa. In certain embodiments, both R" groups comprise PEG. In other embodiments, only one R" group comprises PEG.

Further, in some embodiments, one R" group is PEG and the other R" group is a targeting ligand and/or labeling molecule as defined herein above. In other embodiments, one R" group is an alkyl chain and the other R" group is a targeting ligand and/or labeling molecule.

In further embodiments, as described herein below in Example 7, the compounds of formula (I) can be cross-linked.

II. Bioreducible Poly(β-Amino Ester) Copolymers for siRNA Delivery

The presently disclosed subject matter further optimizes poly(β-amino ester)-based nanoparticles for the delivery of siRNA by varying properties, including, but not limited to, polymer bioreducibility and hydrophobicity, particle concentration, and siRNA loading, to provide nanoparticles capable of effective gene knockdown in primary human glioblastoma cells with little to no toxicity and using very low siRNA doses.

Two obstacles specific to siRNA delivery are unstable particle formation and cytoplasmic targeting. The former obstacle arises from the size and rigidity of siRNA, which is stiffer than DNA and is approximately 200 times smaller than most plasmids used for delivery. Hagerman, P. J. *Annu. Rev. Biophys. Biomol. Struct.* 1997, 26, 139-156; Kebbekus, P., et al., *Biochemistry* 1995, 34, (13), 4354-4357. The shorter length of siRNA leads to reduced multivalency in the electrostatic interactions between the polymer and siRNA, while its rigidity may prevent siRNA from conforming into shapes favorable for binding.

With regard to the latter obstacle, cytoplasmic targeting of siRNA is required for optimal gene knockdown as the cytosol is the site of RNAi-induced mRNA degradation. Kawasaki, H.; Taira, K. *Nucleic Acids Res.* 2003, 31, (2), 700-707. Polymer bioreduction by glutathione (GSH) in the reducing cytoplasmic environment is a simple and specific method to create cytoplasmic siRNA release. Griffith, O. W. *Free Radical Bio. Med.* 1999, 27, (9-10), 922-935. This bioreduction is achieved by the inclusion of bioreducible disulfide bonds as a cross-linking agent, Miyata, K., et al., *J. Am. Chem. Soc.* 2004, 126, (8), 2355-2361, in the polymer end-caps, Tzeng, S. Y.; Green, J. J. *Adv. Healthcare Mater.* 2012; Tzeng, S. Y., et al., *Biomaterials* 2012, 33, (32), 8142-8151, or along the polymer backbone. Kozielski, K. L., et al., *Chem. Commun.* 2013.

The presently disclosed subject matter optimizes siRNA delivery with bioreducible PBAEs by addressing these two obstacles. Previous work described the synthesis and characterization of a linear PBAE having disulfide bonds along the polymer backbone that was capable of effectively delivering siRNA with limited cytotoxicity. Kozielski, K. L., et al., *Chem. Commun.* 2013. In some embodiments, the presently disclosed subject matter further optimizes these polymers by balancing polymer bioreducibility and hydrophobicity. PBAE hydrophobicity may enhance particle stability and has been shown to promote enhanced delivery of both DNA and siRNA. Tzeng, S. Y.; Green, J. J. *Adv. Healthcare Mater:* 2012; Sunshine, J. C., et al., Biomacromolecules 2011, 12, (10), 3592-3600.

To further elucidate ideal siRNA delivery criteria, the effects of changing nanoparticle formulation parameters and physical properties on gene knockdown and cytotoxicity also were examined. The results disclosed herein demonstrate that PBAE chemical properties and nanoparticle physical properties can be optimized for simple, safe, and effective siRNA delivery.

Referring now to Scheme 3, bioreducible monomer 2,2'-disulfanediylbis(ethane-2,1-diyl) diacrylate (referred to herein as "BR6") was synthesized in a method similar to Chen et al., Chen, J., et al., *Biomacromolecules* 2011, 12, (10), 3601-11, in which bis(2-hydroxyethyl) disulfide was acrylated with acryloyl chloride in the presence of triethylamine (TEA). The TEA HCl precipitate was removed by filtration following the reaction, and the product was further purified by $Na_2CO_3$ washes and rotary evaporation. Proton nuclear magnetic resonance (HI-NMR) was used to confirm the identity and purity of the product.

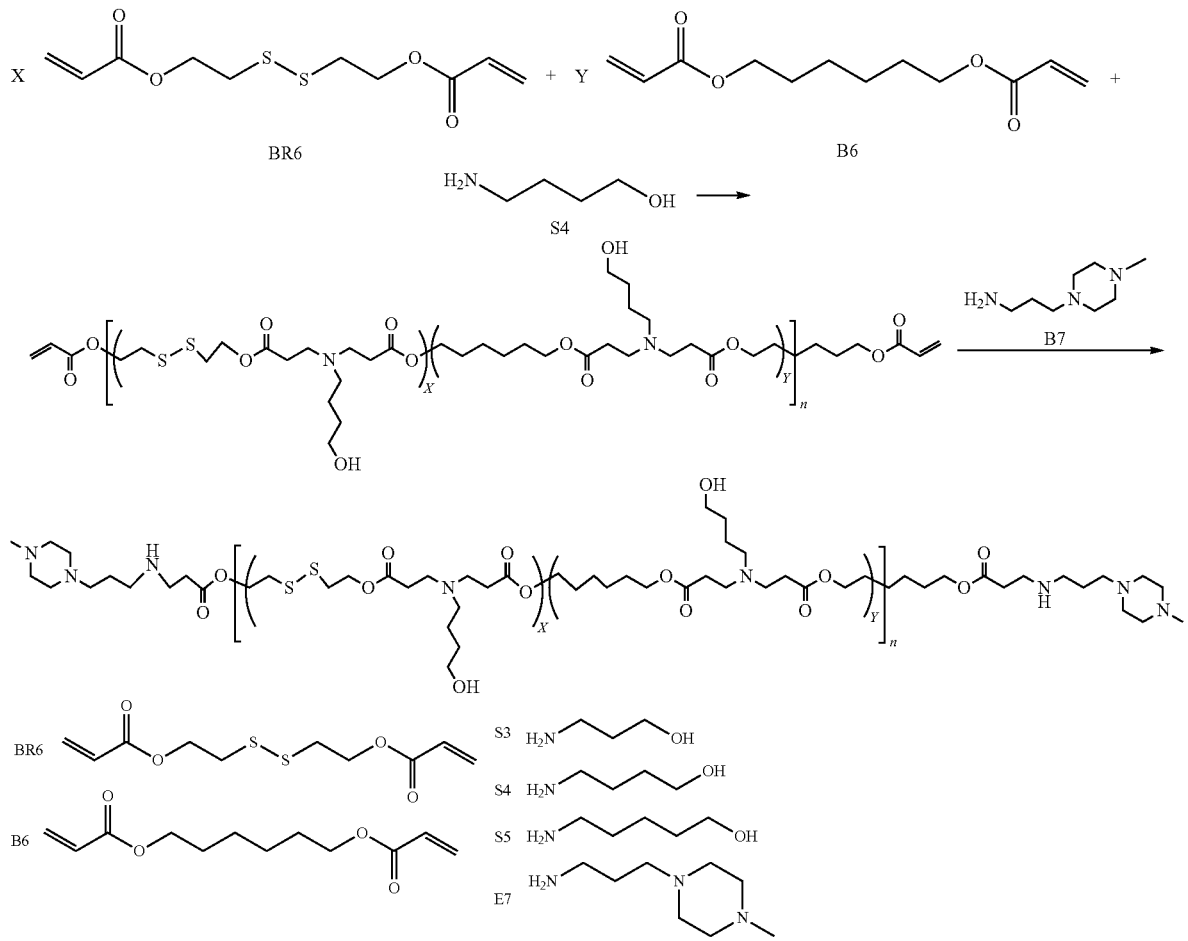

Diacrylate base monomers BR6 and B6 were randomly copolymerized at a ratio of X:Y with side chain S3, S4, or S5, (demonstrated with S4 above in Scheme 5). The resulting acrylate-terminated base copolymers were then end-capped with small molecule E7. The representative copolymer shown above is referred to as "X:Y R647."

Accordingly, in some embodiments, the presently disclosed subject matter provides a compound of formula (II):

nitrate, fumarate, acetate, carbonate, stearate, laurate, and oleate; $R_1$ and $R_2$ can be the same or different and are each independently a $C_1$-$C_{30}$ alkyl chain; each $R_3$ is a $C_3$-$C_8$ linear or branched alkyl chain; R' is a substituted side chain comprising a functional group that facilitates solubility in water and/or hydrogen bonding; each R" can be the same or different and comprise a non-reducible end group or reducible end group; and pharmaceutically acceptable salts thereof.

(II)

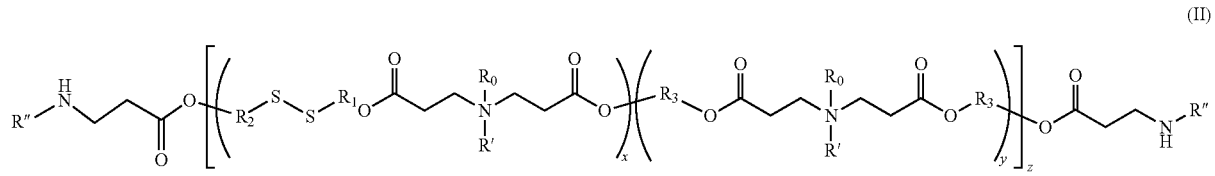

X and Y are integers, which can be represented by a ratio X:Y:Z is an integer from 1 to 10,000; $R_0$ can be present or absent and when present the compound of formula (II) further comprises a counter ion selected from the group consisting of chloride, fluoride, bromide, iodide, sulfate, In some embodiments, Z is an integer from 1 to 100. In yet other embodiments, Z is an integer from 1 to 20.

In particular embodiments, the non-reducible monomer used in preparation of a compound of formula (II) is selected from the group consisting of B3, B3b, B4, B5, and B6, as defined herein. In such embodiments, the compound of formula (II) is selected from the group consisting of:

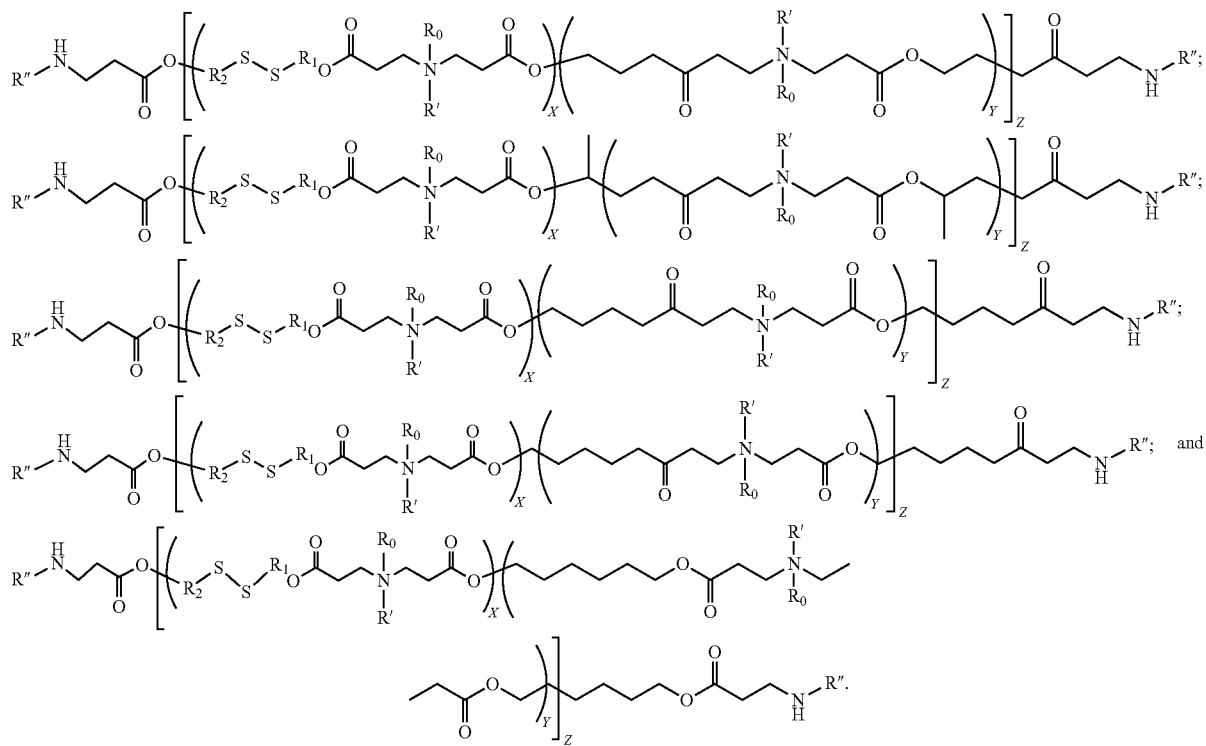

In yet more particular embodiments, the compound of formula (II) has the following formula:

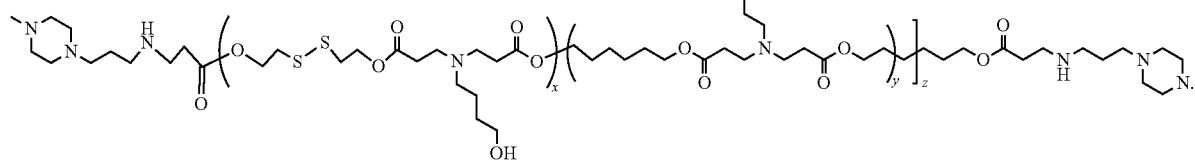

In further embodiments, as described herein below in Example 7, the compounds of formula (II) can be crosslinked.

III. Further Applications of Multicomponent Degradable Cationic Polymers

The presently disclosed subject matter provides the synthesis and characterization of a library of materials that are potentially useful for varied aspects of biomedical engineering. The presently disclosed polymers can be applied in any field where polymers have been found useful including, but not limited to, drug delivery and nucleic acid delivery. Accordingly, in some embodiments, the presently disclosed polymers provide for efficient intracellular delivery of therapeutic agents, such as nucleic acids, proteins, and the like, into cells. Thus, the presently disclosed polymers are well suited for the efficient delivery of DNA for non-viral gene delivery applications.

Accordingly, in some embodiments, the presently disclosed subject matter provides a method for delivering a therapeutic agent to a cell, a specific cell line, a tissue, or an organism, the method comprising associating the therapeutic agent with a presently disclosed compound or a pharmaceutical composition thereof to form one or more particles comprising the agent and presently disclosed compound, and administering the one or more particles or contacting the one or more particles with the cell, specific cell line, tissue or organism. In some embodiments, the therapeutic agent is selected from the group consisting of a gene, DNA, RNA, siRNA, miRNA, isRNA, agRNA, smRNA, a nucleic acid, a peptide, a protein, a chemotherapeutic agent, a hydrophobic drug, and a small molecule drug. In other embodiments, the therapeutic agent causes gene silencing. In further embodiments, the therapeutic agent is a siRNA and it is delivered to a cell. In some embodiments, the one or more particles enter the cytoplasm of the cell. In other embodiments, the compound is degraded reductively in the cytoplasm to specifically target release of the therapeutic agent in the cytoplasm. In still other embodiments, the compound comprises at least one disulfide bond and the at least one disulfide bond is degraded reductively in the cytoplasm. In further embodiments, the at least one disulfide bond is degraded reductively via glutathione. In still further embodiments, the siRNA is released from the presently disclosed compound after entering the cell, binds to its complementary mRNA, and the complementary mRNA is cleaved.

In some embodiments, a method is provided for silencing a gene, the method comprising contacting a therapeutic agent with a compound of formula (I) or formula (II) to form one or more particles comprising the therapeutic agent and the compound, contacting the one or more particles with a cell, wherein the one or more particles enter the cell, wherein the therapeutic agent is released from the one or more particles and binds to a nucleic acid in the cell, thereby silencing a gene. In further embodiments, the therapeutic agent is siRNA. In other embodiments, the siRNA is released from the one or more particles while the compound of formula (I) or formula (II) is degrading, thereby allowing sustained release of the siRNA. In some embodiments, the compound is degraded reductively in the cytoplasm to specifically target release of the therapeutic agent in the cytoplasm. In further embodiments, the compound comprises at least one disulfide bond and the at least one disulfide bond is degraded reductively in the cytoplasm. In other embodiments, the at least one disulfide bond is degraded reductively via glutathione. In still further embodiments, after the siRNA is released from the one or more particles, the siRNA binds to its complementary mRNA and the complementary mRNA is cleaved.

More particularly, the presently disclosed materials are useful for drug and gene delivery due, in part, to one or more of the following aspects: (a) an ability to bind and encapsulate cargos including, but not limited to, DNA, siRNA, peptides, and proteins; (b) an ability to facilitate uptake of the cargos into a range of cell types, with differential cell-type specificity, for example, being able to tune delivery to certain cell types based on small molecule changes to the ends of the polymers are one aspect of the presently disclosed subject matter; (c) an ability to promote endosomal escape to protect the cargos from degradation and enhance delivery to the cytoplasm or alternatively, an ability to direct delivery to the endosome or other compartments; (d) the materials are bioreducible, which enables triggered intracellular drug release of a given cargo to be tuned to promote optimal delivery to the target cell type of interest. In some embodiments, the presently disclosed polymers degrade only through reducible linkages. In other embodiments, the presently disclosed polymers have multiple modes of degradation and degrade unevenly. For example, certain linkages are broken when the material moves from an oxidative to a reducing environment, other linkages are broken due to the presence of water, and the rates of degradation can be further tuned by other molecules that act as catalysts; (e) the materials are not cytotoxic; and (f) the materials have a large potential for structural diversity.

Accordingly, in some embodiments, the presently disclosed biodegradable, cationic polymers can be used to deliver one or more therapeutic agents, biomolecules or small molecules to a cell, tissue, and/or organism either in vitro or in vivo. Representative therapeutic agents, biomolecules or small molecules include, but are not limited to, DNA, RNA (siRNA, miRNA, isRNA, agRNA, smRNA, and the like), nucleic acids, peptides, proteins, hydrophobic drugs, and small molecules.

Such embodiments can be used to treat various conditions or diseases including, but not limited to, cancer, including brain cancer (including Glioblastoma Multiforme), lung cancer, and other cancers; cardiovascular diseases; infectious diseases; ophthalmic diseases, including age-related macular degeneration. The presently disclosed polymers also can be used as a genetic vaccine or as artificial antigen presenting cells; as an adjuvant; as an immunosuppressant; as an immune system modulator; as agents for cell targeting; for enhancement of crops; enhancement of animals; and other therapeutic use in humans.

In some embodiments, the presently disclosed polymers are put together as a kit for the delivery of an agent, a nucleic acid, DNA, or RNA to a specific cell line or to any non-specified type of cell. In further embodiments, the presently disclosed polymers can be put together as a kit for the delivery of agents to specific cells to generate induced pluripotent stem cells. In some embodiments, the presently disclosed polymers can be put together as a kit for the delivery of agents to stem cells to control their growth, differentiation, and/or development.

The presently disclosed biomaterials (linear or branched oligomers, polymers, or cross-linked polymers) also can be useful for other applications, including, but not limited to, coatings for particles or devices via electrostatic or covalent interactions with the particles or surfaces. Such devices include, but are not limited to, nanoparticles, microparticles, stents, stent-like devices, and the like. Such coated devices also could be included in kits for screening or assay development.

Accordingly, in some embodiments, the presently disclosed polymers can be used to coat surfaces for biomedical applications or environmental applications, including, but not limited to, coating devices, such as stents, stent-like devices, implants, or other biomedical or drug delivery devices. In some embodiments, multilayered coatings comprising 1-10 polymer layers; in some embodiments, 11-20 polymer layers; in some embodiments, 21-30 polymer layers; in some embodiments, 31-50 polymer layers; in some embodiments, 51-100 polymer layers; and in some embodiments, greater than 100 polymer layers.

In some embodiments, the presently disclosed polymers can be used as cosmetic products. In other embodiments, the presently disclosed polymers can be used as dental products In certain embodiments, the degradation products or the presently disclosed polymers are bioactive. In some embodiments, the degradation products are drugs and/or pro-drugs. In other embodiments, the degradation products facilitate organelle targeting. In yet other embodiments, the degradation products facilitate nuclear targeting.

In certain embodiments, nanoparticles formed through the presently disclosed procedures that encapsulate active agents (such as DNA, siRNA, peptide, and proteins) are themselves encapsulated into a larger microparticle or device. In some embodiments, this larger structure is degradable and in other embodiments it is not degradable and instead serves as a reservoir that can be refilled with the nanoparticles. These microparticles and/or devices can be constructed with any biomaterials and methods that one skilled in the art would be aware. In some embodiments they can be constructed with multi-component degradable cationic polymers as described herein. In other embodiments, they can be constructed by FDA approved biomaterials, including, but not limited to, poly(lactic-co-glycolic acid) (PLGA). In the case of PLGA and the double emulsion fabrication process as an example, the nanoparticles are part of the aqueous phase in the primary emulsion. In the final PLGA microparticles, the nanoparticles will remain in the aqueous phase and in the pores/pockets of the PLGA microparticles. As the microparticles degrade, the nanoparticles will be released, thereby allowing sustained release of the nanoparticles.

In certain embodiments, the nanoparticle targeting (through biomaterial selection, nanoparticle biophysical properties, and/or a targeting ligand) can be combined with transcriptional targeting. Transcriptional targeting includes designing a promoter so that the delivered nanoparticles carrying a nucleic acid cargo are only active in the cells or tissue types of interest. In one particular example applied to treating brain cancer, combinations of different genetic cargos and/or particles are co-delivered simultaneously to deliver nucleic acids that both: (1) induce apoptosis (genes for tumor necrosis factor-related apoptosis-inducing ligand (TRAIL), p53, and the like) and (2) cause differentiation of cancer stem cells (Bone morphogenetic protein 4 (BMP-4) DNA, Glycogen synthase kinase 3beta shRNA/siRNA, and the like). These nucleic acids are driven by brain cancer specific promoters, such as Nestin and Sox-2 for brain cancer stem cells and Glial fibrillary acid protein (GFAP) for glia.

In some embodiments, the presently disclosed subject matter also includes a method of using and storing the polymers and particles described herein whereby a cryoprotectant (including, but not limited to, a sugar) is added to the polymer and/or particle solution and it is lyophilized and stored as a powder. Such a powder is designed to remain stable and be reconstituted easily with aqueous buffer as one skilled in the art could utilize.

IV. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

The term "siRNA", "small interfering RNA", "short interfering RNA" or "silencing RNA" is intended to mean a class of double-stranded RNA molecules that are short in length, such as in some embodiments around 20 to 25 nucleotides in length. siRNA interferes with the expression of specific genes with a complementary nucleotide sequence.

The term "gene silencing" or "gene knockdown" is intended to mean herein as the switching off of a gene because the mRNA transcribed from that gene is bound so that it is inactive or it is destroyed.

The term "glutathione" (GSH) is meant to refer to a tripeptide that, in some embodiments, reduces disulfide bonds formed within cytoplasmic proteins to cysteines by serving as an electron donor.

By "degraded reductively", it is meant in some embodiments that the presently disclosed compounds have at least one disulfide bond reduced to a cysteine resulting in degradation of the compound and release of the therapeutic agent.

While the following terms in relation to compounds of Formulae 1-11 are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

A named "R" or group will generally have the structure that is recognized in the art as corresponding to a group having that name, unless specified otherwise herein. For the purposes of illustration, certain representative "R" groups as set forth above are defined below.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom. Representative alkyl groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, and the like, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of N, O, and S, and optionally can include one or more double bonds. The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, and the like.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propyne, 3-hexyne, and the like.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($-CH_2-$); ethylene ($-CH_2-CH_2-$); propylene ($-(CH_2)_3-$); cyclohexylene ($-C_6H_{10}-$); $-CH=CH-CH=CH-$; $-CH=CH-CH_2-$; $-(CH_2)_qN(R)-(CH_2)_r-$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($-O-CH_2-O-$); and ethylenedioxyl ($-O-(CH_2)_2-O-$). An alkylene group can have about 2 to about 3 carbon atoms and can further have 6-20 carbons.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, alkenyl, alkynyl, aryl, substituted aryl, aralkyl, hydroxyl, alkoxyl, aryloxyl, aralkyloxyl, carboxyl, acyl, halo, haloalkyl, nitro, alkoxycarbonyl, aryloxycarbonyl, aralkoxycarbonyl, acyloxyl, amino, alkylamino, dialkylamino, trialkylamino, acylamino, aroylamino, carbamoyl, cyano, alkylcarbamoyl, dialkylcarbamoyl, carboxyaldehyde, carboxyl, alkoxycarbonyl, carboxamide, arylthio, alkylthio, alkylene, thioalkoxyl, and mercapto.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The terms "heteroaryl" and "aromatic heterocycle" and "aromatic heterocyclic" are used interchangeably herein and refer to a cyclic aromatic radical having from five to ten ring atoms of which one ring atom is selected from sulfur, oxygen, and nitrogen: zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide. Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)piperazine, 4-(2-chlorophenyl)piperazine, 4(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl) piperazine, 4(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl) piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacycloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole. The heteroaryl ring can be fused or otherwise attached to one or more heteroaryl rings, aromatic or non-aromatic hydrocarbon rings, or heterocycloalkyl rings. A structure represented generally by the formula:

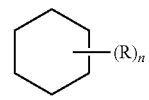

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

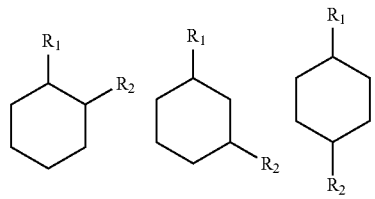

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

When a named atom of an aromatic ring or a heterocyclic aromatic ring is defined as being "absent," the named atom is replaced by a direct bond.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —$CONH_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

The terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R' are each independently selected from the group consisting of alkyl groups. Additionally, R', R", and/or R'"taken together may optionally be —$(CH_2)_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

Further, as used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm. In yet other embodiments, the nanoparticle has a diameter of about 1000 nm (1 µm). In such embodiments, the particle also can be referred to as a "microparticle. Thus, the term "microparticle" includes particles having at least one dimension in the range of about one micrometer (µm), i.e., $1 \times 10^{-6}$ meters, to about 1000 μm. The term "particle" as used herein is meant to include nanoparticles and microparticles.

It will be appreciated by one of ordinary skill in the art that nanoparticles suitable for use with the presently disclosed methods can exist in a variety of shapes, including, but not limited to, spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes. In particular embodiments, the presently disclosed nanoparticles have a spherical shape.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Biocompatible": The term "biocompatible", as used herein is intended to describe compounds that are not toxic to cells. Compounds are "biocompatible" if their addition to cells in vitro results in less than or equal to 20% cell death, and their administration in vivo does not induce inflammation or other such adverse effects.

"Biodegradable": As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compounds are uncatalyzed.

"Effective amount": In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

"Peptide" or "protein": A "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, and the like. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, 0(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Synthesis of R647

A reducible form of a previously established monomer, hexane-1,6-diyl diacrylate (B6), was synthesized to form "reducible B6,"2,2'-disulfanediylbis(ethane-2,1-diyl) diacrylate (BR6), to form polymers having the same charge density as B6 polymers. Synthesis of BR6 was carried out in a method similar to Chen et al. (2011). Briefly, bis(2-hydroxyethyl) disulfide was acrylated with acryloyl chloride in the presence of triethylamine (TEA). Following reaction, TEA HCl precipitate was removed by filtration, and the product was purified with aqueous $Na_2CO_3$ washes followed by rotary evaporation (Scheme 1). The product was confirmed by proton nuclear magnetic resonance ($H^1$—NMR) (data not shown).

The two-step polymer synthesis was carried out in a similar manner as in Bhise et. Al (2010). Either diacrylate monomer, BR6 or B6, was polymerized with 4-amino-1-butanol (S4) in a 1.01:1 molar ratio, yielding acrylate terminated base polymers. The B6-S4 or BR6-S4 base polymers were then end-capped with 1-(3-aminopropyl)-4-methylpiperazine (E7) to yield either B6-S4-E7 (647) or BR6-S4-E7 (R647). Polymer size and structure were confirmed using gel permeation chromatography (GPC) and $H^1$—NMR (FIG. 3), respectively. GPC results of R647 yielded MN of 3745 Da, MW of 7368 Da, and a PDI of 1.967. GPC results of 647 yielded a comparable size profile (MN 4037 Da, MW 6221 Da, PDI 1.597).

Example 2

Characterization of Polymer-siRNA Binding Using R647 and 647

The siRNA binding capability of each polymer was evaluated by a YO-PRO®-1 Iodide competition binding assay (FIG. 4), in which YO-PRO®-1 Iodide fluoresces upon binding double stranded nucleic acids and is quenched as it is replaced by increasing concentrations of polymer. Over the polymer concentrations tested, R647 showed comparable or slightly higher binding as measured by YO-PRO®-1 Iodide quenching.

Polymer-siRNA binding was further characterized using a gel retention assay (FIG. 5), in which nanoparticles are added to the wells of an agarose gel, and tightly bound siRNA is unable to migrate under electric field (100 V). To repeat this assay in conditions mimicking the reducing cytoplasmic environment, nanoparticles were incubated in 5 mM GSH immediately prior to electrophoresis. Without GSH, both R647 and 647 showed complete siRNA complexation with polymer:siRNA weight ratios (wt/wts) as low as 75:1. In the presence of cytoplasmic levels of GSH, R647 completely released siRNA, even at the highest wt/wt examined, while 647 binding was unaffected. These results combined with the competition binding data show that R647 can not only condense and protect siRNA as well as or slightly better than 647 when in extracellular conditions, but also is able to completely release siRNA within minutes of exposure to cytoplasmic GSH levels.

Nanoparticles formed from R647 or 647 were characterized by size via nanoparticle tracking analysis (NTA) using a NanoSight NS500 and surface charge (ζ-potential) via dynamic light scattering (DLS) using a Malvern Zetasizer NanoZS (FIG. 6). For each polymer, nanoparticles were formed at either 450 wt/wt or 112.5 wt/wt. For all four formulations tested, the nanoparticle diameter remained between 111 nm and 118 nm, which falls in the appropriate size range for efficient cellular uptake (Green, 2008). Therefore, the nanoparticle diameter was not significantly different between all four samples. For particles formed at 112.5 wt/wt with either R647 or 647, ζ-potential was neutral (between −10 and +10 mV), while particles formed at 450 wt/wt with R647 or 647 had a ζ-potential of 19.0±1.0 mV and 20.6±0.8 mV, respectively. Therefore, the ζ-potential of 450 wt/wt formulations of R647 and 647 was not significantly different and the ζ-potential of 112.5 wt/wt formulations of R647 and 647 was significantly different but effectively neutral (between −10 and 10 mV). In some embodiments, the 450 wt/wt formulations are desirable for nucleic acid delivery, as their positive charge attracts them to the negatively charged glycocalyx of the cell surface.

Example 3

Gene Knockdown and Cellular Loss in Metabolic Activity

Gene knockdown and cellular loss in metabolic activity were evaluated in glioblastoma GBM 319 cells expressing GFP, using siRNA targeted at GFP, or a scrambled control siRNA (scRNA) (FIGS. 7 and 8). Loss in metabolic activity was measured 24 h post transfection using a CellTiter 96® AQueous One Solution cell proliferation assay and read using a BioTek® Synergy™2 Microplate Reader. GFP expression was measured 9 d post-transfection using a BD Accuri™ C6 flow cytometer (emission filter: 530/30 nm). Transfections were performed with 26.7 nM siRNA using R647 or 647 at either 450 wt/wt or 112.5 wt/wt. The 450 wt/wt formulation of 647 achieved 75.2±12.2% GFP knockdown but with 94.3±0.7% loss in metabolic activity, indicating that this treatment was very toxic. The 112.5 wt/wt formulations of either polymer did not exhibit marked loss in metabolic activity, but were unable to achieve substantial GFP knockdown. Incredibly, R647 at 450 wt/wt achieved 91.8±0.7% GFP knockdown, with no measurable loss in metabolic activity. This observation demonstrates that addition of a bioreducible moiety to the PBAE backbone not only improved siRNA delivery but also attenuated toxicity.

FIG. 9 shows the results on gene knockdown and cellular loss in metabolic activity when R637, R647, and R657, formed from S3, S4, and S5, respectively (structures shown in FIG. 2), were added to the assay in ratios of 3:1, 1:1, and 1:3. In addition, 637, 647, and 657 also were tested in the assay. Results demonstrated that R647 had the highest levels of gene knockdown with no marked toxicity (loss in metabolic activity).

Figure 10:
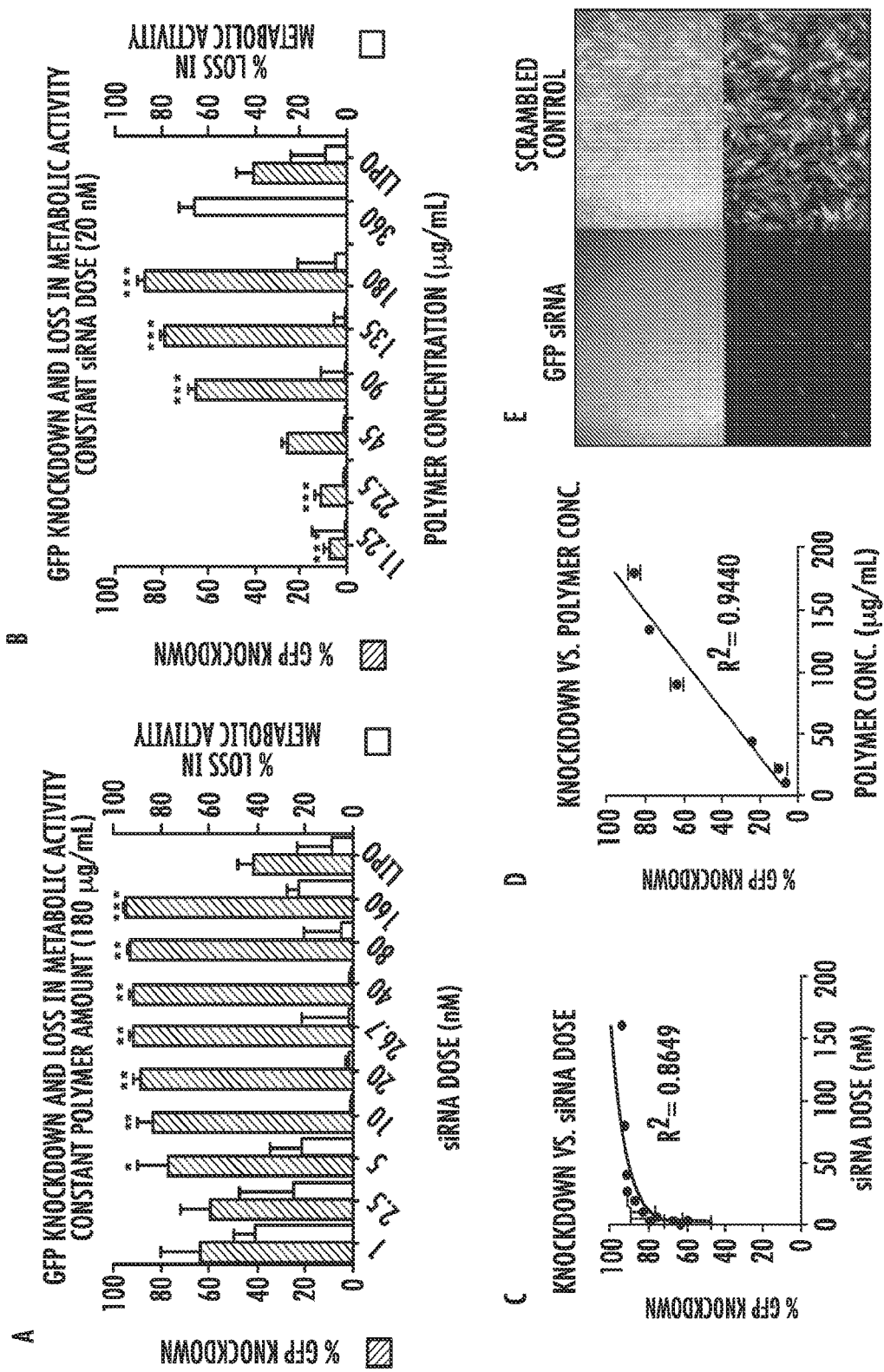

R647 was further tested to determine the effect of varying the siRNA dosage in the assay (FIG. 10A). Results suggested that a concentration of 10 nM to 80 nM siRNA in the assay resulted in high levels of gene knockdown with low or no levels of toxicity. siRNA levels at about 5 nM or lower or at 160 nM led to higher toxicity and lower levels of gene knockdown.

In addition, keeping the siRNA levels consistent at 20 nM and increasing the R647 polymer amount from approximately 11 µg/mL to approximately 360 µg/mL showed a direct correlation between the amount of polymer added and the amount of gene knockdown (FIGS. 11B and 11D).

In summary, the presently disclosed subject matter demonstrates that BR6 is capable of forming a novel bioreducible PBAE. Further, R647 formed particles with siRNA that were nearly identical in physical properties as 647. siRNA release from BR6-based polymers occurred within minutes of entering a reducing environment comparable to the environment of the cytosol. The BR6/B6 polymer blends maximized gene knockdown. Also, the 1:1 R647 nanoparticle achieved near complete knockdown with no cytotoxicity using as little as 10 nM siRNA. Gene knockdown was found to be more sensitive to the total amount of polymer in the delivery system than the siRNA dose or the polymer to siRNA ratio. The BR6 based bioreducible PBAE siRNA nanoparticles were capable of achieving over 90% gene knockdown with no cytotoxicity.

Example 4

Summary of Bioreducible Poly(β-Amino Ester) R647 for siRNA Delivery

A bioreducible PBAE for siRNA delivery that is both efficacious and innocuous has been synthesized and characterized. The reducible polymer R647, a linear poly(β-amino) ester, was shown to bind siRNA as well as or slightly better than its non-reducible analog 647. It was demonstrated that this new polymer is capable of condensing and protecting siRNA in nanoparticles with the same physical properties as the previously established 647 particles. It also was demonstrated that siRNA release from R647 occurs within minutes of entering a reducing environment comparable to the cytosol. It has been demonstrated that R647 nanoparticles that differed from 647 only in reducibility were able to achieve near-complete gene knockdown with no toxicity, while analogous 647 nanoparticles were extremely toxic. This new class of polymer has exciting therapeutic potential as a safe and effective siRNA delivery vehicle.

Example 5

Bioreducible Poly(β-Amino Ester) Copolymers for siRNA Delivery

Copolymer synthesis was carried out in a method similar to Bhise et al., *Biomaterials* 2010, 31, (31), 8088-8096. Base monomers BR6 and hexane-1,6-diyl diacrylate (B6) were mixed at a ratio of either 1:0, 3:1, 1:1, 1:3, or 0:1 prior to copolymerization. The base monomers were then polymerized with either side chain 3-amino-1-propanol (S3), 4-amino-1-butanol (S4), or 5-amino-1-pentanol (S5) at a base monomer to side chain ratio of 1.01:1, yielding acrylate terminated polymers. These copolymers were then end-capped with small molecule 1-(3-aminopropyl)-4-methylpiperazine (E7) (Scheme 5).

As an example, a polymer synthesized with a 3:1 BR6:B6 ratio, side chain S3, and end-capped with E7 will be referred to as "3:1 R637" herein, whereas the same polymer with a 0:1 BR6:B6 ratio will be referred to as "637." Polymer size was characterized via gel permeation chromatography (see Table 1).

TABLE 1

Gel Permeation Chromatography of Representative Polymers

| Polymer | $M_n$ | $M_w$ | PDI |
| --- | --- | --- | --- |
| R637 | 2344 | 3899 | 1.6636 |
| 3:1 R637 | 2623 | 4548 | 1.7342 |
| 1:1 R637 | 2882 | 5046 | 1.7506 |
| 1:3 R637 | 3416 | 5711 | 1.6717 |
| 637 | 2369 | 3244 | 1.3693 |
| R647 | 2474 | 4001 | 1.6176 |
| 3:1 R647 | 2843 | 4900 | 1.7233 |
| 1:1 R647 | 3211 | 5597 | 1.7434 |
| 1:3 R647 | 3483 | 6347 | 1.8226 |
| 647 | 3962 | 6193 | 1.5631 |
| R657 | 2628 | 4102 | 1.5607 |
| 3:1 R657 | 3233 | 4198 | 1.2987 |
| 1:1 R657 | 2779 | 4683 | 1.6852 |
| 1:3 R657 | 3560 | 6038 | 1.6959 |
| 657 | 2357 | 4158 | 1.7637 |

The in vitro siRNA delivery efficacy and cytotoxicity of each of the presently disclosed fifteen polymers was evaluated in glioblastoma (GBM 319) cells expressing constitutive GFP using GFP-targeting siRNA with sequence 5'-CAAGCUGACCCUGAAGUUCTT (sense) and 3'-GAACUUCAGGGUCAGCUUGCC (antisense), or a scrambled control siRNA (scRNA) with sequence 5'-AGUACUGCUUACGAUACGGTT (sense) and 3'-CCGUAUCGUAAGCAGUACUTT (anti-sense).

LIPOFECTAMINE™ 2000 (Lipo) and siRNA alone were used as controls with 20 nM siRNA and the Lipo:siRNA ratio used was 1 μL:3 μg. Cytotoxicity was measured as loss in metabolic activity at 24 h post-transfection using a CellTiter 96® AQueous One Solution cell proliferation assay and read using a BioTek® Synergy™ 2 Microplate Reader. GFP expression was measured 9 days post-transfection using a BD Accuri™ C6 flow cytometer (emission filter: 530/30 nm), and % GFP knockdown was calculated by normalizing the GFP expression of siRNA-treated cells to scRNA-treated cells. All following transfections were carried out using the same cell line, siRNAs, controls, and data collection protocols, and all formulations that caused >60% loss in metabolic activity were excluded from statistical testing.

In one example, nanoparticles were formed with all fifteen polymers to yield final in vitro concentrations of 180 μg/mL polymer and 20 nM siRNA. These results, which are presented in FIG. 9, show particular trends with regard to polymer bioreducibility and hydrophobicity.

First, the results show that as the polymer side chain becomes more hydrophobic, toxicity increases, a conclusion supported by the statistical results shown in Table 2. An example is polymer 1:1 R647 (with side chain S4) that caused −9±11% loss in metabolic activity versus polymer 1:1 R657, which has a side chain (S5) longer by only one hydrocarbon, and caused 77±13% loss in metabolic activity.

Second, the results show that polymer bioreducibility significantly reduces cytotoxicity, even with polymer compositions as similar as 1:1 BR6:B6 based polymers in which approximately 50% of repeat units are bioreducible, versus 1:3 BR6:B6 based polymers in which approximately 25% of repeat units are bioreducible (Table 2). An example of this extreme toxicity change with a small change to polymer properties is 1:1 R647, with loss in metabolic activity of −9±11% versus 1:3 R647, with loss in metabolic activity of 83±1%.

TABLE 2

Two-way ANOVA of Loss in Metabolic Activity of Polymers with Varying Side Chains, Base Monomers, and Ratio of Base Monomers

|  | P value | Significance |
|---|---|---|
| Side chains |  |  |
| S3 vs. S4 | 0.5877 | ns |
| S3 vs. S5 | <0.0001 | **** |
| S4 vs. S5 | 0.0006 | *** |
| Base monomers[†] |  |  |
| R6 vs. 3:1 | 0.721 | ns |
| R6 vs. 1:1 | 0.2547 | ns |
| R6 vs. 1:3 | <0.0001 | **** |
| R6 vs. B6 | <0.0001 | **** |
| 3:1 vs. 1:1 | 0.9266 | ns |
| 3:1 vs. 1:3 | <0.0001 | **** |
| 3:1 vs. B6 | <0.0001 | **** |
| 1:1 vs. 1:3 | <0.0001 | **** |
| 1:1 vs. B6 | <0.0001 | **** |
| 1:3 vs. B6 | 0.7468 | ns |

[†]ratios for base monomers correspond to BR6:B6.

The tuneable toxicities of the presently disclosed polymers is of particular interest as polymer hydrophobicity has been shown to promote enhanced nucleic acid delivery, Tzeng, S. Y.; Green, J. J. *Adv. Healthcare Mater* 2012; Sunshine, J. C., et al., *Biomacromolecules* 2011, 12, (10), 3592-3600. Accordingly, hydrophobic polymers, such as 647, may be effective for siRNA delivery, but are so toxic that they have no effective therapeutic window. By combining hydrophobic monomers with bioreducible ones, the useful properties of hydrophobicity can be harnessed, while reducing cytotoxicity and promoting cytoplasmic cargo release. Polymer R647, for example, achieved 81±3% GFP knockdown versus 3:1 R647, which achieved 91±1%, a significant increase (p<0.05 by Student's T test), resulting only from making 25% of repeat units more hydrophobic. Another result from this example showed that eight of the polymers tested achieved significantly higher GFP knockdown than LIPOFECTAMINE 2000™ without causing significantly higher losses in metabolic activities. An example image of 1:1 R647 treated cells is shown in FIG. 10E.

To further elucidate the nanoparticle properties favorable for safe and effective siRNA delivery, the effects of changing nanoparticle formulation and the resulting physical properties associated with these changes also were examined. First, siRNA dose-dependency was examined by delivering siRNA at final in vitro doses ranging from 1 nM to 160 nM using polymer 1:1 R647 at a fixed concentration of 180 μg/mL (FIGS. 10A, 10C). The first results from this experiment were that significantly higher GFP knockdown was achieved using only 5 nM siRNA versus LIPOFECTAMINE 2000™ with 20 nM at 76±14% versus 40±7%, respectively, and none of the formulations tested were significantly more toxic than Lipo. Additionally, 63±16% GFP knockdown was achieved with as little as 1 nM siRNA. Interestingly, a particularly dose-dependent trend of GFP knockdown was not observed within the range of nanoparticle formulations tested. This observation may be due to the fact that of the nine polymer/siRNA formulations tested, seven achieved more than 75% knockdown and were significantly more effective than Lipo. Knockdown seemed to correlate semi logarithmically with siRNA dose with $R^2=0.8649$.

Polymer concentration dependency was examined next by carrying out transfections with 20 nM siRNA and varying 1:1 R647 concentrations from 11.25 μg/mL to 360 μg/mL (FIGS. 10B, 10D). Interestingly, GFP knockdown correlated linearly with polymer concentration with $R^2=0.9440$. To elucidate the mechanisms behind these results, the nanoparticle physical properties associated with each delivery method were analysed to determine the size, zeta potential, nanoparticle concentration, and siRNA loading of each formulation. Nanoparticle size and concentration were measured via nanoparticle tracking analysis (NTA) using a NanoSight NS500 and surface charge (zeta potential) was measured via dynamic light scattering (DLS) using a Malvern Zetasizer NanoZS. The siRNA loading was calculated from the nanoparticle concentration, total siRNA dose, and siRNA molecular weight. Nanoparticle concentration measurements were quantified in a manner consistent with the protocol described by Bhise et al., *Small* 2012, 8, (3), 367-373.

To first determine the polymer/siRNA weight ratios (wt/wts) at which siRNA is completely complexed into nanoparticles, a gel retention assay was performed using 1:1 R647 with wt/wts ranging from 37.5 wt/wt to 600 wt/wt (FIG. 11). The results of this assay indicated that siRNA is completely bound to 1:1 R647 at wt/wts as low as 150 wt/wt, but not at 75 wt/wt or 37.5 wt/wt, so siRNA loading could not be calculated for nanoparticle formulations at these wt/wts.

To demonstrate the siRNA release efficacy of this copolymer in a reducing environment comparable to the cytosol, Griffith, O. W. *Free Radical Bio. Med.* 1999, 27, (9-10), 922-935, particles were incubated in a solution of 5 mM glutathione (GSH) for 15 min prior to electrophoresis. All formulations tested showed complete siRNA release, indicating that siRNA unloading can occur within minutes of reaching the cytosol.

Figure 12:
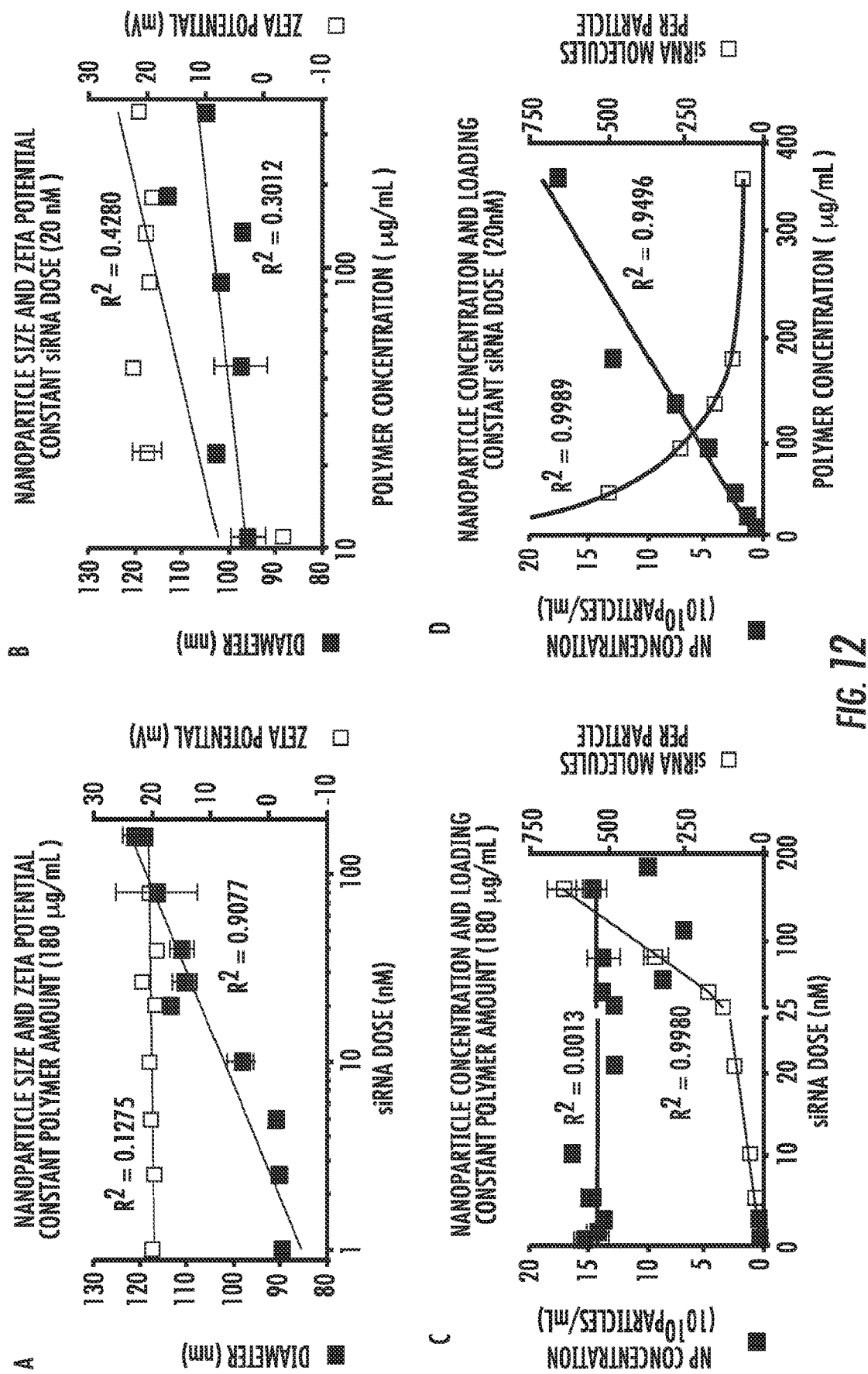

Nanoparticle properties were measured using the same formulations shown in FIG. 10A, in which siRNA dose was varied from 1 nM to 160 nM and 1:1 R647 concentration remained the same at 180 µg/mL. Nanoparticle diameter was shown to correlate with siRNA dose on a semi logarithmic scale ($R^2=0.9077$), while zeta potential remained consistently between 18 mV to 22 mV (FIG. 12A). Size measurements also were completed using 0 nM siRNA. These results showed particles 78±4% nm in size, although this result is not depicted in FIG. 12A as the x-axis is logarithmic. Nanoparticle concentration remained nearly constant with changing siRNA dose, even with 0 nM siRNA, staying between $12.9\text{-}16.6\times10^{10}$ particles/mL ($R^2=0.0013$). The siRNA loading was calculated to show a linear correlation with siRNA dose ($R^2=0.9980$).

The same experiments were repeated, except for the nanoparticle formulations shown in FIG. 10B were used, where siRNA dose remained constant at 20 nM and 1:1 R647 concentration was varied from 11.25 µg/mL to 360 µg/mL. Polymer concentration did not correlate well with either nanoparticle diameter or zeta potential, with $R^2=0.3012$ and 0.4280, respectively (FIG. 12B). Nanoparticle concentration, however, fit a linear regression versus polymer concentration with $R^2=0.9496$. This relationship resulted in siRNA loading values that exponentially decayed with increasing polymer concentration with $R^2=0.9989$, meaning that the most effective siRNA delivery formulations in this group consisted of the highest nanoparticle concentrations, but with the lowest siRNA loading values.

Figure 13:
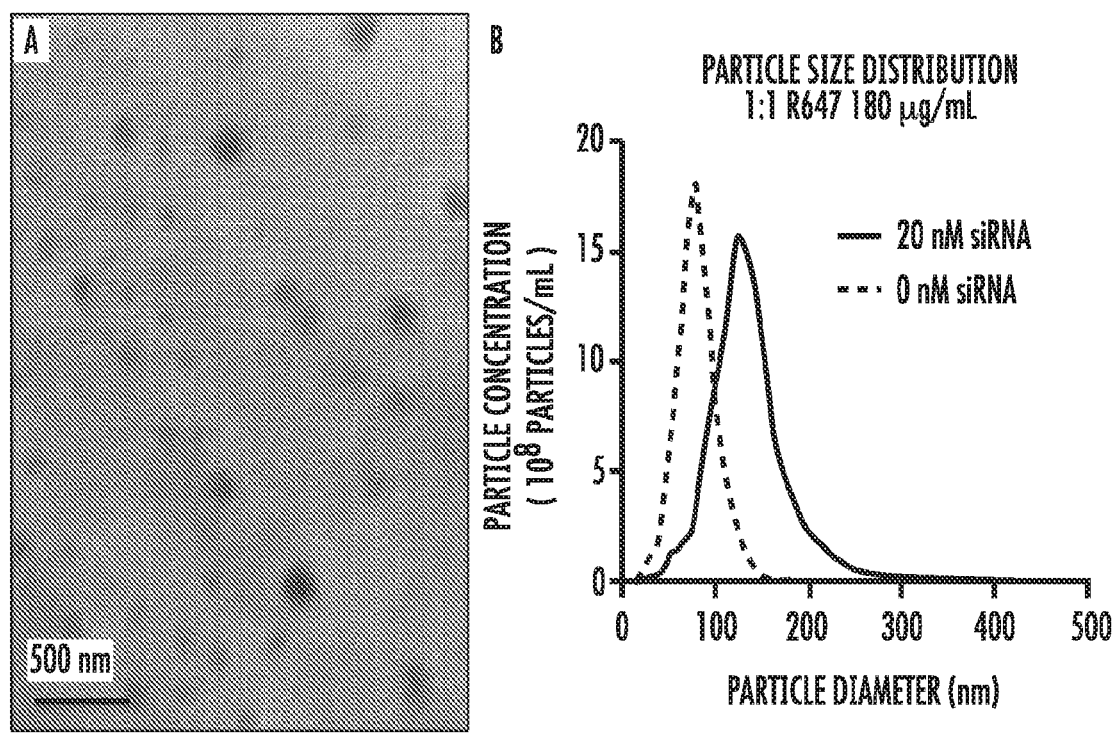

To calculate siRNA loading, the siRNA loading was assumed to be roughly even across all particles. Based on the trend of constant nanoparticle concentrations and increasing diameters with increasing siRNA doses, along with the knowledge that 1:1 R647 forms particles on its own, this is thought to be an accurate assumption. To further support this assumption, however, transmission electron microscopy (TEM) was performed on 1:1 R647 at 180 µg/mL with 20 nM siRNA, and compared the size histogram results from NTA of this formulation to one without siRNA (FIG. 13). TEM shows a roughly uniform size distribution and the NTA histogram of the 20 nM samples were distinct from the 0 nM samples. These observations support the assumption that uneven siRNA loading would result in a population of particles matching the 0 nM, "empty" size distribution and another population appearing larger and therefore loaded with siRNA.

Example 5

Material and Methods Bioreducible Poly(β-Amino Ester) Copolymers for siRNA Delivery A. Materials All chemicals used for the synthesis of monomer BR6 were purchased from Sigma-Aldrich Chemical Co. (St. Louis, MO) and used without further purification. All other monomers were purchased from Alfa Aesar (Ward Hill, MA). LIPOFECTAMINE™ 2000 and Opti-MEM™ I were purchased from Invitrogen (Carlsbad, CA) and used according to manufacturer's instructions. Ambion® Silencer®eGFP and Ambion® Silencer®Negative Control #1 siRNA were purchased from Life Technologies™. Cell-Titer 96® $AQ_{ueous}$ One MTS assay was purchased from Promega (Fitchburg, WI) and used according to manufacturer's instructions.

B. BR6 Synthesis

Bis(2-hydroxyethyl) disulfide (15.4 g, 10 mmol) and triethylamine (TEA, 37.5 mL, 300 mmol) were dissolved in 450 mL of tetrahydrofuran (THF) (previously dried with $Na_2SO_4$) in a one L round bottom flask; the contents were then flushed with $N_2$ for 10 min and maintained under a $N_2$ environment for the remainder of the reaction time. Acryloyl chloride (24.4 mL, 300 mmol) was dissolved in 50 mL of dried tetrahydrofuran, added to the flask dropwise over 2 hrs while stirring, and the reaction was allowed to continue at room temperature for 24 h. Following reaction, TEA HCl precipitate was removed by filtration, and THF was removed by rotary evaporation. The product was dissolved in 200 mL dichloromethane (DCM) and washed five times with 200 mL of aqueous 0.2 M $Na_2CO_3$ and three times with distilled water. The solution was dried with $Na_2SO_4$ and DCM was removed by rotary evaporation. The product 2,2'-disulfanediylbis(ethane-2,1-diyl) (BR6) was confirmed via $H^1$-NMR: ($CDCl_3$, 400 Hz), δ2.95 (2H, t, $CH_2CHCOOCH_2CH_2S$), δ3.95 (2H, t, $CH_2CHCOOCH_2CH_2S$), δ5.8-5.9 (1H, d, $CH_2CHCOOCH_2CH_2S$), δ6.1-6.2 (1H, dd, $CH_2CHCOOCH_2CH_2S$), δ6.4-6.5 (1H, d, $CH_2CHCOOCH_2CH_2S$).

C. Polymer Synthesis

The diacrylate base monomers used for polymerization were BR6 (see above) or hexane-1,6-diyl diacrylate (B6). Side chain monomers used were 3-amino-1-propanol (S3), 4-amino-1-butanol (S4), or 5-amino-1-pentanol (S5). The end-cap used was 1-(3-aminopropyl)-4-methylpiperazine (E7). One of ordinary skill in the art would recognize that any of the base monomers, side chain monomers, and end capping groups disclosed herein would be suitable for use with the presently disclosed copolymer synthesis.

For all polymers, polymerization was completed using a base monomer to side chain ratio of 1.01:1 at 500 mg/mL in dimethyl sulfoxide (DMSO) at 90° C. for 24 hrs while stirring. The polymers were end-capped in DMSO at 100 mg/mL with 0.2 mM E7 for one h at room temperature while shaking.

For polymers synthesized with both base monomers, BR6 and B6 were combined in molar ratios of 3:1, 1:1, or 1:3 and dissolved in DMSO prior to adding the side chain monomer. Example polymers R647 and 647 were characterized via $H^1$-NMR. R647 base polymer: ($d_6$-DMSO, 400 Hz), δ1.3-1.5 (4H, br, $NCH_2CH_2CH_2CH_2OH$), δ2.3-2.5 (6H, br, $OOCCH_2CH_2N$ and $NCH_2CH_2CH_2CH_2OH$), δ2.6-2.7 (4H, t, $OOCCH_2CH_2N$), β2.9-3.1 (4H, t, $COOCH_2CH_2S$), δ4.2-4.4 (4H, t, $COOCH_2CH_2S$). $H^1$-NMR of 647 base polymer: ($d_6$-DMSO, 400 Hz), δ1.25-1.4 (8H, br, $NCH_2CH_2CH_2CH_2OH$ and $COOCH_2CH_2CH_2$), δ1.5-1.65 (4H, br, $COOCH_2CH_2CH_2$), δ2.3-2.4 (6H, br, $NCH_2CH_2CH_2CH_2OH$ and $OOCCH_2CH_2N$), δ2.6-2.7 (4H, br, $OOCCH_2CH_2N$), δ3.3-3.4 (2H, br, obsc, $NCH_2CH_2CH_2CH_2OH$), δ3.95-4.05 (4H, br t, $COOCH_2CH_2CH_2$), δ4.3-4.4 (br, $NCH_2CH_2CH_2OH$). $H^1$—NMR of E7 endcap: ($d_6$-DMSO, 400 Hz), δ1.50, (2H, quint, $NHCH_2CH_2CH_2N<(CH_2CH_2)>NCH_3$), δ2.13 (3H, s, $NHCH_2CH_2CH_2N<(CH_2CH_2)>NCH_3$), δ2.3-2.4 (10H, br, obsc, NHCH$_2$CH$_2$CH$_2$N<(CH$_2$CH$_2$)>NCH$_3$), δ2.47 (2H, t, NHCH$_2$CH$_2$CH$_2$N<(CH$_2$CH$_2$)>NCH$_3$).

D. siRNA Delivery to GBM 319 Cells and Cell Viability

GFP$^+$ GBM 319 glioblastoma cells were plated at a cell density of 15,000 cells/well in 96-well tissue culture plates in 89% GIBCO® DMEM-F12, 1% GIBCO®Antibiotic-Antimycotic (Invitrogen), and 10% Corning Cellgro®Heat-Inactivated FBS and allowed to adhere overnight. The siRNAs used were either siRNA targeting eGFP with sequence 5'-CAAGCUGACCCUGAAGUUCTT (sense) and 3'-GAACUUCAGGGUCAGCUUGCC (antisense), or a scrambled control siRNA (scRNA) with sequence 5'-AGUACUGCUUACGAUACGGTT (sense) and 3'-CCGUAUCGUAAGCAGUACUTT (anti-sense). For all transfections, siRNA and polymers were diluted in 25 mM NaAc at twelve times the final concentration listed for each group, and siRNA and polymers were combined in a 1:1 v/v ratio and allowed to form cells for 10 min at room temperature. As an example, nanoparticles listed at final concentrations of "180 μg/mL and 20 nM siRNA" were formed by mixing a 2.16 mg/mL solution of polymer with a 240 nM solution of siRNA. The cell culture media was removed and replaced with serum-free media prior to adding nanoparticles. Nanoparticle formulations were diluted in each well in quadruplicates in a 1:6 v/v ratio to yield the final siRNA and polymer concentrations listed for each group. Cells were incubated with nanoparticles for 4 h, after which the nanoparticle solutions were removed and fresh, serum-containing media was added. Cytoxicity was assessed 24 h after transfection CellTiter 96®AQ$_{ueous}$ One MTS assay following manufacturer's instructions.

E. Flow Cytometry

All flow cytometry was completed at nine days post-transfection using an Intellicyt high-throughput loader attached to an Accuri C6 flow cytometer. Hypercyt software was used to discriminate events between each well and FlowJo was used to analyze the flow cytometry results. Cells were prepared for flow cytometry by 5 min of trypsinization with 30 μL of 0.25% trypsin-EDTA, followed by the addition of 170 μL of a buffer of PBS containing 1:50 (v/v) FBS and 1:200 (v/v) propidium iodide (PI). Cell suspensions were moved to round-bottom 96-well plates and centrifuged for 5 min at 1000 rpm. A 170 μL aliquot of supernatant was removed and cells were resuspended in the remaining buffer. PI signal was used to distinguish dead or dying cells from live cells so that the unhealthy cells could be removed from analysis. GFP knockdown was determined by finding the geometric mean FL1 fluorescence signal for each sample. Percent knockdown was calculated by finding the difference in FL1 fluorescence of eGFP siRNA-treated cells and scRNA treated cells, normalized to scRNA treated cells.

F. Gel Retention Assay

Nanoparticles were formed using 0.01 mg/mL scrambled control RNA (scRNA) in 25 mM sodium acetate (NaAc) and polymer 1:1 R647 at weight ratios to scRNA ranging from 600 wt/wt to 0 wt/wt (siRNA) alone. These nanoparticles were incubated for 10 min at room temperature to allow for particle formation. To compare the effects of a nonreducing and reducing environment on the particles, either PBS or PBS containing L-glutathione (GSH) to yield a final GSH concentration of 0 mM or 5 mM, respectively, were added and allowed to incubate at room temperature for 15 min. A solution of 30% glycerol was added to the particles in a 1:5 v/v ratio. The particles were loaded into a 1% agarose gel containing 1 μg/mL ethidium bromide and electrophoresed at 100 mV for 20 min. Gels were visualized using UV light exposure.

G. Particle Size and Concentration Determination: Nanoparticle Tracking Analysis All nanoparticles were made in the same manner that they were for transfection and then diluted so that their sizes and concentrations could be accurately determined using Nanoparticle Tracking Analysis (NTA). NTA was performed using a NanoSight NS500 and analyzed using NanoSight NTA 2.4 software. As an example, particles for transfection groups labeled "180 μg/mL polymer with 20 nM siRNA" were synthesized by forming particles at a polymer concentration of 1.08 mg/mL and scRNA at 120 nM in NaAc, as these particles would be diluted in a 1:6 v/v ratio in media during transfection. For NTA, however, these particles were diluted in PBS following the protocol recommended by Bhise et al., Small 2012, 8, (3), 367-373. All measurements were repeated with three separate formulations for each condition. The NTA analysis reported the number-average hydrodynamic radius of the particles. All particle concentrations were reported as the number of particles per volume that would be present in the transfection wells.

siRNA loading was calculated by dividing the total amount of siRNA per transfection well by the number of particles per well. This calculation was only completed for particle formulations with wt/wt ratios high enough to completely bind all siRNA as determined by the gel retention assay. For this reason, any particle formulations with wt/wt ratios at or below 75 wt/wt were excluded from siRNA loading calculations.

H. Particle Zeta-Potential Determination: Dynamic Light Scattering

Particles were formed at the same concentrations and in the same manner as described for particle sizing. Particles were diluted 1:650 v/v in PBS and loaded into a disposable cuvette cell. Particle surface charge was determined via dynamic light scattering (DLS) using a Malvern Zetasizer NanoZS.

I. Transmission Electron Microscopy

Nanoparticles formed using 1:1 R647 at 180 μg/mL and 20 nM siRNA were imaged using transmission electron microscopy (TEM). 1:1 R647 was diluted to 2.16 μg/mL in 25 mM NaAc, scRNA was diluted to 240 nM in NaAc, and the two solutions were combined in a 1:1 v/v ratio and allowed to form particles for 10 min at room temperature. Following particle formation, 5 μL of the nanoparticle solution was placed onto a carbon-coated copper TEM grid and allowed to dry. Particles were imaged using a Philips/FEI BioTwin CM120 transmission electron microscope.

J. Gel Permeation Chromatography

GPC was performed using a Waters GPC system with three Waters Styragel columns in a series (HR 1, HR 3 and HR4) and a Waters 2414 refractive index detector, both maintained at 40° C. throughout all samples, which were loaded using a Waters 717plus autosampler (Waters Corp., Milford, MA). All samples were loaded at 5 mg/mL using 94% THF, 5% DMSO, and 1% piperidine (v/v) as the eluent at a flow rate of 1.0 mL/min for 40 min. Polymer molecular weights were calculated relative to polystyrene standards (Shodex, Japan).

K. Statistics

All results are presented as mean±standard error of the mean. Statistical significance results for all % GFP knockdown and % loss in metabolic activity were determined using a one-way ANOVA with Dunnett's post-tests using LIPOFECTAMINE™ 2000 as the control. All particle formulations that caused > 60% toxicity were excluded from statistical testing. A two-way ANOVA with Tukey's multiple comparisons post-test also was used to compare changes in loss in metabolic activities of cells treated with different polymers using side chain and base monomer as the parameters. R squared ($R^2$) correlation values were calculated compared to either linear or nonlinear regressions as labeled in each figure caption. All significance tests with $p<0.05$ were considered significant.

Example 6

Summary of Bioreducible Poly(β-Amino Ester) Copolymers for siRNA Delivery

In summary, the presently disclosed subject matter provides the synthesis and characterization of a siRNA delivery vehicle capable of near complete gene knockdown in human primary glioblastoma (GBM 319) cells that is safe and effective even at very low siRNA doses. By combining polymer hydrophobicity, a property known to promote enhanced siRNA and DNA delivery, Tzeng, S. Y.; Green, J. J. *Adv. Healthcare Mater.* 2012; Sunshine, J. C., et al., *Biomacromolecules* 2011, 12, (10), 3592-3600, with polymer bioreducibility, the cytotoxic effects typical of hydrophobic polymers were reduced while optimizing cytoplasmic cargo release and ultimately enhancing siRNA delivery.

The effects of changing nanoparticle formulation were examined and demonstrated that nanoparticle concentration is largely determined by polymer concentration, and that higher polymer concentrations promote enhanced siRNA delivery. Gene knockdown was shown to be effective (63±16%) at very low doses of siRNA (1 nM). Accordingly, the presently disclosed bioreducible PBAEs having tuneable hydrophobicities exhibit potential as safe siRNA delivery vehicles capable of effective gene knockdown with very low siRNA doses.

Example 7

Cross-Linked Bioreducible Polymeric Nanoparticles for siRNA Delivery

FIG. 14 demonstrates the efficacy of cross-linked bioreducible polymeric nanoparticles for siRNA delivery. GFP knockdown time course in GFP+ human primary glioblastoma cells (GBM 319 cells) is calculated by comparing the cells treated with polymeric nanoparticles containing siRNA that targets GFP to cells treated with polymeric nanoparticles containing scrambled control siRNA. Nanoparticles were formed by self-assembly with siRNA and either cationic bioreducible polymer R64Ac (the polymer intermediate formed in Scheme 1) or a 1:3 polymer blend of the polymers R647:R64Ac, with 60 nM siRNA, and 0.0083% Irgacure 2959, and were exposed to UV light for one min following particle formation to form crosslinks. Transfections were completed in media containing a final volume of 50% serum. The cross-linked nanoparticles show higher efficacy than non-crosslinked nanoparticles over many time points.

Example 8

Crosslinked and Bioreducible Poly(β-Amino Ester)-Based Nanoparticles for Enhanced siRNA Delivery siRNA delivery can lead to sequence-specific gene knockdown. In theory, siRNA can knockdown the translation of any protein. As a result, siRNA has the potential to cure diseases caused by aberrant gene expression. Rutz and Scheffold, *Arthritis Res. Ther.* 2004.

The main obstacles specific to siRNA delivery include the fact that siRNA needs to reach the cytosol to induce RNAi and that polymer siRNA nanoparticles usually are not stable. The presently disclosed subject matter provides bioreducible nanoparticles that release siRNA in the reducing cytosolic environment and which are crosslinked to promote stability. Referring now to FIG. 15 is schematic showing a representative pathway for siRNA delivery.

In particular issue with regard to siRNA delivery is cytosolic targeting. The presently disclosed subject matter addresses this issue by providing, in some embodiments, a disulfide-containing poly(β-amino ester) (PBAE) analog, e.g., R647. PBAEs previously have been shown to be safe and effective DNA delivery vehicles. In the presently disclosed PBAE analogs, the disulfide bonds are cleaved in reducing environments. For example, the cytosol is approximately 1000 times more reducing than the extracellular environment. A schematic showing the condensation of siRNA into a presently disclosed nanoparticle and the bioreduction of the nanoparticle and subsequent siRNA release are shown in FIG. 16. Referring once again to FIG. 5, the presently disclosed nanoparticle comprising disulfide-containing poly(β-amino ester) (PBAE) analogs, e.g., R647, allow redox-triggered siRNA release.

Further, referring once again to FIG. 7 and FIG. 8, the presently disclosed subject matter demonstrates siRNA delivery to GFP+ human glioblastoma cells. In this example, the polymer reducibility imparts effective siRNA delivery with minimal toxicity. This transfection, however, was conducted in serum-free conditions.

One issue, however, with PBAE/siRNA particles is that they are unstable. To address this issue, the presently disclosed subject matter, in some embodiments, provides cross-linked nanoparticles for enhanced stability. In such embodiments, a radical photoinitiator and UV light are used to produce crosslinked nanoparticles (see FIG. 17). The cross-linking can be confirmed using NMR (see FIG. 18).

Such nanoparticles exhibit effective in vitro siRNA delivery in 50% serum. See FIG. 19. The particles reached their target cells almost immediately, which is not a realistic scenario for intravenous (I.V.) particle injection. Further, the presently disclosed nanoparticles exhibit long-term particle efficacy. For example, referring to FIG. 20, the presently disclosed particles were preincubated in 50% serum prior to transfection. As shown in FIG. 20, the efficacy of cross-linked nanoparticles remained relatively constant over 5 hours, whereas the efficacy of uncrosslinked nanoparticles decreased over time.

Accordingly, the presently disclosed disulfide-containing PBAEs allow for environmentally-triggered siRNA release to the cytosol. Further, the polymer bioreducibility reduces cytoxicity. The presently disclosed crosslinked particles are stable and effective for at least five hours. In summary, the presently disclosed crosslinked and bioreducible PBAEs have the potential to safely and effectively deliver siRNA.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Fire, A.; Xu, S.; Montgomery, M. K.; Kostas, S. A.; Driver, S. E.; Mello, C. C. Nature 1998, 391, 806-11.

Kuwabara, P. E.; Coulson, A. Parasitol Today 2000, 16, 347-9.

Green, J. J.; Langer, R.; Anderson, D. G. Accounts of chemical research 2008, 41, 749-759.

Lynn, D. M.; Langer, R. Journal of the American Chemical Society 2000, 122, 10761-10768.

Sunshine, J. C.; Peng, D. Y.; Green, J. J., Molecular Pharmaceutics 2012, 9(11), 3375-3383.

Griffith, O. W. Free Radical Biology and Medicine 1999, 27, 922-935.

Chen, J.; Qiu, X.; Ouyang, J.; Kong, J.; Zhong, W.; Xing, M. M. Biomacromolecules, 2011, 12, 3601-11.

Bhise, N. S.; Gray, R. S.; Sunshine, J. C.; Htet, S.; Ewald, A. J.; Green, J. J. Biomaterials, 2010, 31, 8088-8096.

T. G. Park, J. H. Jeong, and S. W. Kim, "Current status of polymeric gene delivery systems," *Advanced Drug Delivery Reviews*, vol. 58, pp. 467-486, mL 7 2006.

D. W. Pack, A S. Hoffman, S. Pun, and P. S. Stayton, "Design and development of polymers for gene delivery," *Nature Reviews Drug Discovery*, vol. 4, pp. 581-593, mL 2005.

M. C. Pedroso de Lima, S. Simoes, P. Pires, H. Faneca, and N. Duzgunes, "Cationic lipid-DNA complexes in gene delivery: from biophysics to biological applications," *Advanced Drug Delivery Reviews*, vol. 47, pp. 277-94, Apr. 25 2001.

O. Boussif, F. Lezoualc'h, M. A Zanta, M. D. Mergny, D. Schennan, B. Demeneix, and J. P. Behr, "A versatile vector for gene and oligonucleotide transfer into cells in culture and in vivo: polyethylenimine," *Proc Natl Acad Sci USA*, vol. 92, pp. 7297-301, Aug. 1 1995.

N. D. Sonawane, F. C. Szoka, and A S. Verkrnan, "Chloride accumulation and swelling in endosomes enhances DNA transfer by polyamine-DNA polyplexes," *Journal of Biological Chemistry*, vol. 278, pp. 44826-44831, Nov. 7 2003.

A. Akinc, M. Thomas, A. M. Klibanov, and R. Langer, "Exploring polyethylenimine-mediated DNA transfection and the proton sponge hypothesis," *Journal of Gene Medicine*, vol. 7, pp. 657-663, MAY 2005.

D. Putnam, C. A Gentry, D. W. Pack, and R. Langer, "Polymer-based gene delivery with low cytotoxicity by a unique balance of side-chain tennini," *Proc Natl Acad Sci USA*, vol. 98, pp. 1200-5, Jan. 30 2001.

S. M. Moghimi, P. Symonds, J. C. Murray, A C. Hunter, G. Debska, and A Szewczyk, "A two-stage poly(ethylenimine)-mediated cytotoxicity: implications for gene transfer/therapy," *Mol Ther*, vol. 11, pp. 990-5, June 2005.

J. J. Green, D. G. Anderson, and R. Langer, "A combinatorial polymer library yields insights into the field of non-viral gene delivery," *Accounts of Chemical Research*, vol. 41, pp. 749-759, 2007.

D. M. Lynn and R. Langer, "Degradable poly(beta-amino esters): Synthesis, characterization, and self-assembly with plasmid DNA," *J Am Chem Soc*, vol. 122, pp. 10761-10768, 2000.

D. G. Anderson, A. Akinc, N. Hossain, and R. Langer, "Structure/property studies of polymeric gene delivery using a library of poly (beta-amino esters)," *Molecular Therapy*, vol. 11, pp. 426-34, March 2005.

A. Akinc, D. M. Lynn, D. G. Anderson, and R. Langer, "Parallel synthesis and biophysical characterization of a degradable polymer library for gene delivery," *Journal of the American Chemical Society*, vol. 125, pp. 5316-23, May 7 2003.

J. J. Green, J. Shi, E. Chiu, E. S. Leshchiner, R. Langer, and D. G. Anderson, "Biodegradable polymeric vectors for gene delivery to human endothelial cells," *Bioconjugate Chemistry*, vol. 17, pp. 1162-1169,2006.

A. Akinc, D. G. Anderson, D. M. Lynn, and R. Langer, "Synthesis of poly(beta-amino ester)s optimized for highly effective gene delivery," *Bioconjugate Chemistry*, vol. 14, pp. 979-988, SEP-OCT 2003.

J. J. Green, G. T. Zugates, N. C. Tedford, Y. Huang, L. G. Griffith, D. A Lauffenburger, J. A Sawicki, R. Langer, and D. G. Anderson, "Combinatorial modification of degradable polymers enables transfection of human cells comparable to adenovirus," *Advanced Materials, vol.* 19, pp. 2836-2842, 2007.

G. T. Zugates, W. Peng, A. Zumbuehl, S. Jhunjhunwala, Y. H. Huang, R. Langer, J. A Sawicki, and D. G. Anderson, "Rapid Optimization of Gene Delivery by Parallel Endmodification of Poly(beta-amino ester)s," *Mol Ther*, vol. 15, pp. 1306-1312, 2007.

M. A Gosselin, W. J. Guo, and R. J. Lee, "Efficient gene transfer using reversibly cross-linked low molecular weight polyethylenimine," *Bioconjugate Chemistry*, vol. 12, pp. 989-994, November-DEC 2001.

M. L. Forrest, J. T. Koerber, and D. W. Pack, "A degradable polyethylenimine derivative with low toxicity for highly efficient gene delivery," *Bioconjug Chem*, vol. 14, pp. 934-40, September-October 2003.

L. V. Christensen, C. W. Chang, W. J. Kim, S. W. Kim, Z. Zhong, C. Lin, J. F. Engbersen, and J. Feijen, "Reducible poly(amido ethylenimine)s designed for triggered intracellular gene delivery," *Bioconjugate Chemistry*, vol. 17, pp. 1233-40, September-October 2006.

C. Lin, C. J. Blaauboer, M. M. Timoneda, M. C. Lok, M. van Steenbergen, W. E. Hennink, Z. Zhong, J. Feijen, and J. F. Engbersen, "Bioreducible poly(amido amine)s with oligoamine side chains: synthesis, characterization, and structural effects on gene delivery," *Journal of Controlled Release*, vol. 126, pp. 166-74, March 32008.

J. Yu, M. A Vodyanik, K. Smuga-Otto, J. Antosiewicz-Bourget, J. L. Frane, S. Tian, J. Nie, G. A Jonsdottir, V. Ruotti, R. Stewart, Slukvin, II, and J. A Thomson, "Induced pluripotent stern cell lines derived from human somatic cells," *Science*, vol. 318, pp. 1917-20, Dee 21 2007.

M. M. O. Sullivan, J. J. Green, and T. M. Przybycien, "Development of a novel gene delivery scaffold utilizing colloidal gold-polyethylenimine conjugates for DNA condensation," *Gene Therapy*, vol. 10, pp. 1882-1890, October 2003.

A. J. Ewald, A. Brenot, M. Duong, B. S. Chan, and Z. Werb, "Collective Epithelial Migration and Cell Rearrangements Drive Mammary Branching Morphogenesis" *Dev Cell*. vol. 14(4) pp. 570-581, April 2008.

Fire, A.; Xu, S. Q.; Montgomery, M. K.; Kostas, S. A.; Driver, S. E.; Mello, C. C. *Nature* 1998, 391, (6669), 806-811.

Wu, W.; Sun, M.; Zou, G. M.; Chen, *J. Int. J. Cancer* 2007, 120, (5), 953-60.

Yadav, S.; van Vlerken, L. E.; Little, S. R.; Amiji, M. M. *Cancer Chemother. Pharmacol.* 2009, 63, (4), 711-22.

Akinc, A.; Zumbuehl, A.; Goldberg, M.; Leshchiner, E. S.; Busini, V.; Hossain, N.; Bacallado, S. A.; Nguyen, D. N.; Fuller, J.; Alvarez, R.; Borodovsky, A.; Borland, T.; Constien, R.; de Fougerolles, A.; Dorkin, J. R.; Jayaprakash, K. N.; Jayaraman, M.; John, M.; Koteliansky, V.; Manoharan, M.; Nechev, L.; Qin, J.; Racie, T.; Raitcheva, D.; Rajeev, K. G.; Sah, D. W. Y.; Soutschek, J.; Toudjarska, I.; Vornlocher, H. P.; Zimmermann, T. S.; Langer, R.; Anderson, D. G. *Nat. Biotechnol.* 2008, 26, (5), 561-569.

Semple, S. C.; Akinc, A.; Chen, J.; Sandhu, A. P.; Mui, B. L.; Cho, C. K.; Sah, D. W.; Stebbing, D.; Crosley, E. J.; Yaworski, E.; Hafez, I. M.; Dorkin, J. R.; Qin, J.; Lam, K.; Rajeev, K. G.; Wong, K. F.; Jeffs, L. B.; Nechev, L.; Eisenhardt, M. L.; Jayaraman, M.; Kazem, M.; Maier, M. A.; Srinivasulu, M.; Weinstein, M. J.; Chen, Q.; Alvarez, R.; Barros, S. A.; De, S.; Klimuk, S. K.; Borland, T.; Kosovrasti, V.; Cantley, W. L.; Tam, Y. K.; Manoharan, M.; Ciufolini, M. A.; Tracy, M. A.; de Fougerolles, A.; MacLachlan, I.; Cullis, P. R.; Madden, T. D.; Hope, M. *J. Nat. Biotechnol.* 2010, 28, (2), 172-6.

Derfus, A. M.; Chen, A. A.; Min, D. H.; Ruoslahti, E.; Bhatia, S. N. *Bioconjugate Chem.* 2007, 18, (5), 1391-1396.

Elbakry, A.; Zaky, A.; Liebl, R.; Rachel, R.; Goepferich, A.; Breunig, *M. Nano Lett.* 2009, 9, (5), 2059-2064.

Kakizawa, Y.; Furukawa, S.; Ishii, A.; Kataoka, K. *J. Control. Release* 2006, 111, (3), 368-370.

Breunig, M.; Hozsa, C.; Lungwitz, U.; Watanabe, K.; Umeda, I.; Kato, H.; Goepferich, A. *J. Control. Release* 2008, 130, (1), 57-63.

Jeong, J. H.; Christensen, L. V.; Yockman, J. W.; Zhong, Z. Y.; Engbersen, J. F. J.; Kim, W. J.; Feijen, J.; Kim, S. W. *Biomaterials* 2007, 28, (10), 1912-1917.

Matsumoto, S.; Christie, R. J.; Nishiyama, N.; Miyata, K.; Ishii, A.; Oba, M.; Koyama, H.; Yamasaki, Y.; Kataoka, K. *Biomacromolecules* 2009, 10, (1), 119-127.

Boussif, O.; Lezoualch, F.; Zanta, M. A.; Mergny, M. D.; Scherman, D.; Demeneix, B.; Behr, J. P. *Proc. Natl. Acad. Sci.* 1995, 92, (16), 7297-7301.

Lynn, D. M.; Langer, R. *J. Am. Chem. Soc.* 2000, 122, (44), 10761-10768.

Hagerman, P. J. *Annu. Rev. Biophys. Biomol. Struct.* 1997, 26, 139-156.

Kebbekus, P.; Draper, D. E.; Hagerman, P. *Biochemistry* 1995, 34, (13), 4354-4357.

Kawasaki, H.; Taira, K. *Nucleic Acids Res.* 2003, 31, (2), 700-707.

Griffith, O. W. *Free Radical Bio. Med.* 1999, 27, (9-10), 922-935.

Miyata, K.; Kakizawa, Y.; Nishiyama, N.; Harada, A.; Yamasaki, Y.; Koyama, H.; Kataoka, K. *J. Am. Chem. Soc.* 2004, 126, (8), 2355-2361.

Tzeng, S. Y.; Green, J. J. *Adv. Healthcare Mater.* 2013, 2, (3) 467.

Tzeng, S. Y.; Hung, B. P.; Grayson, W. L.; Green, J. J. *Biomaterials* 2012, 33, (32), 8142-8151.

Kozielski, K. L.; Tzeng, S. Y.; Green, J. J. *Chem. Commun.* 2013, 49, 5319-5321.

Sunshine, J. C.; Akanda, M. I.; Li, D.; Kozielski, K. L.; Green, J. J. *Biomacromolecules* 2011, 12, (10), 3592-3600.

Chen, J.; Qiu, X.; Ouyang, J.; Kong, J.; Zhong, W.; Xing, M. M. *Biomacromolecules* 2011, 12, (10), 3601-11.

Bhise, N. S.; Gray, R. S.; Sunshine, J. C.; Htet, S.; Ewald, A. J.; Green, J. J. *Biomaterials* 2010, 31, (31), 8088-8096.

Tzeng, S. Y.; Guerrero-Cazares, H.; Martinez, E. E.; Sunshine, J. C.; Quiñones-Hinojosa, A.; Green, J. J. *Biomaterials* 2011, 32, (23), 5402-5410.

Bhise, N. S.; Shmueli, R. B.; Gonzalez, J.; Green, J. J. *Small* 2012, 8, (3), 367-373.

Rutz, S., and Scheffold, A., *Arthritis Res Ther* 2004, 6, 78-85 (2004).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A nanoparticle or microparticle comprising siRNA or miRNA and a compound of formula (I) or formula (II):

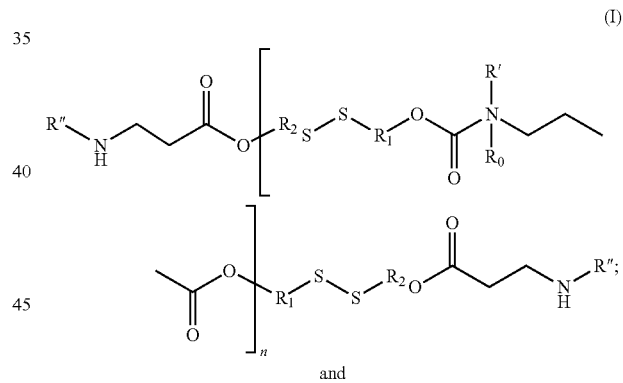

and

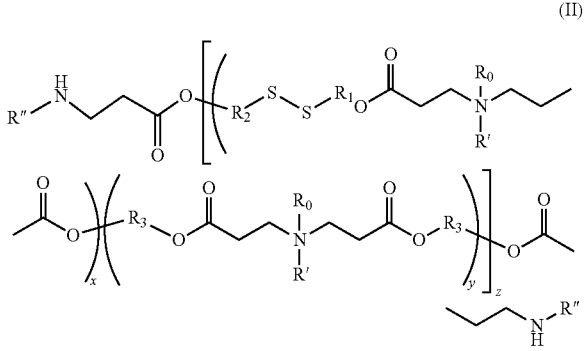

wherein:
n is an integer from 1 to 10,000;
X and Y are integers selected from 1 and 3;
Z is an integer from 1 to 10,000;

$R_1$ and $R_2$ can be the same or different and are each independently a $C_1$-$C_{30}$ alkyl chain;
each $R_3$ is a $C_3$-$C_8$ linear or branched alkyl chain;
R' is a side chain derived from:
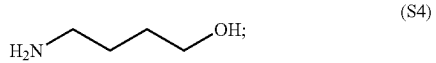
(S4)
the R" end groups are the same or different and are derived from a compound selected from the group consisting of:
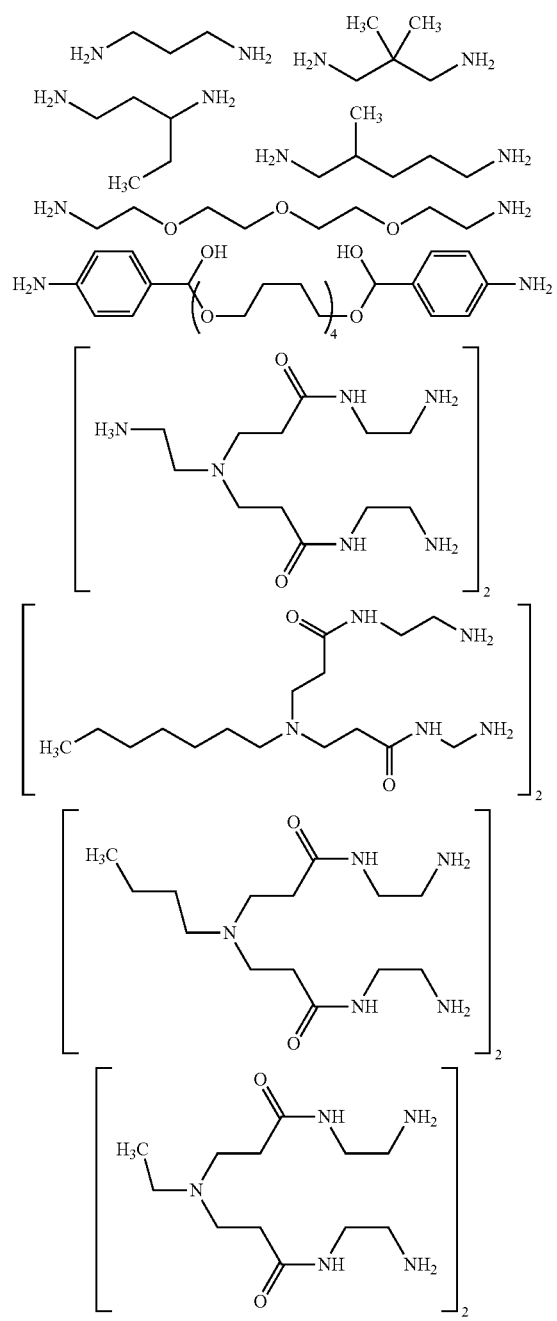
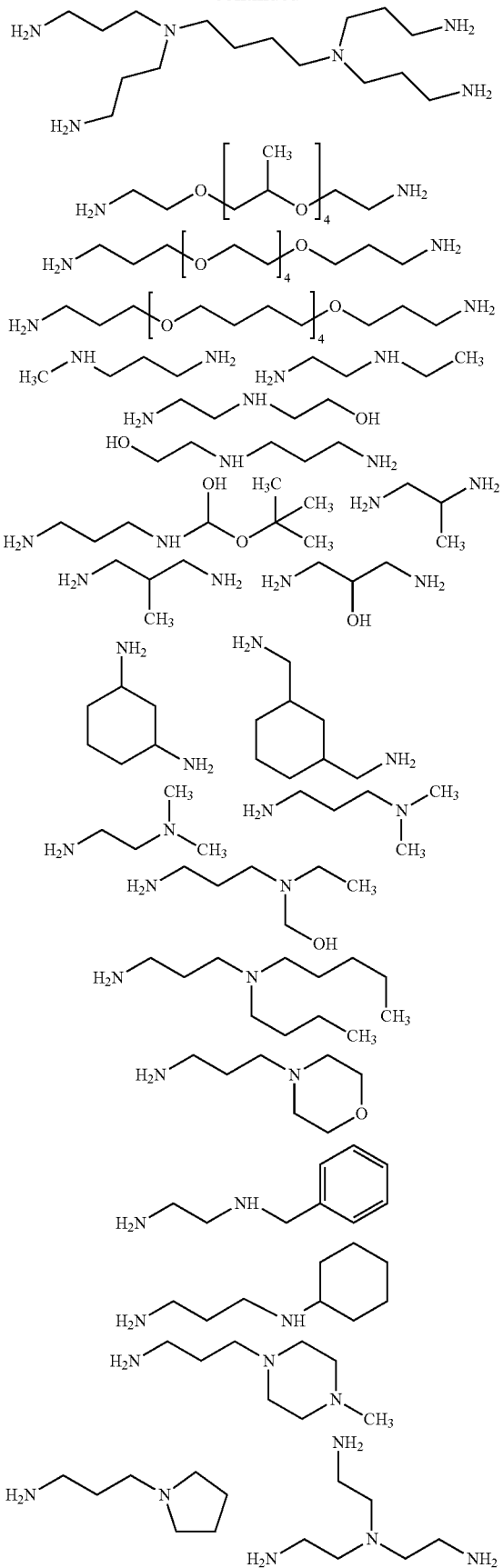

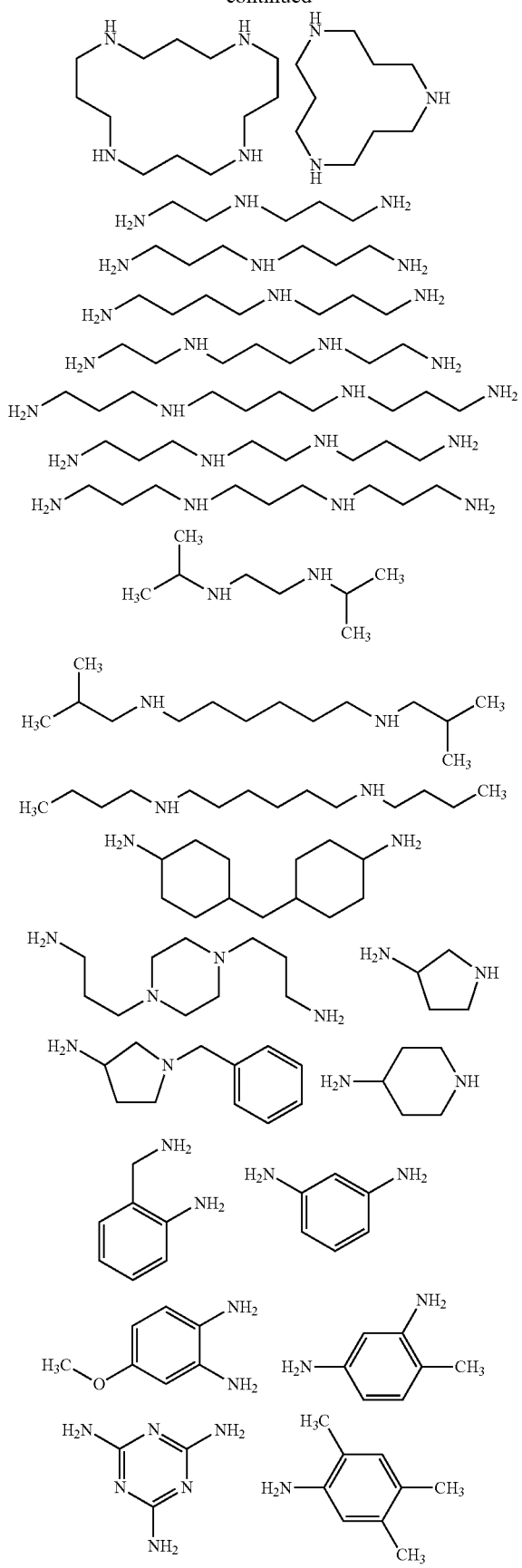
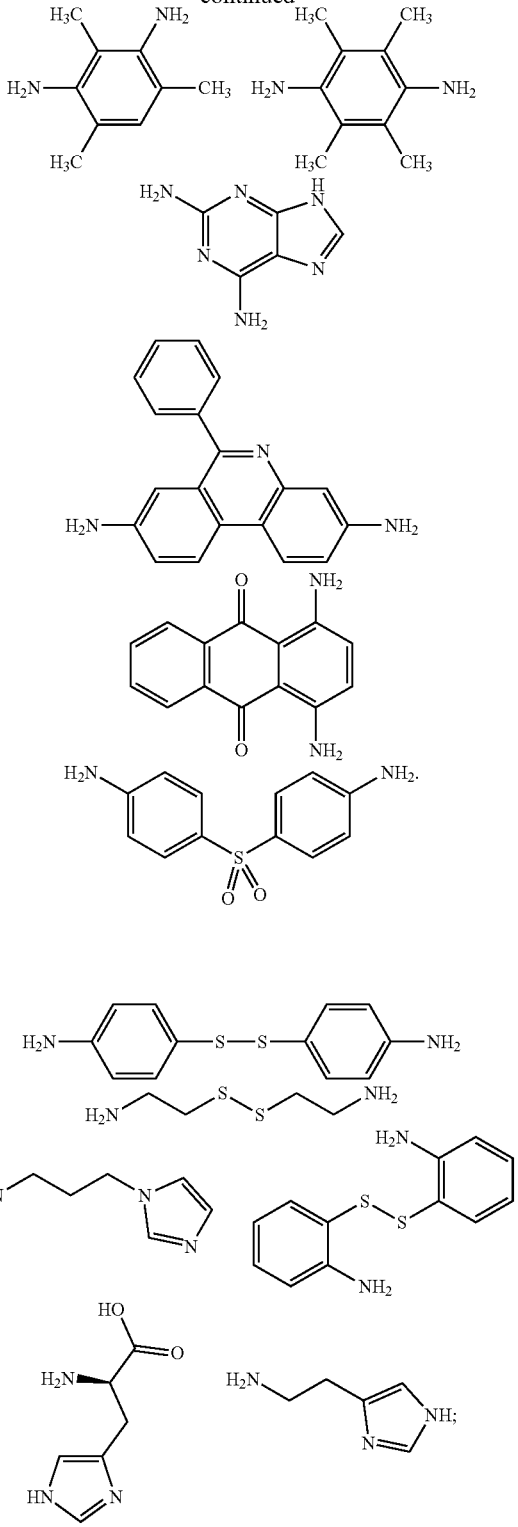
or R" comprises a biomolecule selected from the group consisting of poly(ethyleneglycol) (PEG), a targeting ligand, and a labeling molecule, or R" comprises a $C_1$-$C_{30}$ alkyl chain, wherein the $C_1$-$C_{30}$ alkyl chain is terminated with a functional group selected from the group consisting of —OH and —$NH_2$; and pharmaceutically acceptable salts thereof.

2. The nanoparticle or microparticle of claim 1, wherein the compound from which the same or different R″ end groups are derived is selected from the group consisting of:

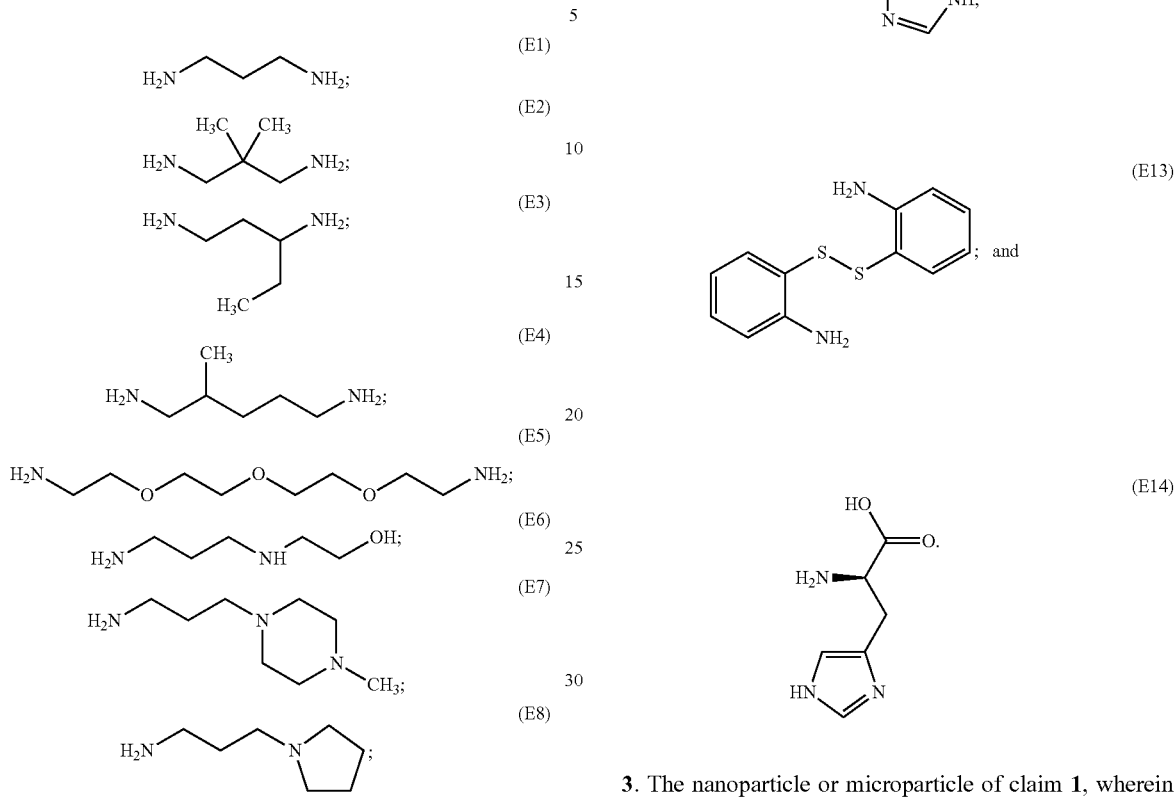

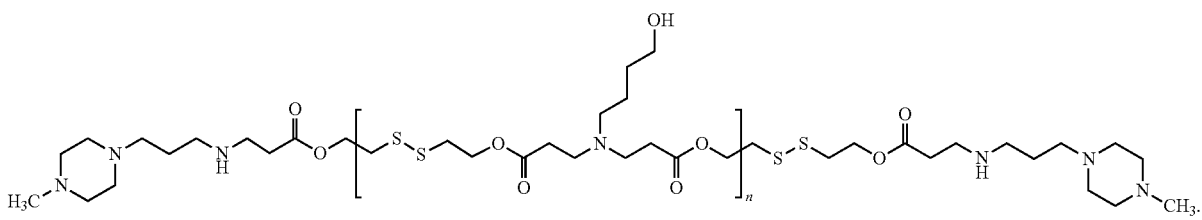

3. The nanoparticle or microparticle of claim 1, wherein the compound of formula (I) has the following structure:

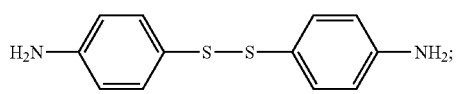

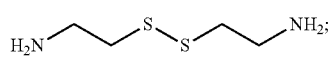

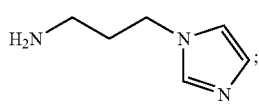

4. The nanoparticle or microparticle of claim 1, wherein the targeting ligand is selected from the group consisting of a sugar, a small molecule, an antibody, an antibody fragment, and a peptide.

5. The nanoparticle or microparticle of claim 1, wherein the labeling molecule is selected from the group consisting of a small molecule, a quantum dot, a nanoparticle, a fluorescent molecule, a luminescent molecule, and a contrast agent.

6. The nanoparticle or microparticle of claim 1, wherein the PEG has a molecular weight between about 5 kDa and about 30 kDa.

7. The nanoparticle or microparticle of claim 1, wherein n is an integer selected from the group consisting of from 1 to 1,000, from 1 to 100, from 1 to 30, from 5 to 20, and from 10 to 15.

8. The nanoparticle or microparticle of claim 1, wherein the compound of formula (I) or formula (II) is crosslinked.

9. A pharmaceutical composition comprising the nanoparticle or microparticle of claim 1.

10. A method for treating a disease or condition, the method comprising administering to a subject in need thereof, the nanoparticle or microparticle of claim 1 or a pharmaceutical composition thereof.

11. The method of claim 10, wherein the disease or condition is selected from the group consisting of a cancer, a cardiovascular disease, an infectious disease, and an ophthalmic disease.

12. A method of delivering siRNA or miRNA to a cell, a cell line, a tissue, or an organism, the method comprising contacting one or more of the nanoparticles or microparticles of claim 1 with the cell, cell line, tissue or organism.

13. The method of claim 12, wherein the siRNA or miRNA is released from the one or more nanoparticles or microparticles after entering the cell, binds to its complementary mRNA, and the complementary mRNA is cleaved.

14. The method of claim 13, wherein the siRNA or miRNA is released from the one or more nanoparticles or microparticles while the compound of formula (I) or formula (II) is degrading, thereby allowing sustained release of the siRNA or miRNA.

15. The method of claim 12, wherein the one or more nanoparticles or microparticles enter the cytoplasm of the cell.

16. The method of claim 15, wherein the compound of formula (I) or formula (II) is degraded reductively in the cytoplasm to release the siRNA or miRNA in the cytoplasm.

17. The method of claim 16, wherein at least one disulfide bond of the compound of formula (I) or formula (II) is degraded reductively in the cytoplasm.

18. The method of claim 17, wherein the at least one disulfide bond is degraded reductively by glutathione.

19. A kit comprising the nanoparticle or microparticle compound of claim 1 or a pharmaceutical composition thereof.

20. A biomedical device comprising the nanoparticle or microparticle of claim 1 or a pharmaceutical composition thereof.

21. The biomedical device of claim 20, wherein the biomedical device comprises a stent or a stent-like device.

22. The nanoparticle or microparticle of claim 1, wherein the nanoparticle or microparticle has at least one dimension ranging from about 1 nm to about 300 nm.

23. The nanoparticle or microparticle of claim 22, wherein the nanoparticle or microparticle has at least one dimension of about 100 nm.

24. A method of storing the nanoparticle or microparticle of claim 1, the method comprising adding a cryoprotectant to the nanoparticle or microparticle to form a mixture and lyophilizing the mixture to form storable powder of the nanoparticle or microparticle.

25. The method of claim 24, wherein the cyroprotectant comprises a sugar.

26. A method of silencing a gene in a cell, the method comprising contacting the cell with one or more of the nanoparticles or microparticles of claim 1, wherein the one or more nanoparticles or microparticles enter the cytoplasm of the cell, wherein the compound of formula (I) or formula (II) is reductively degraded in the cytoplasm thereby releasing the siRNA or miRNA from the one or more nanoparticles or microparticles, thereby silencing the gene.

27. The method of claim 26, wherein at least one disulfide bond of the compound of formula (I) or formula (II) is degraded reductively in the cytoplasm.

28. The method of claim 27, wherein the at least one disulfide bond is degraded reductively by glutathione.

29. The method of claim 11, where in the cancer is selected from the group consisting of brain cancer, lung cancer, breast cancer, prostate cancer, and colorectal cancer.

30. The method of claim 29, wherein the brain cancer is Glioblastoma Multiforme.

31. The method of claim 11, wherein the ophthalmic disease is age-related macular degeneration.

* * * * *

UNITED STATES PATENT AND TRADEMARK OFFICE
CERTIFICATE OF CORRECTION

PATENT NO. : 12,371,522 B2
APPLICATION NO. : 14/438353
DATED : July 29, 2025
INVENTOR(S) : Jordan J Green et al.

It is certified that error appears in the above-identified patent and that said Letters Patent is hereby corrected as shown below:

In the Claims

Claim 1, Column 53, Lines 30-39 should read:

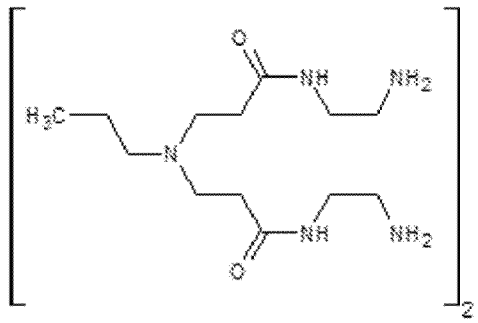

Claim 1, Column 54, Lines 37-41 should read:

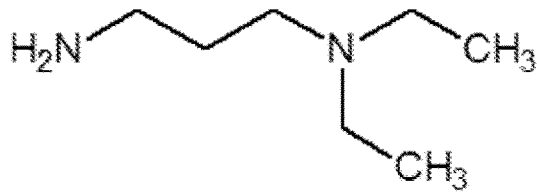

Signed and Sealed this
Sixteenth Day of September, 2025

Coke Morgan Stewart
*Acting Director of the United States Patent and Trademark Office*